US009381210B2

(12) United States Patent
Slukvin et al.

(10) Patent No.: US 9,381,210 B2
(45) Date of Patent: Jul. 5, 2016

(54) INDUCED PLURIPOTENT STEM CELL MODEL OF CHRONIC MYELOID LEUKEMIA REVEALED OLFACTOMEDIN 4 AS A NOVEL THERAPEUTIC TARGET IN LEUKEMIA STEM CELLS

(71) Applicant: Wisconsin Alumni Research Foundation, Madison, WI (US)

(72) Inventors: Igor I. Slukvin, Madison, WI (US); Kran Suknuntha, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 67 days.

(21) Appl. No.: 14/251,231

(22) Filed: Apr. 11, 2014

(65) Prior Publication Data
US 2015/0005361 A1 Jan. 1, 2015

Related U.S. Application Data

(60) Provisional application No. 61/812,014, filed on Apr. 15, 2013.

(51) Int. Cl.
*A61K 31/70* (2006.01)
*C07H 21/02* (2006.01)
*C07H 21/04* (2006.01)
*A61K 31/713* (2006.01)
*A61K 31/506* (2006.01)
*G01N 33/50* (2006.01)
*C12N 5/095* (2010.01)
*C12N 5/0789* (2010.01)
*G01N 33/574* (2006.01)
*A61K 45/06* (2006.01)
*A61K 31/496* (2006.01)
*A61K 31/5025* (2006.01)
*A61K 31/517* (2006.01)
*C12N 5/00* (2006.01)

(52) U.S. Cl.
CPC ............. *A61K 31/713* (2013.01); *A61K 31/496* (2013.01); *A61K 31/506* (2013.01); *A61K 31/5025* (2013.01); *A61K 31/517* (2013.01); *A61K 45/06* (2013.01); *C12N 5/0647* (2013.01); *C12N 5/0695* (2013.01); *G01N 33/5011* (2013.01); *G01N 33/5044* (2013.01); *G01N 33/57426* (2013.01); *C12N 2501/125* (2013.01); *C12N 2501/22* (2013.01); *C12N 2501/2303* (2013.01); *C12N 2501/2306* (2013.01); *C12N 2501/26* (2013.01); *C12N 2502/1358* (2013.01); *G01N 2333/9121* (2013.01); *G01N 2500/10* (2013.01)

(58) Field of Classification Search
None
See application file for complete search history.

(56) References Cited

U.S. PATENT DOCUMENTS

2014/0154303 A1* 6/2014 Tan .................. C12N 15/113
424/450

OTHER PUBLICATIONS

Liu et al. Blood vol. 116(23):4938-4947, 2009.*
Liu et al. ASH Annual Meeting Abstracts vol. 114(22):946, Nov. 20, 2009.*
Bhatia, R., Munthe, H.A., and Forman, S.J. (2001). Abnormal growth factor modulation of beta1-integrin-mediated adhesion in chronic myelogenous leukaemia haematopoietic progenitors. Br J Haematol 115, 845-853.
Bhatia, R., Munthe, H.A., Williams, A.D., Zhang, F., Forman, S.J., and Slovak, M.L. (2000). Chronic myelogenous leukemia primitive hematopoietic progenitors demonstrate increased sensitivity to growth factor-induced proliferation and maturation. Exp Hematol 28, 1401-1412.
Bruns, I., Czibere, A., Fischer, J.C., Roels, F., Cadeddu, R.P., Buest, S., Bruennert, D., Huenerlituerkoglu, A.N., Stoecklein, N.H., Singh, R., et al. (2009). The hematopoietic stem cell in chronic phase CML is characterized by a transcriptional profile resembling normal myeloid progenitor cells and reflecting loss of quiescence. Leukemia 23, 892-899.
Carette, J.E., Pruszak, J., Varadarajan, M., Blomen, V.A., Gokhale, S., Camargo, F.D., Wernig, M., Jaenisch, R., and Brummelkamp, T.R. (2010). Generation of iPSCs from cultured human malignant cells. Blood 115, 4039-4042.
Choi, K.D., Vodyanik, M.A., and Slukvin, II (2009a). Generation of mature human myelomonocytic cells through expansion and differentiation of pluripotent stem cell-derived in-CD34+CD43+CD45+ progenitors. J Clin Invest 119, 2818-2829.
Choi, K.D., Yu, J., Smuga-Otto, K, Salvagiotto, G., Rehrauer, W., Vodyanik, M., Thomson, J., and Slukvin, I. (2009b ). Hematopoietic and endothelial differentiation of human induced pluripotent stem cells. Stem Cells 27, 559-567.
Clemmensen, S.N., Bohr, C.T., Rorvig, S., Glenthoj, A., Mora-Jensen, H., Cramer, E.P., Jacobsen, L.C., Larsen, M.T., Cowland, J.B., Tanassi, J.T., et al. (2012). Olfactomedin 4 defines a subset of human neutrophils. J Leukoc Biol 91, 495-500.
Copland, M., Hamilton, A., Elrick, L.J., Baird, J.W., Allan, E.K., Jordanides, N., Barow, M., Mountford, J.C., and Holyoake, T.L (2006). Dasatinib (BMS-354825) targets an earlier progenitor population than imatinib in primary CML but does not eliminate the quiescent fraction. Blood 107, 4532-4539.

(Continued)

*Primary Examiner* — Sean McGarry
(74) *Attorney, Agent, or Firm* — Quarles & Brady LLP

(57) ABSTRACT

Disclosed herein are compositions and methods to treat and reduce therapeutic resistance in chronic myelogenous leukemia. Also disclosed herein are methods to generate leukemia stem cell like cells (iLSCs) generated from CML patient-derived iPSCs, and methods for utilizing iLSCs in screens to identify modulators of CML drug resistance and gene targets that underlie CML drug resistance.

6 Claims, 17 Drawing Sheets

(56) References Cited

OTHER PUBLICATIONS

Corbin, AS., Agarwal, A., Loriaux, M., Cortes, J., Deininger, M.W., and Druker, B.J. (2011). Human chronic myeloid leukemia stem cells are insensitive to imatinib despite inhibition of BCR-ABL activity. J Clin Invest 121, 396-409.

Diaz-Blanco, E, Bruns, I., Neumann, F., Fischer, J.C., Graef, T., Rosskopf, M., Brors, B., Pechtel, S., Bark, S., Koch, A., et al. (2007). Molecular signature of CD34(+) hematopoietic stem and progenitor cells of patients with CML in chronic phase. Leukemia 21, 494-504.

Druker, B.J., Guilhot, F., O'Brien, S.G., Gathmann, 1., Kantarjian, H., Gattermann, N., Deininger, M.W., Silver, R.T., Goldman, J.M., Stone, R.M., et al. (2006). Five-year follow-up of patients receiving imatinib for chronic myeloid leukemia. N. Engl J Med 355, 2408-2417.

Druker, B.J., Talpaz, M., Resta, D.J., Peng, B., Buchdunger, E., Ford, J.M., Lydon, N. B., Kantarjian, H., Capdeville, R., Ohno-Jones, S., et al. (2001). Efficacy and safety of a specific inhibitor of the BCR-ABL tyrosine kinase in chronic myeloid leukemia. N Engl J Med 344, 1031-1037.

Gandre-Babbe, S., Paluru, P., Aribeana, C., Chou, S.T., Bresolin, S., Lu, L., Sullivan, S.K., Tasian, S.K., Weng, J. Favre, H., et al. (2013). Patient-derived induced pluripotent stem cells recapitulate hematopoietic abnormalities of juvenile myelomonocytic leukemia. Blood 121, 4925-4929.

Graham, S.M., Jorgensen, H.G., Allan, E., Pearson, C., Alcorn, M.J., Richmond, L., and Holyoake, T.L. (2002). Primitive, quiescent, Philadelphia-positive stem cells from patients with chronic myeloid leukemia are insensitive to STI5 71 in vitro. Blood 99, 319-325.

Grskovic, M., Javaherian, A., Strulovici, B., and Daley, G.Q. (2011). Induced pluripotent stem cells—opportunities for disease modelling and drug discovery. Nat Rev Drug Discov 10, 915-929.

Holtz, M.S., Slovak, M.L., Zhang, F., Sawyers, C.L., Forman, S.J., and Bhatia, R. (2002). Imatinib mesylate (STI 5 71) inhibits growth of primitive malignant progenitors in chronic myelogenous leukemia through reversal of abnormally increased proliferation. Blood 99, 3792-3800.

Holyoake, T., Jiang, X., Eaves, C., and Eaves, A. (1999). Isolation of a highly quiescent subpopulation of primitive leukemic cells in chronic myeloid leukemia. Blood 94, 2056-2064.

Holyoake, T.L., Jiang, X., Jorgensen, H.G., Graham, S., Alcorn, M.J., Laird, C., Eaves, A.C., and Eaves, C.J. (2001). Primitive quiescent leukemic cells from patients with chronic myeloid leukemia spontaneously initiate factor-independent growth in vitro in association with up-regulation of expression of interleukin-3. Blood 97, 720-728.

Hu, K., Yu, J., Suknuntha, K., Tian, S., Montgomery, K., Choi, K.D., Stewart, R., Thomson, J.A., and Slukvin, II (2011). Efficient generation of transgene-free induced pluripotent stem cells from normal and neoplastic bone marrow and cord blood mononuclear cells. Blood 117, e109-119.

Huang da, W., Sherman, B.T., Stephens, R., Baseler, M.W., Lane, H.C., and Lempicki, R.A. (2008). David gene ID conversion tool. Bioinformation 2, 428-430.

Huang, G., Lu, H., Hao, A., Ng, D.C., Ponniah, S., Guo, K., Lufei, C., Zeng, Q., and Cao, X. (2004). GRIM-19, a cell death regulatory protein, is essential for assembly and function of mitochondrial complex I. Mol Cell Biol 24, 8447-8456.

Jiang, X., Lopez, A., Holyoake, T., Eaves, A., and Eaves, C. (1999). Autocrine production and action of IL-3 and granulocyte colony-stimulating factor in chronic myeloid leukemia. Proc Nat Acad Sci US A 96, 12804-12809.

Koshida, S., Kobayashi, D., Moriai, R., Tsuji, N., and Watanabe, N. (2007). Specific overexpression of OLFM4 (GW112/HGC-1) mRNA in colon, breast and lung cancer tissues ietected using quantitative analysis. Cancer science 98, 315-320.

Kumano, K, Arai, S., Hosoi, M., Taoka, K, Takayama, N., Otsu, M., Nagae, G., Ueda, K., \Nakazaki, K., Kamikubo, Y., et al. (2012). Generation of induced pluripotent stem cells from primary chronic myelogenous leukemia patient samples. Blood 119, 6234-6242.

Langmead, B., Trapnell, C., Pop, M., and Salzberg, S.L. (2009). Ultrafast and memory-efficient alignment of short DNA sequences to the human genome. Genome Biol1 0, R25.

Leng, N., Dawson, J.A., Thomson, J.A., Ruotti, V., Rissman, AI., Smits, B.M., Haag, J.D., Gould, M.N., Stewart, R.M., and Kendziorski, C. (2013). EBSeq: an empirical Bayes hierarchical model for inference in RNA-seq experiments. Bioinformatics 29, 1035-1043.

Li, B., and Dewey, C.N. (2011). RSEM: accurate transcript quantification from RNA-Seq data with or without a reference genome. BMC Bioinformatics 12, 323.

Li, G., Chan, T.M. Leung, K.S., and Lee, K.H. (2010). A cluster refinement algorithm for motif discovery. IEEE/ ACM Trans Comput Biol Bioinform 7, 654-668.

Li, L., Wang, L., Wang, Z., Ho, Y., McDonald, T., Holyoake, T.L., Chen, W., and Bhatia, R. (2012). Activation of p53 by SIRT1 inhibition enhances elimination of CML leukemia stem cells in combination with imatinib. Cancer Cell 21, 266-281.

Liu, R.H., Yang, M.H., Xiang, H., Bao, L.M., Yang, H.A., Yue, L.W., Jiang, X., Ang, N., Wu, L.Y., and Huang, Y. (2012). Depletion of OLFM4 gene inhibits cell growth and increases sensitization to hydrogen peroxide and tumor necrosis factor-alpha induced-apoptosis in gastric cancer mils. J Biomed Sci 19, 38.

Liu W., Chen, L., Zhu, J., and Rodgers, G.P. (2006). The glycoprotein hGC-1 binds to cadherin and lectins. Exp Cell Res 312, 1785-1797.

Liu, W., Lee, H.W., Liu, Y., Wang, R., and Rodgers, G.P. (2010). Olfactomedin 4 is a novel target gene of retinoic acids and 5-aza -2'-deoxycytidine involved in human myeloid leukemia cell growth, differentiation, and apoptosis. Blood 116, 4938-4947.

Liu, Y., Cheng, H. Gao, S., Zou, Z., He, F., Hu L., Hou D., Lu, X., Li, Y., Zhang, H., et al. (2013). Reprogramming of MLL-AF9 leukemia cells into pluripotent stem cells. Leukemia.

Oh, H.K., Tan, A.L., Das, K., Ooi, C.H., Deng, N.T., Tan, I.B., Beillard, E., Lee, J., Ramnarayanan, K., Rha, S.Y., eta/. (2011). Genomic loss of miR-486 regulates tumor progression and the OLFM4 antiapoptotic factor in gastric cancer. Clin Cancer Res 17, 2657-2667.

Park, I.H., Zhao, R., West, J.A., Yabuuchi, A., Huo, H., Ince, T.A., Lerou, P.H., Lensch, M.W., and Daley, G.Q. (2008). Reprogramming of human somatic cells to pluripotency with defined factors. Nature 451, 141-146. Epub Dec. 2007 2023.

Park, K.S., Kim, K.K., Piao, Z.H., Kim, M.K., Lee, H.J., Kim, Y.C., Lee, K.S., Lee, J.H., and Kim, K.E. (2012). Olfactomedin 4 suppresses tumor growth and metastasis of mouse melanoma cells through downregulation of integrin and MMP genes. Mol Cells 34, 555-561.

Petzer, A.L., Eaves, C.J., Lansdorp, P.M., Ponchio, L., Barnett, M.J., and Eaves, A.C. (1996). Characterization of primitive subpopulations of normal and leukemic cells present in the blood of patients with newly diagnosed as well as established chronic myeloid leukemia. Blood 88, 2162-2171.

Pfaffl, M.W. (2001). A new mathematical model for relative quantification in real-time RT-PCR. Nucleic Acids Res 29, e45.

Rais, Y., Zviran, A., Geula, S., Gafni, 0., Chomsky, E., Viukov, S., Mansour, A.A., Caspi, I., Krupalnik, V., Zerbib, M., et al. (2013). Deterministic direct reprogramming of somatic cells to pluripotency. Nature 502, 65-70.

Ramaraj, P., Singh, H., Niu, N., Chu, S., Holtz, M., Yee, J.K., and Bhatia, R. (2004). Effect of mutational inactivation of tyrosine kinase activity on BCR/ABL-induced abnormalities in cell growth and adhesion in human hematopoietic progenitors. Cancer Res 64, 5322-5331.

Ramos-Mejia, V., Montes, R., Bueno, C., Ayllon, V., Real, P.J., Rodriguez, R., and Menendez, P. (2012). Residual expression of the reprogramming factors prevents differentiation of iPSC generated from human fibroblasts and cord blood CD34+ progenitors. PLoS One 7, e35824.

Schemionek, M., Elling, C., Steidl, U., Baumer, N., Hamilton, A., Spieker, T., Gothert, Jr., Stehling, M., Wagers, A., Huettner, C.S., et al. (2010). BCR-ABL enhances differentiation of long-term repopulating hematopoietic stem cells. Blood 115, 3185-3195.

Sebaugh, J.L. (2011). Guidelines for accurate EC50/IC50 estimation. Pharm Stat 10, 128-134.

(56) References Cited

OTHER PUBLICATIONS

Stoma, I., Jiang, X., Eaves, A.C., and Eaves, C.J. (2010). Insights into the stem cells of chronic myeloid leukemia. Leukemia 24, 1823-1833.

Slukvin, II (2009). Neoplastic blood cells become pluripotent. Blood 114, 5409-5410.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Tomarev, S.I., and Nakaya, N. (2009). Olfactomedin domain-containing proteins: possible mechanisms of action and functions in normal development and pathology. Mol Neurobiol 40, 122-138.

Udomsakdi, C., Eaves, C.J., Lansdorp, P.M., and Eaves, A.C. (1992a). Phenotypic heterogeneity of primitive leukemic hematopoietic cells in patients with chronic myeloid leukemia. Blood 80, 2522-2530.

Udomsakdi, C., Lansdorp, P.M., Hogge, D.E., Reid, D.S., Eaves, A.C., and Eaves, C.J. (1992b). Characterization of primitive hematopoietic cells in normal human peripheral blood. Blood 30, 2513-2521.

van der Flier, L.G., Haegebarth, A., Stange, D.E., van de Wetering, M., and Clevers, H. (2009). OLFM4 is a robust marker for stem cells in human intestine and marks a subset of colorectal cancer cells. Gastroenterology 137, 15-17.

Vargaftig, J., Taussig, D.C., Griessinger, E, Anjos-Afonso, F., Lister, T.A., Cavenagh, J., Oakervee, H., Gribben, J., and Bonnet, D. (2012). Frequency of leukemic initiating cells does not depend on the xenotransplantation model used. Leukemia 26, 858-860.

Verfaillie, C.M., McCarthy, J.B., and McGlave, P.B. (1992). Mechanisms underlying abnormal trafficking of malignant progenitors in chronic myelogenous leukemia. Decreased adhesion to stroma and fibronectin but increased adhesion to the basement membrane components laminin and collagen type IV. The Journal of clinical investigation 90, 1232-1241.

Vodyanik, M.A., Bark, J.A., Thomson, J.A., and Slukvin, II (2005). Human embryonic stem cell-derived CD34+ cells: efficient production in the coculture with OP9 stromal cells and analysis of lymphohematopoietic potential. Blood 105, 617-626.

Vodyanik, M.A., Thomson, J.A., and Slukvin, II (2006). Leukosialin (CD43) defines hematopoietic progenitors in human embryonic stem cell differentiation cultures. Blood 108, 2095-2105.

Ye, Z., Zhan, H., Mali, P., Dowey, S., Williams, D.M., Jang, Y.Y., Dang, C.V., Spivak, J.L., Molitemo, A.R., and Cheng, L. (2009). Human-induced pluripotent stem cells from blood cells of healthy donors and patients with acquired blood disorders. Blood 114, 54 73-5480.

Yu, J., Hu, K., Smuga-Otto, K., Tian, S., Stewart, R., Slukvin, II, and Thomson, J.A. (2009). Human induced pluripotent stem cells free of vector and transgene sequences. Science 324, 797-801.

Zhang, J., Liu, W.L., Tang, D.C., Chen, L., Wang, M., Pack, S.D., Zhuang, Z., and Rodgers, G.P. (2002). Identification and characterization of a novel member of olfactomedin-related protein family, hGC-1, expressed during myeloid lineage development. Gene 283, 83-93.

Zhang, X., Huang, Q., Yang, Z., Li, Y., and Li, C.Y. (2004). GW112, a novel antiapoptotic protein that promotes tumor growth. Cancer Res 64, 2474-2481.

\* cited by examiner

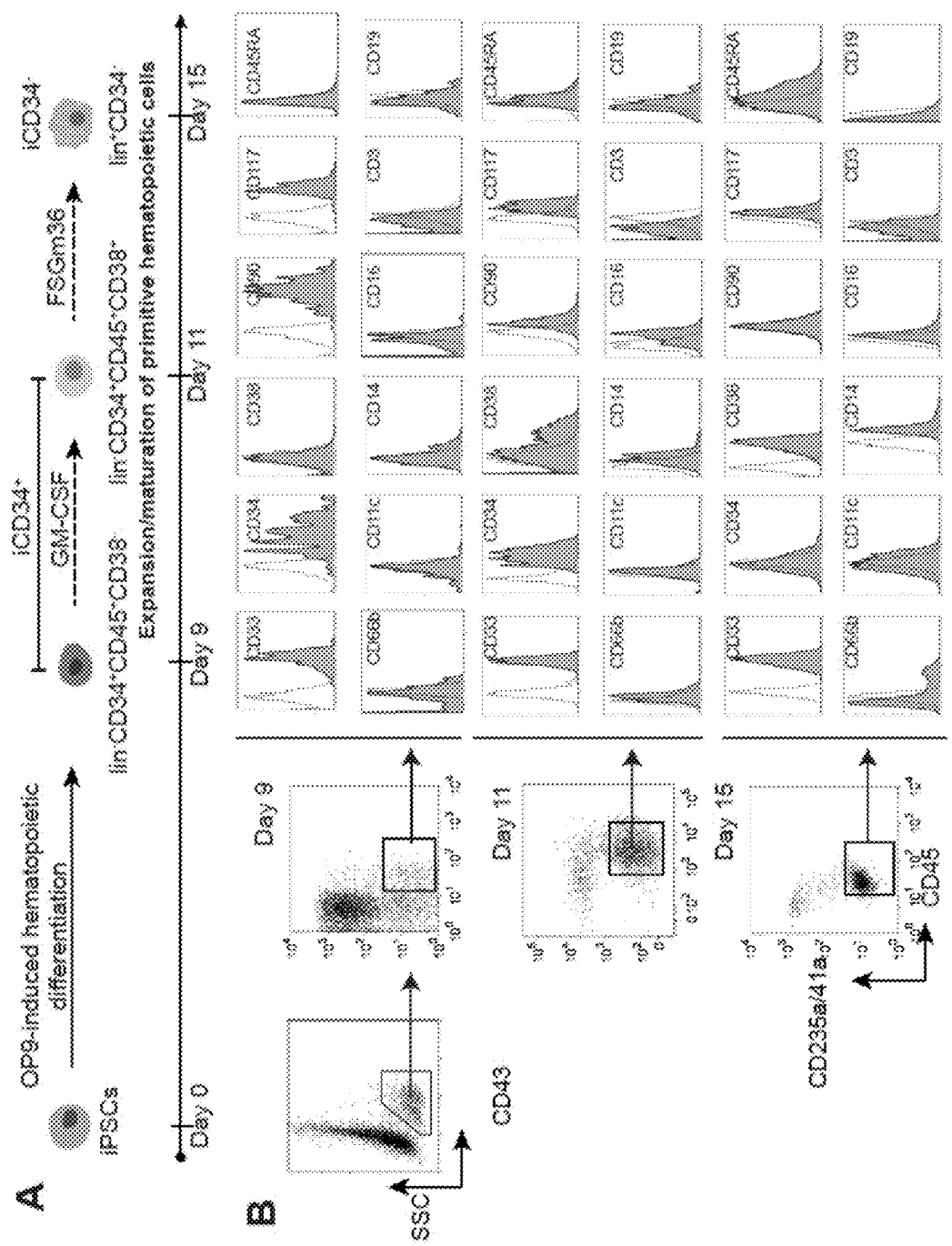
Fig. 1 A-B

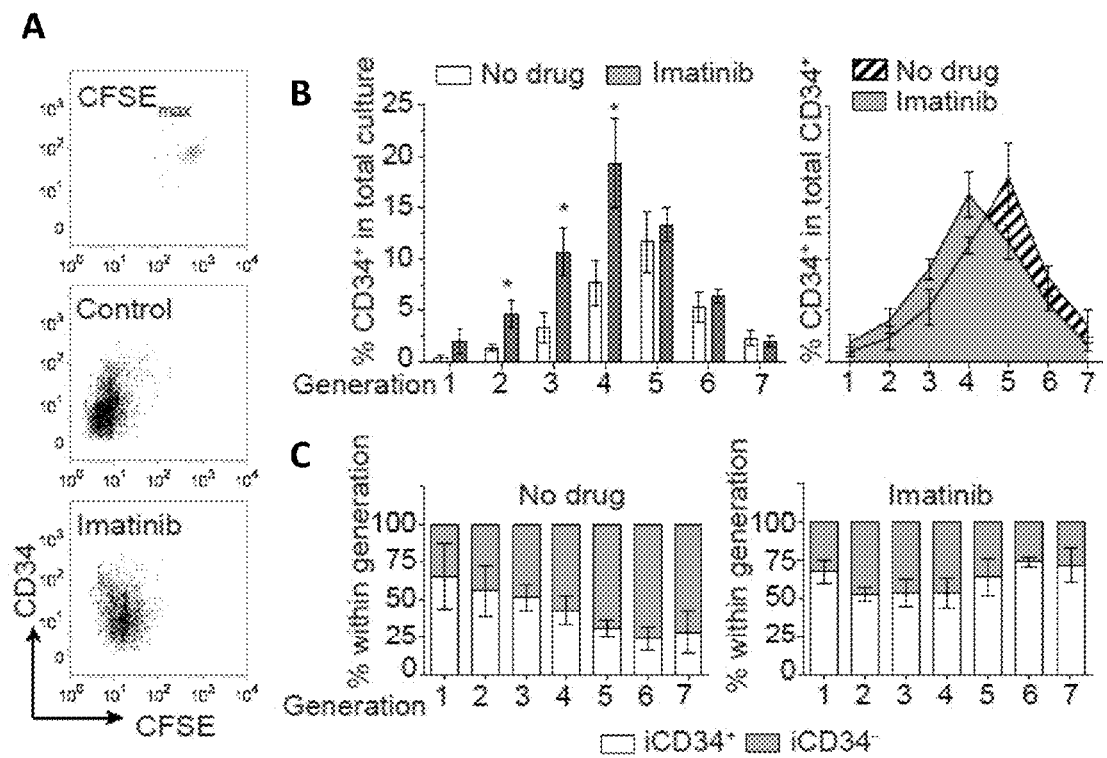
Fig. 4A-C

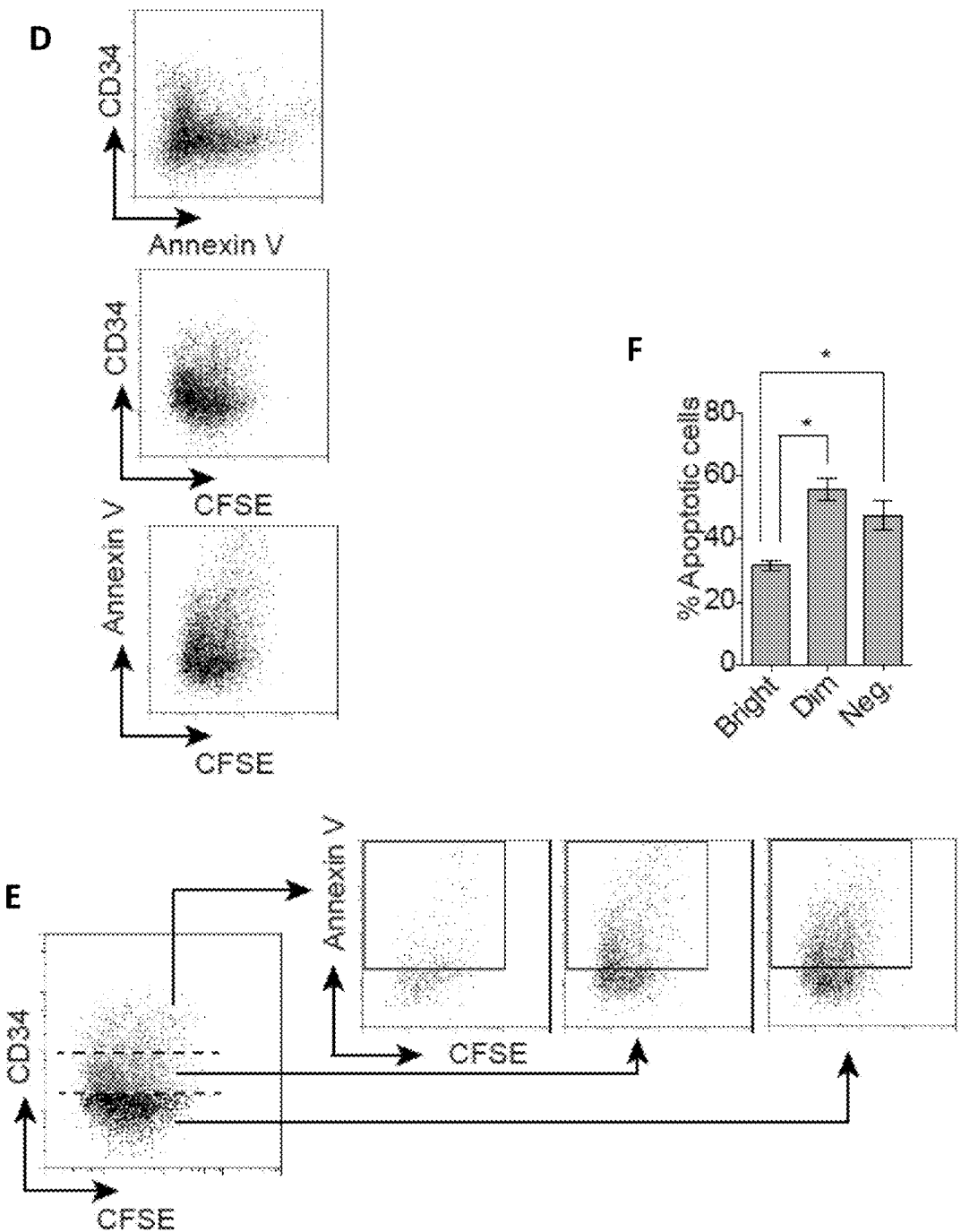
Fig. 4D-F

SEQUENCE LISTING

<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: self-designed specific primers for BCR-ABL - forward

<400> SEQUENCE: 1
acgttcctga tctcctctga ctatg         25

<210> SEQ ID NO 2
<211> LENGTH: 19
<212> TYPE: DNA
<213> ORGANISM: Artificial Sequence
<220> FEATURE:
<223> OTHER INFORMATION: self-designed specific primers for BCR-ABL - reverse

<400> SEQUENCE: 2
tcagaccctg aggctcaaa         19

<210> SEQ ID NO 3
<211> LENGTH: 21
<212> TYPE: DNA
<213> ORGANISM: Artificial Sequence
<220> FEATURE:
<223> OTHER INFORMATION: self-designed specific primers for OLFM4 -
      forward

<400> SEQUENCE: 3
ccagctggag gtggagataa g                                          21

<210> SEQ ID NO 4
<211> LENGTH: 20
<212> TYPE: DNA
<213> ORGANISM: Artificial Sequence
<220> FEATURE:
<223> OTHER INFORMATION: self-designed specific primers for OLFM4 -
      reverse

<400> SEQUENCE: 4
tcagagccac gatttctcgg                                            20

<210> SEQ ID NO 5
<211> LENGTH: 20
<212> TYPE: DNA
<213> ORGANISM: Artificial Sequence
<220> FEATURE:
<223> OTHER INFORMATION: self-designed specific primers for GAPDH -
      forward

<400> SEQUENCE: 5
gtggacctga cctgccgtct                                            20

<210> SEQ ID NO 6
<211> LENGTH: 20
<212> TYPE: DNA
<213> ORGANISM: Artificial Sequence
<220> FEATURE:
<223> OTHER INFORMATION: self-designed specific primers for GAPDH -
      reverse

<400> SEQUENCE: 6
ggaggagtgg gtgtcgctgt                                            20

<210> SEQ ID NO 7
<211> LENGTH: 2935
<212> TYPE: DNA
<213> ORGANISM: Homo sapiens

<400> SEQUENCE: 7
ttttcctaca tgctggccat ggggaaatca ccactgggca ctataagaag cccctgggct     60
ctctgcagag ccagcggctc cagctaagag acaagatga ggcccggcct ctcatttctc     120
ctagcccttc tgttcttcct tggccaagct gcagggatt tggggatgt gggacctcca     180 attcccagcc ccggcttcag ctctttccca ggtgttgact ccagctccag cttcagctcc    240
agctccaggt cgggctccag ctccagccgc agcttaggca gcggaggttc tgtgtcccag    300
ttgttttcca atttcaccgg ctccgtggat gaccgtggga cctgccagtg ctctgttttcc   360 ctgccagaca ccacctttcc cgtggacaga gtggaacgct tggaattcac agctcatgtt    420 cttttctcaga gtttgagaa agaactttcc aaagtgaggg aatatgtcca attaattagt    480
gtgtatgaaa agaaactgtt aaacctaact gtccgaattg acatcatgga gaaggatacc    540
atttcttaca ctgaactgga cttcgagctg atcaaggtag aagtgaagga gatggaaaaa    600

```
ctggtcatac agctgaagga gagttttggt ggaagctcag aaattgttga ccagctggag    660
gtggagataa gaaatatgac tctcttggta gagaagcttg agacactaga caaaaacaat    720
gtccttgcca ttcgccgaga atcgtggct ctgaagacca agctgaaaga gtgtgaggcc    780
tctaaagatc aaaacacccc tgtcgtccac cctcctccca ctccaggag ctgtggtcat    840 ggtggtgtgg tgaacatcag caaaccgtct gtggttcagc tcaactggag agggttttct    900
tatctatatg gtgcttgggg tagggattac tctccccagc atccaaacaa aggactgtat    960
tgggtggcgc cattgaatac agatgggaga ctgttggagt attatagact gtacaacaca   1020
ctggatgatt tgctattgta tataaatgct cgagagttgc ggatcaccta tggccaaggt   1080
agtggtacag cagtttacaa caacaacatg tacgtcaaca tgtacaacac cgggaatatt   1140
gccagagtta acctgaccac caacacgatt gctgtgactc aaactctccc taatgctgcc   1200
tataataacc gcttttcata tgctaatgtt gcttggcaag atattgactt tgctgtggat   1260
gagaatggat tgtgggttat ttattcaact gaagccagca ctggtaacat ggtgattagt   1320
aaactcaatg acaccacact tcaggtgcta aacacttggt ataccaagca gtataaacca   1380
tctgcttcta acgccttcat ggtatgtggg gttctgtatg ccacccgtac tatgaacacc   1440
agaacagaag agatttttta ctattatgac acaaacacag ggaagagggg caaactagac   1500
attgtaatgc ataagatgca ggaaaaagtg cagagcatta actataaccc ttttgaccag   1560
aaactttatg tctataacga tggttacctt ctgaattatg atctttctgt cttgcagaag   1620
ccccagtaag ctgtttagga gttagggtga agagaaaat gtttgttgaa aaaatagtct   1680
tctccactta cttagatatc tgcaggggtg tctaaaagtg tgttcatttt gcagcaatgt   1740
ttaggtgcat agttctacca cactagagat ctaggacatt tgtcttgatt tggtgagttc   1800
tcttgggaat catctgcctc ttcaggcgca ttttgcaata aagtctgtct agggtgggat   1860
tgtcagaggt ctaggggcac tgtgggccta gtgaagccta ctgtgaggag cttcactag   1920 aagccttaaa ttaggaatta aggaacttaa aactcagtat ggcgtctagg gattcttgt    1980 acaggaaata ttgcccaatg actagtcctc atccatgtag caccactaat tcttccatgc   2040
ctggaagaaa cctggggact tagttaggta gattaatatc tggagctcct cgagggacca   2100
aatctccaac tttttttcc cctcactagc acctggaatg atgctttgta tgtggcagat    2160
aagtaaattt ggcatgctta tatattctac atctgtaaag tgctgagttt tatggagaga   2220 ggcctttta tgcattaaat tgtacatggc aaataaatcc cagaaggatc tgtagatgag    2280
gcacctgctt tttcttttct ctcattgtcc accttactaa aagtcagtag aatcttctac   2340
ctcataactt ccttccaaag gcagctcaga agattagaac cagacttact aaccaattcc   2400 acccccacc aaccccttc tactgcctac tttaaaaaaa ttaatagttt tctatggaac    2460
tgatctaaga ttagaaaaat taattttctt taatttcatt atgaactttt atttacatga   2520
ctctaagact ataagaaaat ctgatggcag tgacaaagtg ctagcattta ttgttatcta   2580
ataaagacct tggagcatat gtgcaactta tgagtgtatc agttgttgca tgtaattttt   2640
gcctttgttt aagcctggaa cttgtaagaa aatgaaaatt taattttttt ttctaggacg   2700
agctatagaa aagctattga gagtatctag ttaatcagtg cagtagttgg aaaccttgct   2760
ggtgtatgtg atgtgcttct gtgcttttga atgactttat catctagtct tgtctatttt   2820
ttcctttgat gttcaagtcc tagtctatag gattggcagt ttaaatgctt tactccccct   2880
tttaaaataa atgattaaaa tgtgctttga aaaaagtcaa aaaaaaaaaa aaaaa        2935
```

```
<210> SEQ ID NO 8
<211> LENGTH: 510
<212> TYPE: PRT
<213> ORGANISM: Homo sapiens

<400> SEQUENCE: 8

Met Arg Pro Gly Leu Ser Phe Leu Leu Ala Leu Leu Phe Phe Leu Gly
1               5                   10                  15

Gln Ala Ala Gly Asp Leu Gly Asp Val Gly Pro Pro Ile Pro Ser Pro
            20                  25                  30

Gly Phe Ser Ser Phe Pro Gly Val Asp Ser Ser Ser Phe Ser Ser
            35                  40                  45

Ser Ser Arg Ser Gly Ser Ser Ser Arg Ser Leu Gly Ser Gly Gly
    50                  55                  60

Ser Val Ser Gln Leu Phe Ser Asn Phe Thr Gly Ser Val Asp Asp Arg
65                  70                  75                  80

Gly Thr Cys Gln Cys Ser Val Ser Leu Pro Asp Thr Thr Phe Pro Val
                85                  90                  95

Asp Arg Val Glu Arg Leu Glu Phe Thr Ala His Val Leu Ser Gln Lys
            100                 105                 110

Phe Glu Lys Glu Leu Ser Lys Val Arg Glu Tyr Val Gln Leu Ile Ser
            115                 120                 125

Val Tyr Glu Lys Lys Leu Leu Asn Leu Thr Val Arg Ile Asp Ile Met
130                 135                 140

Glu Lys Asp Thr Ile Ser Tyr Thr Glu Leu Asp Phe Glu Leu Ile Lys
145                 150                 155                 160

Val Glu Val Lys Glu Met Glu Lys Leu Val Ile Gln Leu Lys Glu Ser
                165                 170                 175

Phe Gly Gly Ser Ser Glu Ile Val Asp Gln Leu Glu Val Glu Ile Arg
            180                 185                 190

Asn Met Thr Leu Leu Val Glu Lys Leu Glu Thr Leu Asp Lys Asn Asn
            195                 200                 205

Val Leu Ala Ile Arg Arg Glu Ile Val Ala Leu Lys Thr Lys Leu Lys
    210                 215                 220

Glu Cys Glu Ala Ser Lys Asp Gln Asn Thr Pro Val Val His Pro Pro
225                 230                 235                 240

Pro Thr Pro Gly Ser Cys Gly His Gly Gly Val Val Asn Ile Ser Lys
                245                 250                 255

Pro Ser Val Val Gln Leu Asn Trp Arg Gly Phe Ser Tyr Leu Tyr Gly
            260                 265                 270

Ala Trp Gly Arg Asp Tyr Ser Pro Gln His Pro Asn Lys Gly Leu Tyr
            275                 280                 285

Trp Val Ala Pro Leu Asn Thr Asp Gly Arg Leu Leu Glu Tyr Tyr Arg
290                 295                 300

Leu Tyr Asn Thr Leu Asp Asp Leu Leu Leu Tyr Ile Asn Ala Arg Glu
305                 310                 315                 320

Leu Arg Ile Thr Tyr Gly Gln Gly Ser Gly Thr Ala Val Tyr Asn Asn
                325                 330                 335

Asn Met Tyr Val Asn Met Tyr Asn Thr Gly Asn Ile Ala Arg Val Asn
            340                 345                 350

Leu Thr Thr Asn Thr Ile Ala Val Thr Gln Thr Leu Pro Asn Ala Ala
            355                 360                 365

Tyr Asn Asn Arg Phe Ser Tyr Ala Asn Val Ala Trp Gln Asp Ile Asp
370                 375                 380
```

```
Phe Ala Val Asp Glu Asn Gly Leu Trp Val Ile Tyr Ser Thr Glu Ala
385                 390                 395                 400

Ser Thr Gly Asn Met Val Ile Ser Lys Leu Asn Asp Thr Thr Leu Gln
            405                 410                 415

Val Leu Asn Thr Trp Tyr Thr Lys Gln Tyr Lys Pro Ser Ala Ser Asn
            420                 425                 430

Ala Phe Met Val Cys Gly Val Leu Tyr Ala Thr Arg Thr Met Asn Thr
            435                 440                 445

Arg Thr Glu Glu Ile Phe Tyr Tyr Tyr Asp Thr Asn Thr Gly Lys Glu
            450                 455                 460

Gly Lys Leu Asp Ile Val Met His Lys Met Gln Glu Lys Val Gln Ser
465                 470                 475                 480

Ile Asn Tyr Asn Pro Phe Asp Gln Lys Leu Tyr Val Tyr Asn Asp Gly
            485                 490                 495

Tyr Leu Leu Asn Tyr Asp Leu Ser Val Leu Gln Lys Pro Gln
            500                 505                 510

<210> SEQ ID NO 9
<211> LENGTH: 490
<212> TYPE: PRT
<213> ORGANISM: Homo sapiens

<400> SEQUENCE: 9

Asp Leu Gly Asp Val Gly Pro Pro Ile Pro Ser Pro Gly Phe Ser Ser
1               5                   10                  15

Phe Pro Gly Val Asp Ser Ser Ser Phe Ser Ser Ser Arg Ser
            20                  25                  30

Gly Ser Ser Ser Arg Ser Leu Gly Ser Gly Ser Val Ser Gln
        35                  40                  45

Leu Phe Ser Asn Phe Thr Gly Ser Val Asp Asp Arg Gly Thr Cys Gln
    50                  55                  60

Cys Ser Val Ser Leu Pro Asp Thr Thr Phe Pro Val Asp Arg Val Glu
65                  70                  75                  80

Arg Leu Glu Phe Thr Ala His Val Leu Ser Gln Lys Phe Glu Lys Glu
                85                  90                  95

Leu Ser Lys Val Arg Glu Tyr Val Gln Leu Ile Ser Val Tyr Glu Lys
                100                 105                 110

Lys Leu Leu Asn Leu Thr Val Arg Ile Asp Ile Met Glu Lys Asp Thr
            115                 120                 125

Ile Ser Tyr Thr Glu Leu Asp Phe Glu Leu Ile Lys Val Glu Val Lys
    130                 135                 140

Glu Met Glu Lys Leu Val Ile Gln Leu Lys Glu Ser Phe Gly Gly Ser
145                 150                 155                 160

Ser Glu Ile Val Asp Gln Leu Glu Val Glu Ile Arg Asn Met Thr Leu
                165                 170                 175

Leu Val Glu Lys Leu Glu Thr Leu Asp Lys Asn Asn Val Leu Ala Ile
                180                 185                 190

Arg Arg Glu Ile Val Ala Leu Lys Thr Lys Leu Lys Glu Cys Glu Ala
            195                 200                 205

Ser Lys Asp Gln Asn Thr Pro Val Val His Pro Pro Thr Pro Gly
    210                 215                 220

Ser Cys Gly His Gly Val Val Asn Ile Ser Lys Pro Ser Val Val
225                 230                 235                 240

Gln Leu Asn Trp Arg Gly Phe Ser Tyr Leu Tyr Gly Ala Trp Gly Arg
                245                 250                 255
```

```
Asp Tyr Ser Pro Gln His Pro Asn Lys Gly Leu Tyr Trp Val Ala Pro
            260                 265                 270
Leu Asn Thr Asp Gly Arg Leu Leu Glu Tyr Tyr Arg Leu Tyr Asn Thr
            275                 280                 285
Leu Asp Asp Leu Leu Leu Tyr Ile Asn Ala Arg Glu Leu Arg Ile Thr
            290                 295                 300
Tyr Gly Gln Gly Ser Gly Thr Ala Val Tyr Asn Asn Asn Met Tyr Val
305                 310                 315                 320
Asn Met Tyr Asn Thr Gly Asn Ile Ala Arg Val Asn Leu Thr Thr Asn
                325                 330                 335
Thr Ile Ala Val Thr Gln Thr Leu Pro Asn Ala Ala Tyr Asn Asn Arg
            340                 345                 350
Phe Ser Tyr Ala Asn Val Ala Trp Gln Asp Ile Asp Phe Ala Val Asp
            355                 360                 365
Glu Asn Gly Leu Trp Val Ile Tyr Ser Thr Glu Ala Ser Thr Gly Asn
    370                 375                 380
Met Val Ile Ser Lys Leu Asn Asp Thr Thr Leu Gln Val Leu Asn Thr
385                 390                 395                 400
Trp Tyr Thr Lys Gln Tyr Lys Pro Ser Ala Ser Asn Ala Phe Met Val
            405                 410                 415
Cys Gly Val Leu Tyr Ala Thr Arg Thr Met Asn Thr Arg Thr Glu Glu
            420                 425                 430
Ile Phe Tyr Tyr Tyr Asp Thr Asn Thr Gly Lys Glu Gly Lys Leu Asp
            435                 440                 445
Ile Val Met His Lys Met Gln Glu Lys Val Gln Ser Ile Asn Tyr Asn
    450                 455                 460
Pro Phe Asp Gln Lys Leu Tyr Val Tyr Asn Asp Gly Tyr Leu Leu Asn
465                 470                 475                 480
Tyr Asp Leu Ser Val Leu Gln Lys Pro Gln
                485                 490
```

INDUCED PLURIPOTENT STEM CELL MODEL OF CHRONIC MYELOID LEUKEMIA REVEALED OLFACTOMEDIN 4 AS A NOVEL THERAPEUTIC TARGET IN LEUKEMIA STEM CELLS

CROSS REFERENCE TO RELATED APPLICATIONS

This application claims the benefit of U.S. Provisional Patent Application Ser. No. 61/812,014 filed on Apr. 15, 2013, which is incorporated by reference herein in its entirety.

STATEMENT REGARDING FEDERALLY SPONSORED RESEARCH OR DEVELOPMENT

This invention was made with government support under GM081629 and HL099773 awarded by the National Institutes of Health. The government has certain rights in the invention.

BACKGROUND

Chronic myeloid leukemia (CML) is a myeloproliferative disorder characterized by unregulated growth of predominantly myeloid cells and their accumulation in the bone marrow and peripheral blood. Generally, CML originates in hematopoietic stem cells (HSGs) with t(9;22)(q34;q11.2) translocation which produces BCR-ABL constitutively active kinase driving the expansion of leukemic progeny. The definitive cure of leukemia requires identification of novel therapeutic targets to eradicate leukemia stem cells (LSCS). However, rarity of LSCS within the pool of malignant cells remains major limiting factor for their study in humans.

Reprogramming somatic cells to pluripotency allows for generation of induced pluripotent stem cells (iPSCs) which behave similar to embryonic stem cells (ESCs), i.e. they are capable of self-renewal, large scale expansion, and differentiation toward derivatives of all three germ layers, including blood. Because iPSCs capture the entire genome of diseased cell they may be used successfully to model human genetic diseases.

BRIEF SUMMARY

Disclosed herein are compositions and methods to treat and reduce therapeutic resistance in chronic myelogenous leukemia. Also disclosed herein are methods to generate leukemia stem cell like cells (iLSCs) generated from CML patient-derived iPSCs, and methods for utilizing iLSCs in screens to identify modulators of CML drug resistance and gene targets that underlie CML drug resistance.

Accordingly in one aspect provided herein is a kit for treatment of CML, comprising therapeutically effective doses of a tyrosine kinase inhibitor and an inhibitor of a gene target selected from the group consisting of OLFM4, HLA-DRB, GPNMB, OLR1, HLA-DRA, ACP5, C3, TLR8, APOE, FPR3, RBP7, CYP27A1, TPSB2, PLEKHG5, ABCG1, MS4A7, SULF2, SLC11A1, CCL13, LGALS3, LRP1, GRN, SLAMF8, HLA-DMB, COLEC12, ALOX5AP, IL4I1, CEACAM8, C19orf59, IFI30, FCGR2c, SLCO2B1, C1 QB, CCL20, CXCL16, CHI3L1, FBP1, ALDH2, SLC15A3, LILRB5, TM6SF1, RETN, CLEC4A, BCL2A1, ARHGEF10L, NDFIP2, CAPG, SLC8A1, C1QA, HLA-DPA1, STAG, DPYD, HLA-DMA, LGMN, SEMA6B, TNFSF12, MAL, COL8A2, ITGAX, IL9R, MATN2, SLC7A7, KYNU, APOC1, BTG2, C3AR1, CTSS, ALOX15, HLA-B, GIMAP8, TUBA1A, DNASE2, CD2, SBF2, CD68, BMF, S100A10, TBC1D2, SLC37A2, BHLHE40, RTN1, CEACAM1, FLVCR2, CCDC92, FCGR2B, MILR1, LY86, FOLR2, CLEC12A, PLD2, AHNAK, CEACAM4, CD300LF, CTSH, NCF1, S100A6, ADAMDEC1, PILRA, SMAD7, PMP22, TYROBP, NPC2, NLRC4, LGALS1, RNF19B, OSCAR, ALOX5, CST3, DENND2D, NPL, ASAH1, LAPTM5, MYO7B, TRIM22, PPARG, GIMAP1-GIMAP5, RENBP, PREX1, CD52, C4orf34, SAMHD1, HK3, QPCT, GADD45G, CEACAM21, TBX3, SORL1, INSIG1, SIGLEC6, CD38, TP531NP1, NCOA3, FILIP1L, NAPSA, SKIL, and TCN1.

In some embodiments the inhibitor inhibits a gene target selected from the group consisting of OLFM4 (GenBank NM_006418.4), CEACAM4 (GenBank NM_001817), CEACAM8 (GenBank NM_001816.3), CEACAM1 (GenBank NM_001712.4), ALOX15 (GenBank NM_001140.3), CLEC12A (GenBank NM_138337.5), HK3 (GenBank NM_002115.2), CLEC4A (GenBank NM_016184.3), CTSS (GenBank NM_004079.4), and TNFSF12 (GenBank NM_003809.2).

In some embodiments the gene target inhibitor comprises an siRNA against the gene target mRNA, a knock-down vector against the gene target mRNA, or an antibody against a protein encoded by the gene target.

In some embodiments the gene target is OLFM4. In some embodiments the tyrosine kinase inhibitor included in the kit is selected from the group consisting of imatinib, nilotinib, dasatinib, bosutinib, ponatinib, bafetinib and saracatinib. In some embodiments the tyrosine kinase inhibitor included in the kit is a tyrosine kinase inhibitor that inhibits BCR-ABL tyrosine kinase. In some embodiments the tyrosine kinase inhibitor is imatinib.

In another aspect provided herein is a pharmaceutical composition for treatment of CML comprising a pharmaceutically acceptable excipient, and therapeutically effective amounts of a tyrosine kinase inhibitor and an inhibitor of a gene target selected from the group consisting of OLFM4, HLA-DRB, GPNMB, OLR1, HLA-DRA, ACP5, C3, TLR8, APOE, FPR3, RBP7, CYP27A1, TPSB2, PLEKHG5, ABCG1, MS4A7, SULF2, SLC11A1, CCL13, LGALS3, LRP1, GRN, SLAMF8, HLA-DMB, COLEC12, ALOX5AP, IL4I1, CEACAM8, C19orf59, IFI30, FCGR2c, SLCO2B1, C1 QB, CCL20, CXCL16, CHI3L1, FBP1, ALDH2, SLC15A3, LILRB5, TM6SF1, RETN, CLEC4A, BCL2A1, ARHGEF10L, NDFIP2, CAPG, SLC8A1, C1QA, HLA-DPA1, STAG, DPYD, HLA-DMA, LGMN, SEMA6B, TNFSF12, MAL, COL8A2, ITGAX, IL9R, MATN2, SLC7A7, KYNU, APOC1, BTG2, C3AR1, CTSS, ALOX15, HLA-B, GIMAP8, TUBA1A, DNASE2, CD2, SBF2, CD68, BMF, S100A10, TBC1D2, SLC37A2, BHLHE40, RTN1, CEACAM1, FLVCR2, CCDC92, FCGR2B, MILR1, LY86, FOLR2, CLEC12A, PLD2, AHNAK, CEACAM4, CD300LF, CTSH, NCF1, S100A6, ADAMDEC1, PILRA, SMAD7, PMP22, TYROBP, NPC2, NLRC4, LGALS1, RNF19B, OSCAR, ALOX5, CST3, DENND2D, NPL, ASAH1, LAPTM5, MYO7B, TRIM22, PPARG, GIMAP1-GIMAP5, RENBP, PREX1, CD52, C4orf34, SAMHD1, HK3, QPCT, GADD45G, CEACAM21, TBX3, SORL1, INSIG1, SIGLEC6, CD38, TP531NP1, NCOA3, FILIP1L, NAPSA, SKIL, and TCN1.

In some embodiments the inhibitor inhibits a gene target selected from the group consisting of OLFM4 (GenBank NM_006418.4), CEACAM4 (GenBank NM_001817), CEACAM8 (GenBank NM_001816.3), CEACAM1 (GenBank NM_001712.4), ALOX15 (GenBank NM_001140.3), CLEC12A (GenBank NM_138337.5), HK3 (GenBank NM_002115.2), CLEC4A (GenBank NM_016184.3), CTSS (GenBank NM_004079.4), and TNFSF12 (GenBank NM_003809.2).

In some embodiments the tyrosine kinase inhibitor included in the pharmaceutical composition inhibits BCR-ABL tyrosine kinase. In some embodiments the tyrosine kinase inhibitor is imatinib. In some embodiments the gene target is OLFM4. In some embodiments the tyrosine kinase inhibitor is imatinib and the gene target is OLFM4. In some embodiments the tyrosine kinase inhibitor is imatinib and the inhibitor of the gene target comprises an OLFM4 siRNA. In other embodiments the tyrosine kinase inhibitor is imatinib and the inhibitor of the gene target comprises an anti-OLFM4 antibody.

In another aspect provided herein is a method for treating CML comprising administering to a subject in need thereof a therapeutically effective amount of an inhibitor of a gene target, or gene target product thereof, selected from the group consisting of OLFM4, HLA-DRB, GPNMB, OLR1, HLA-DRA, ACP5, C3, TLR8, APOE, FPR3, RBP7, CYP27A1, TPSB2, PLEKHG5, ABCG1, MS4A7, SULF2, SLC11A1, CCL13, LGALS3, LRP1, GRN, SLAMF8, HLA-DMB, COLEC12, ALOX5AP, IL4I1, CEACAM8, C19orf59, IFI30, FCGR2c, SLCO2B1, C1QB, CCL20, CXCL16, CHI3L1, FBP1, ALDH2, SLC15A3, LILRB5, TM6SF1, RETN, CLEC4A, BCL2A1, ARHGEF10L, NDFIP2, CAPG, SLC8A1, C1QA, HLA-DPA1, STAG, DPYD, HLA-DMA, LGMN, SEMA6B, TNFSF12, MAL, COL8A2, ITGAX, IL9R, MATN2, SLC7A7, KYNU, APOC1, BTG2, C3AR1, CTSS, ALOX15, HLA-B, GIMAP8, TUBA1A, DNASE2, CD2, SBF2, CD68, BMF, S100A10, TBC1D2, SLC37A2, BHLHE40, RTN1, CEACAM1, FLVCR2, CCDC92, FCGR2B, MILR1, LY86, FOLR2, CLEC12A, PLD2, AHNAK, CEACAM4, CD300LF, CTSH, NCF1, S100A6, ADAMDEC1, PILRA, SMAD7, PMP22, TYROBP, NPC2, NLRC4, LGALS1, RNF19B, OSCAR, ALOX5, CST3, DENND2D, NPL, ASAH1, LAPTM5, MYO7B, TRIM22, PPARG, GIMAP1-GIMAP5, RENBP, PREX1, CD52, C4orf34, SAMHD1, HK3, QPCT, GADD45G, CEACAM21, TBX3, SORL1, INSIG1, SIGLEC6, CD38, TP531NP1, NCOA3, FILIP1L, NAPSA, SKIL, and TCN1.

In some embodiments of the method, the gene target inhibitor comprises an siRNA against the gene target, an RNAi expression vector against the gene target mRNA, or an antibody against the gene target protein. In some embodiments of the method, the gene target to be inhibited is OLM4. In some embodiments the OLFM4 inhibitor comprises an siRNA against OLM4 mRNA, an RNAi expression vector against OLM4 mRNA, or an antibody against OLM4 protein. In some embodiments the OLFM4 inhibitor comprises an antibody against OLFM4 protein. In other embodiments the OLFM4 inhibitor comprises an siRNA against OLFM4 mRNA.

In some embodiments the treatment method also includes administering a therapeutically effective amount of a tyrosine kinase inhibitor. In some embodiments the tyrosine kinase inhibitor inhibits BCR-ABL tyrosine kinase. In some embodiments the tyrosine kinase inhibitor is selected from the group consisting of imatinib, nilotinib, dasatinib, bosutinib, ponatinib, bafetinib and saracatinib. In some embodiments the tyrosine kinase inhibitor to be administered is imatinib. In some embodiments administration of the OLFM4 inhibitor and the tyrosine kinase inhibitor is concurrent. In other embodiments administration of the tyrosine kinase inhibitor precedes administration of the gene target inhibitor (e.g., an inhibitor of OLFM4).

In another aspect provided herein is a method for treating CML comprising administering to a subject in need thereof a therapeutically effective amount of an activator of a gene target selected from the group consisting of: BMP2, TERT, DUSP2, MDK, ACTL8, MDFI, CHCHD2, GJA1, CPXM1, ARHGAP22, NYNRIN, PACSIN3, GALNT14, and PODXL2.

In yet another aspect provided herein is a method of identifying a modulator of CML drug resistance, comprising the steps of: (i) culturing induced leukemia stem cell-like cells (iLSCs) with a CML drug in the presence or absence of a test agent; (ii) determining the level of apoptosis of the iLSCs after step (i); and (iii) identifying the test agent as a modulator of resistance to the CML drug if the level of proliferation in the presence of the test agent differs from the level of proliferation in the absence of the test agent. In some embodiments the method further comprises (iv) determining a level of apoptosis in normal iCD4+ cells cultured with a CML drug in the presence or absence of the test agent; and (v) comparing the level of apoptosis determined in step (ii) with the level of apoptosis determined in step (v).

In some embodiments the CML drug used in the just mentioned screening method is a tyrosine kinase inhibitor. In some embodiments the tyrosine kinase inhibitor is selected from the group consisting of imatinib, nilotinib, dasatinib, bosutinib, ponatinib, bafetinib and saracatinib. In some embodiments the tyrosine kinase inhibitor is imatinib. In some embodiments step (ii) of the method also includes determining the level of proliferation of the iLSCs in the presence and absence of the drug.

In a related aspect provided herein is a method of identifying a candidate gene target that confers drug resistance in chronic myeloid leukemia (CML), comprising: (i) culturing induced leukemia stem cell-like cells (iLSCs) in the presence or absence of a drug for treatment of CML; (ii) determining gene expression profiles in the iLSCs cultured in the presence of the drug and in iLSCs cultured in the absence of the drug; and (iii) identifying genes that are expressed at different levels in the iLSCs cultured in the presence versus the absence of the drug as a candidate gene target that confers resistance to the drug.

In some embodiments the method further comprises (iv) identifying genes that are expressed at different levels in iLSCs in the presence versus the absence of the CML drug, but are not expressed at different levels in normal iCD4+ cells cultured in the presence versus the absence of the CML drug.

In some embodiments the drug to be used in the screening method is a tyrosine kinase inhibitor (e.g., imatinib). In some embodiments the determining step in (ii) comprises determining the expression level of gene selected from the group consisting of OLFM4, HLA-DRB, GPNMB, OLR1, HLA-DRA, ACP5, C3, TLR8, APOE, FPR3, RBP7, CYP27A1, TPSB2, PLEKHG5, ABCG1, MS4A7, SULF2, SLC11A1, CCL13, LGALS3, LRP1, GRN, SLAMF8, HLA-DMB, COLEC12, ALOX5AP, IL4I1, CEACAM8, C19orf59, IFI30, FCGR2c, SLCO2B1, C1QB, CCL20, CXCL16, CHI3L1, FBP1, ALDH2, SLC15A3, LILRB5, TM6SF1, RETN, CLEC4A, BCL2A1, ARHGEF10L, NDFIP2, CAPG, SLC8A1, C1QA, HLA-DPA1, STAG, DPYD, HLA-DMA, LGMN, SEMA6B, TNFSF12, MAL, COL8A2, ITGAX, IL9R, MATN2, SLC7A7, KYNU, APOC1, BTG2, C3AR1, CTSS, ALOX15, HLA-B, GIMAP8, TUBA1A, DNASE2, CD2, SBF2, CD68, BMF, S100A10, TBC1D2, SLC37A2, BHLHE40, RTN1, CEACAM1, FLVCR2, CCDC92, FCGR2B, MILR1, LY86, FOLR2, CLEC12A, PLD2, AHNAK, CEACAM4, CD300LF, CTSH, NCF1, S100A6, ADAMDEC1, PILRA, SMAD7, PMP22, TYROBP, NPC2, NLRC4, LGALS1, RNF19B, OSCAR, ALOX5, CST3, DENND2D, NPL, ASAH1, LAPTM5, MYO7B, TRIM22, PPARG, GIMAP1-GIMAP5, RENBP, PREX1, CD52, C4orf34, SAMHD1, HK3, QPCT, GADD45G, CEACAM21, TBX3, SORL1, INSIG1, SIGLEC6, CD38, TP531NP1, NCOA3, FILIP1L, NAPSA, SKIL, TCN1 BMP2, TERT, DUSP2, MDK, ACTL8, MDFI, CHCHD2, GJA1, CPXM1, ARHGAP22, NYNRIN, PACSIN3, GALNT14, and PODXL2.

In a further aspect provided herein is a method of identifying a candidate therapeutic agent for treating CML, comprising the steps of: (i) culturing induced leukemia stem cell-like cells (iLSCs) in the presence or absence of a test agent; (ii) measuring apoptosis of the iLSCs after step (i); and (iii) identifying the test agent as a candidate CML therapeutic agent if the level of apoptosis in the presence of the test agent is higher than the level of apoptosis in the absence of the test agent.

In yet another aspect provided herein is a method of generating induced leukemia stem cell-like cells (iLSCs), comprising: (a) obtaining cells from a chronic myeloid leukemia (CML) patient; (b) reprogramming the cells to generate transgene-free induced pluripotent stem cells (iPSCs); (c) differentiating the iPSCs under conditions that produce $CD34^+$ $CD43^+$ hematopoietic progenitors; and (d) collecting $lin^-$ $CD34^+CD45^+$ primitive hematopoietic cells with leukemia stem cell (LSC) features.

In some embodiments the method includes the further step (e) of differentiating the $lin^-CD34^+CD45^+$ into $lin^+CD34^-$ hematopoietic cells. In some embodiments the differentiation step (c) comprises differentiation under defined conditions without the use of stromal cell co-culture.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

FIG. 4 CFSE tracking of CML and BM $iCD34^+$ cells after treatment with imatinib. (A) $iCD34^+$ cells were cultured with or without 5 µM imatinib for four days. Mitomycin C-treated cells were used to set the $CFSE_{max}$. Dot plot shows CD34 vs CFSE. (B) The distribution of $CD34^+$ cells within each generation in control and imatinib group. Left graph shows the percentage of $CD34^+$ cells within generations 1-7. Right graph shows the relative contribution of $CD34^+$ cells within each generation to the entire pool of $CD34^+$ cells in culture. The area under the curve represents 100% of $CD34^+$ cells. (C) The relative proportion of $CD34^+$ and $CD34^-$ cells within each generation in control and imatinib group. Bars show mean±SEM of three experiments. * $p<0.05$. (D) Dot plots show expression of CFSE, CD34 and annexin V by flow cytometry. (E) Flow cytometric analysis of apoptosis (7AAD-Annexin $V^+$) and CD34 expression at the end of 4 days expansion with and without 5 µM imatinib. (F) Histogram shows relative proportion of apoptotic cells within $CD34^{bright}$, $CD34^{dim}$, and $CD34^-$ (negative) population gated from left dot plot. Results are mean±SEM of 3 experiments. * $p<0.05$.

DETAILED DESCRIPTION

Figure 1C:
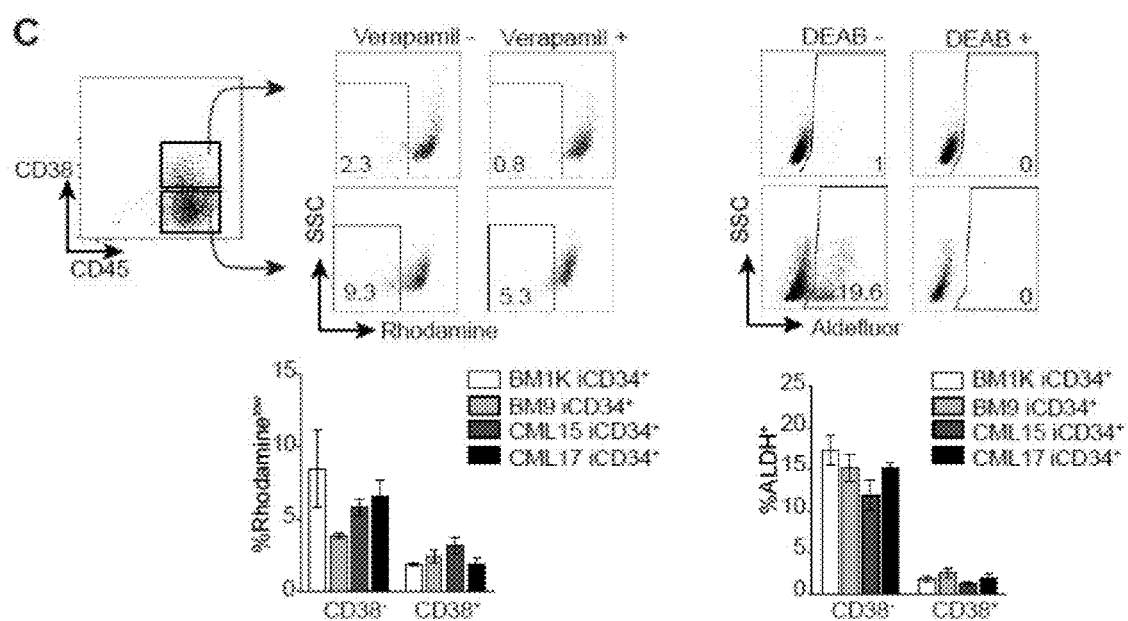
FIG. 1 Generation of $lin^-CD34^+CD43^+CD45^+$ primitive hematopoietic cells from CML-iPSCs. (A) Schematic diagram of hematopoietic differentiation from iPSCs. Phenotype and its designation are shown under and on the top of corresponding cells, respectively. Prefix i indicates iPSC-derived. FSGm36=Flt3L, SCF, GM-CSF, IL3, IL6. (B) Phenotypes of $CD45^+$ cells obtained from CML-iPSCs after differentiation on OP9 (day 9) and following their expansion/differentiation with cytokines in stroma-free cultures (as indicated in a). Representative results from three to four independent experiments are shown. (C) Rhodamine (Rho) efflux and ALDH activity in isolated CML $iCD34^+$ cells. Representative dot plots show RhO efflux and ALDH activity in $CD34^+$ $CD38^+$ and $CD34^+CD38^-$ populations. Graph under corresponding dot plot shows quantification of Rho efflux and ALDH assay. The values are mean±SEM of (% of $Rho^{low}_{verapamil-}$-$Rho^{low}_{verapamil+}$) and (% of $ALDH^+_{DEAB-}$-$ALDH^+_{DEAB+}$) from three experiments respectively. DEAB=diethylaminobenzaldehyde, ALDH=aldehyde dehydrogenase. See also FIG. 7.

Disclosed herein are methods and compositions relating to induced leukemia stem cell-like cells (iLSCs), which are generated by differentiation of induced pluripotent stem cells generated from patients suffering from chronic myeloid leukemia (CML).

A "gene target," as used herein refers to an RNA (e.g., a "gene target mRNA") or encoded protein expressed from a gene of interest ("gene target protein") or the gene itself.

An "inhibitor of a gene target," as used herein, refers to an agent that inhibits one or more biological functions linked to a specific gene target. For example, the inhibitor (e.g., an siRNA) may act by reducing the steady state level of a mRNA transcribed from the gene target (e.g., an siRNA), or the inhibitor (e.g., an antibody) may act by binding tightly to a critical epitope/domain on a protein encoded by the gene target. Alternatively, an inhibitor may be a small molecular weight compound (less than 900 Daltons) such as a competitive antagonist that interacts and inhibits an activity of a protein encoded by the gene target.

An "activator of a gene target," as used herein, refers to an agent that increases the activity of a biological function linked to a specific gene target. For the example the activator (e.g., a modified mRNA) may act by increasing the steady state level of translated gene target protein, or the gene target activator can simply be a recombinant form of the encoded gene target protein.

I. Methods

CML originates in hematopoietic stem cells (HSGs) with t(9;22)(q34;q11.2) translocation which produces BCR-ABL constitutively active kinase driving the expansion of leukemic progeny. Thus, since this translocation occurs specifically in this cell type, it is necessary to generate iPSCs from leukemia cells in order to obtain iPSCs that have the t(9;22)(q34;q11.2) translocation. The iPSCs that have this genetic lesion are used to differentiate into the blood and produce cells with LSC features identified by the similarity to somatic CML LSCs in a feature selected from the group consisting of lin-CD34+ CD38–CD45RA-CD90+CD117+ HSC phenotype, ALDH activity, ability to efflux rhodamine-123, LTC-IC potential, limited cytokine independent proliferation, defective adhesion to fibronectin, and intrinsic resistance to imatinib.

Generation of iPSCs and iLSCs from CML Patients

While in general hiPSCs can be generated from a wide variety of somatic cell types, hiPSCs for use in the methods and compositions described herein are generated by integration-free reprogramming of cell types carrying at least the t(9;22)(q34;q11.2) translocation, although they may include translocations in addition to the t(9;22)(q34;q11.2) translocation. Typically the cells used to generate hiPSCs described herein are bone marrow (BM) mononuclear cells isolated from a CML patient in the chronic phase of the disease, and hiPSCs are then generated as described in detail in Hu et al (2011), 117(14):e109-119.

CML-iPSCs can be maintained and passaged according to any of a number of standard methods in the art.

CML-iPSCs are then differentiated to obtain leukemia stem cell-like cells, referred to herein as induced leukemia stem cell-like cells (iLSCs). LSCs in CML ("CML-LSCs" or "LSCs") have been identified within the most primitive hematopoietic compartment as cells with long-term culture initiating cell (LTC-IC) or in vivo repopulating activities (Corbin et al., 2011; Li et al., 2012; Petzer et al., 1996; Sloma et al., 2010; Udomsakdi et al., 1992b). Similar to normal hematopoietic stem cells (HSGs), CML LSCs express markers of primitive hematopoietic cells including CD34, CD90, CD117 and are negative for hematopoietic lineage markers (lin$^-$) and CD45RA. CML LSCs also exhibit aldehyde dehydrogenase (ALDH) activity and the ability to efflux Rhodamine-123.

In some embodiments hematopoietic differentiation of CML-iPSCs is induced by transferring them to overgrown OP9 feeders described in detail (Choi et al., 2009a; Vodyanik et al., 2005) to obtain a population of CD34$^+$CD43$^+$ hematopoietic progenitors. CD43$^+$ cells are collected on day 9 of the co-culture differentiation using magnetic-activated cell sorting (MACS). This population includes a CD235a$^-$CD41a$^-$ CD45$^+$ subpopulation, which can be purified by fluorescence activated cell sorting, e.g., by labeling with CD235a-fluorescein (FITC), CD41a-fluorescein (FITC), CD45-allophycocyanin (APC), and CD38-phycoerythrin (PE). This subpopulation is highly enriched in myeloid progenitors, and displays the phenotypic features of CML-LSCs, e.g., they are lin$^-$ CD34$^+$CD38$^-$CD45$^+$CD45RA$^-$CD90$^+$CD117$^+$ similar to primitive hematopoietic stem cells. The cells are referred to herein as iCD34$^+$ cells when derived from either control iPSCs (BM-iCD34$^+$ cells) or CML-iPSCs (CML-iCD34$^+$ cells, also referred to herein as "iLSCs"). Similar to CML LSCs, the cells also have ALDH activity and the ability to efflux Rhodamine-123 (as shown in FIG. 1C).

In some embodiments the CD43$^+$ cell population obtained by co-culture with OP9 cells is then cultured, to expand the myeloid progenitor population, in complete serum supplemented medium (CSSM), which is α-MEM supplemented with 10% FBS, 50 µg/ml ascorbic acid, 100 µM monothioglycerol, and the CSSM is supplemented with 200 ng/ml GM-CSF to expand selectively myeloid progenitors. After expansion, CD45$^+$ cells retain expression of HSC markers and remain lin$^-$ and CD45RA$^-$, however some of them acquire expression of CD38 (e.g., as shown in FIG. 1B at day 11).

In other embodiments hematopoietic differentiation of CML-iPSCs is done under defined conditions, i.e., without the need for stromal cell co-culture or serum as described in detail in U.S. non-provisional patent application Ser. No. 14/206,778 filed on Mar. 12, 2014. Such co-culture free embodiments include the steps of (a) providing human pluripotent stem cells (e.g., human embryonic stem cells (hESCs) or human induced pluripotent stem cells (hiPSCs)) and (b) culturing the human pluripotent stem cells under hypoxic condition (3-10% O$_2$) in a cell culture medium comprising FGF2, BMP4, Activin A, and LiCl for a period of about two days to form a cell population of $^{EMH}$lin-KDR$^+$APLNR$^+$ PDGFRalpha$^+$ primitive mesoderm cells with mesenchymoangioblast potential. Afterwards, the method includes a further step (c) culturing, under hypoxic conditions, the cell population obtained in step (b) in a cell culture medium comprising FGF2 and VEGF for a period of about 1-2 days to obtain a cell population comprising $^{EMH}$lin$^-$KDR$^+$APLNR$^+$ PDGFRalpha$^+$ primitive mesoderm with hemangioblast (HB-CFC) potential and hematovascular mesoderm cells ($^{EMH}$lin$^-$KDR$^{hi}$APLNR$^+$PDGFRalpha$^{lo/-}$) enriched in cells with a potential to form hematoendothelial clusters when cultured on OP9 cells. Subsequently, in step (d), the hematovascular mesoderm cells of step (c) are cultured under hypoxic conditions, in a cell culture medium comprising FGF2, VEGF, IL6, SCF, TPO, and IL3 for about one day to achieve formation of CD144$^+$CD73$^+$CD235a/CD43$^-$ non-hemogenic endothelial progenitors (non-HEP), CD144$^+$ CD73$^-$CD235a/CD43$^-$ hemogenic endothelial progenitors (HEPs), CD144$^+$CD73$^-$CD235a/CD43$^+$41a$^-$ angiogenic hematopoietic progenitors (AHP), and CD43$^+$CD41a$^+$ hematopoietic progenitor cells. Finally, in step (e), the HEPs and hematopoietic progenitor cells obtained in step (d) are cultured, under normoxia, in a culture medium comprising FGF2, VEGF, IL6, SCF, TPO, IL3 for about three days to obtain an expanded population of CD43$^+$ hematopoietic progenitors comprising CD43$^+$CD235a$^+$CD41a$^+$ erythromegakaryocytic progenitors and lin$^-$CD34$^+$CD45$^+$ with LSC features. The linCD34$^+$CD45$^+$ iLSC subpopulation can then be isolated from the multipotent hematopoietic progenitor population as described above. In some embodiments of the just-described differentiation method, the human pluripotent stem cells are plated at an initial density of about 5000 cells/cm$^2$ to about 15,000 cells/cm$^2$, e.g., 6000 cells/cm$^2$, 7000 cells/cm$^2$, 8000 cells/cm$^2$, 9000 cells/cm$^2$, or another plating density from about 5000 cells/cm$^2$ to about 15,000 cells/cm$^2$. Preferably, the human pluripotent stem cells are cultured without formation of embryoid bodies.

In addition to the detection of iLSCs by the presence of specific surface marker combinations, they can also be confirmed by growth-based assays such as the long-term culture initiating cell (LTC-IC) assay, which, measures primitive hematopoietic stem cells based on their capacity to produce myeloid progeny for at least 5 weeks. In such an assay, iLSCs produce a much higher number of LTC-IC derived colony forming cells as compared to HSCs generated from control subject-derived iPSCs.

Screening Assays

A number of drugs for the treatment of CML are known (e.g., BCL-ABL tyrosine kinase inhibitors such as imatinib), which target LSCs, the overproliferation of which drive disease progression. Unfortunately, the long term efficacy of such drugs in inhibiting proliferation of LSCs is frequently hampered by adaptive resistance of these cells to such drugs. Thus, the availability of the iLSCs enable the search for agents and gene targets that can modulate drug resistance in LSCs. iLSCs capture the entire genome of neoplastic cells and provide a unique opportunity to evaluate drug resistance in individual patients without a constant need to obtain new bone marrow biopsies. Accordingly, described herein are methods for identifying a modulator of CML drug resistance, which includes the steps of: (i) culturing induced leukemia stem cell-like cells (iLSCs) with a CML drug in the presence or absence of a test agent; (ii) measuring apoptosis of the iLSCs after step (i); and (iii) identifying the test agent as a modulator of resistance to the CML drug if the level of proliferation in the presence of the test agent differs from the level of proliferation in the absence of the test agent.

Also contemplated herein are screening assays to identify candidate therapeutic agents for treating CML, where the screening assay includes the steps of: (i) culturing induced leukemia stem cell-like cells (iLSCs) in the presence or absence of a test agent; (ii) measuring apoptosis of the iLSCs after step (i); and (iii) identifying the test agent as a candidate CML therapeutic agent if the level of apoptosis in the presence of the test agent is higher than the level of apoptosis in the absence of the test agent.

In some embodiments the LSCs to be assessed for apoptosis are cultured in CSSM supplemented with 10 ng/ml IL3, 100 ng/ml IL6, 200 ng/ml GM-CSF, 100 ng/ml SCF, and 100 ng/ml Flt3L, a CML drug, and in the presence or absence of a test agent. In some cases, where the LSCs are not cultured in the presence of a test agent, the cells are, nevertheless, cultured in the presence of a drug vehicle, e.g., DMSO (e.g., 0.1% DMSO). Alternatively, neither a test agent or a drug vehicle are added to the culture medium. In some embodiments LSCs are cultured with the CML drug in the presence or absence of the test agent prior to the apoptosis assay for a period of at least 12 hours to about 48 hours, e.g., 14 hours, 16 hours, 18 hours, 24 hours, 30 hours, 36 hours, 40 hours, or another period from at least 12 hours to about 48 hours.

Methods for assaying apoptosis are well known in the art. In an exemplary embodiment the apoptosis assay to be used is a quantitative Annexin V binding assay (e.g., carried out using the PE Annexin V Apoptosis Detection Kit I™ from 7-aminoactinomycin D (7-AAD), a vital dye which is excluded from cells with intact membranes. Subsequently staining is quantified by flow cytometry to determine the percentage of Annexin-V$^+$ and 7-AAD$^+$ cells in an LSC population. In some embodiments, the method may also include determining a level of cell proliferation, e.g., by counting the number of LSCs that are Annexin$^-$ 7-AAD$^-$ (i.e., viable) cells in the just mentioned apoptosis assay. Alternatively, apopoptosis can be detected by labeling active caspases inside apoptotic cells, using TUNEL assay, or any other assays to detect apoptotic assay.

In some embodiments the CML drug to be used in this method is a tyrosine kinase inhibitor. Such tyrosine kinase inhibitors include, but are not limited to, imatinib (4-[(4-methylpiperazin-1-yl)methyl]-N-(4-methyl-3-{[4-(pyridin-3-yl)pyrimidin-2-yl]amino}phenyl)benzamide); nimotinib (4-methyl-N-[3-(4-methyl-1H-imidazol-1-yl)-5-(trifluoromethyl)phenyl]-3-[(4-pyridin-3-ylpyrimidin-2-yl)amino] benzamide); dasatinib (N-(2-chloro-6-methylphenyl)-2-[[6-[4-(2-hydroxyethyl)-1-piperazinyl]-2-methyl-4-pyrimidinyl]amino]-5-thiazole carboxamide monohydrate); bosutinib (4-[(2,4-dichloro-5-methoxyphenyl)amino]-6-methoxy-7-[3-(4-methylpiperazin-1-yl)propoxy]quinoline-3-carbonitrile); ponatinib (3-(2-Imidazo[1,2-b]pyridazin-3-ylethynyl)-4-methyl-N-[4-[(4-methylpiperazin-1-yl)methyl]-3-(trifluoromethyl)phenyl]benzamide); bafetinib ((S)—N-(3-([5,5'-bipyrimidin]-2-ylamino)-4-methylphenyl)-4-(3-(dimethylamino)pyrrolidin-1-yl)methyl)-3-(trifluoromethyl)benzamide); saracatinib (N-(5-Chloro-1,3-benzodioxol-4-yl)-7-[2-(4-methyl-1-piperazinyl)ethoxy]-5-[(tetrahydro-2H-pyran-4-yl)oxy]-4-quinazolinamine). In some embodiments the tyrosine kinase inhibitor used in the method is at a final concentration of at least 0.5 μM to about 10 μM. In some embodiments the tyrosine kinase inhibitor to be used in the above-described screening method is imatinib. In one embodiment imatinib is used at final concentration of about 5 μM. In preferred embodiments the tyrosine kinase inhibitor inhibits BCR-ABL tyrosine kinase. Suitable test agents for use in the above-described screening assay include small molecules (mol. weight about 200-900 daltons); nucleic acids (e.g., RNAi, modified mRNAs, plasmid expression vectors); peptides; polypeptides; antibodies, or a combination thereof.

For example, where small molecules are to be assayed for their ability to modulate LSC drug resistance, individual test agents may be assayed, e.g., a lead compound from a previous drug screen. In other cases, the test agents to be screened come from a combinatorial library, i.e., a collection of diverse chemical compounds generated by either chemical synthesis or biological synthesis by combining a number of chemical "building blocks." For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. Indeed, theoretically, the systematic, combinatorial mixing of 100 interchangeable chemical building blocks results in the synthesis of 100 million tetrameric compounds or 10 billion pentameric compounds. See, e.g., Gallop et al. (1994), *J. Med. Chem.* 37(9), 1233. Preparation and screening of combinatorial chemical libraries are well known in the art. Combinatorial chemical libraries include, but are not limited to: diversomers such as hydantoins, benzodiazepines, and dipeptides, as described in, e.g., Hobbs et al. (1993), *Proc. Natl. Acad. Sci. U.S.A.* 90, 6909; analogous organic syntheses of small compound libraries, as described in Chen et al. (1994), *J. Amer. Chem. Soc.,* 116: 2661; Oligocarbamates, as described in Cho, et al. (1993), *Science* 261, 1303; peptidyl phosphonates, as described in Campbell et al. (1994), *J. Org. Chem.,* 59: 658; and small organic molecule libraries containing, e.g., thiazolidinones and metathiazanones (U.S. Pat. No. 5,549,974), pyrrolidines (U.S. Pat. Nos. 5,525,735 and 5,519, 134), benzodiazepines (U.S. Pat. No. 5,288,514). Numerous combinatorial libraries are commercially available from, e.g., ComGenex (Princeton, N.J.); Asinex (Moscow, Russia); Tripos, Inc. (St. Louis, Mo.); and Chemdiv. (San Diego, Calif.).

Protein libraries and peptide libraries are also available commercially, (e.g., Five Prime Therapeutics and Mimotopes, respectively).

Where large numbers of test agents are to be evaluated in the above-mentioned screening method, evaluation of iLSC apoptosis can be determined using any of a number of known automated microscopy, high content imaging platforms, enabling the evaluation of up to thousands of test agents per day for their ability to modulate apoptosis induced by a CML drug. Such automated microscopy platforms include, but are not limited to the Opera Phenix™ High Content Screening System (Perkin Elmer), the The ImageXpress® Micro XLS System, and the CellInsight™ NXT High Content Screening (HCS) Platform, all of which support high throughput imaging in 96 or 384 well multiwell optical culture plates, e.g., BIO ONE 96-Well CELLSTAR® Tissue Culture Plates (Greiner, Germany).

In some cases a test agent may be identified to be a modulator that increases the level of apoptosis induced by a CML drug on its own, in which case the test agent is considered to be an inhibitor of resistance to the CML drug. In other cases, a test agent may be found to reduce the level of LSC apoptosis induced by the CML drug, in which case the test agent is considered to be an enhancer of resistance to the CML drug. Identification of enhancers of drug resistance is particularly useful when the test agent has a known mechanism of action (MOA)/target, as this may reveal key pathways and targets that drive CML drug resistance and thereby facilitate efforts to target CML drug resistance based on this information.

A "different level of apoptosis" in the presence versus the absence of a test agent is considered to be from at least a 5% to as much as a 95% difference in the level of apoptosis, e.g., at least a 6%, 7%, 8%, 10%, 12%, 15%, 20%, 30%, 40%, 50%, 60%, 75%, 80%, 90% or another percent difference in the level of LSC apoptosis of at least 5% to as much as 95%.

In some embodiments, the method further includes determining the ability of a test agent, previously identified as modulating apoptosis when assayed in combination with a CML drug, to induce apoptosis in the absence of the CML drug. In other words, some test agents may be identified as modulating apoptosis strictly in the presence of a CML drug, while other test agents may modulate apoptosis independently of the presence a CML drug.

Also disclosed herein is a method for identifying a candidate gene target that confers drug resistance in chronic myeloid leukemia (CML), comprising: (i) culturing induced leukemia stem cell-like cells (iLSCs) in the presence or absence of a drug for treatment of CML; (ii) determining gene expression profiles in the iLSCs cultured in the presence and in iLSCs cultured in the absence of the drug; and (iii) identifying genes that are expressed at different levels in the iLSCs cultured in the presence versus the absence of the drug as a candidate gene target that confers resistance to the drug.

In some embodiments the method further comprises (iv) identifying genes that are expressed at different levels in iLSCs in the presence versus the absence of the CML drug, but are not expressed at different levels in normal iCD4$^+$ cells cultured in the presence versus the absence of the CML drug A number of RNA expression profiling platforms are established in the art, including, but not limited to, RNA microarray hybridization-based methods, bead array hybridization methods, and RNA-Seq-based methods.

In an exemplary embodiment an RNA expression profile is obtained from the cultured LSCs as follows. Total RNA from LSCs is isolated using a PureLink® RNA mini kit (Life Technologies) and subjected to DNase I treatment using a TURBO DNase™ kit (Ambion). Total RNA is quantified using a Life Technologies Qubit® fluorometer (Q32857) and the Agilent Bioanalyzer 2100. Samples are then prepared for sequencing using the Illumina TruSeq RNA Sample Preparation Kit v2 (RS-122-2001), according to the manufacturer's protocol. Final sample libraries are quantified with the Life Technologies Qubit® fluorometer and sequenced on the Illumina HiSeq 2500 (SY-401-1003-PRE). Base-calling and demultiplexing are done with the Illumina Genome Analyzer Casava Software, version 1.8.2. After quality assessment and filtering for adapter molecules and other sequencing artifacts, the remaining sequencing reads are aligned to 19084 RefSeq genes extracted from the Illumina iGenomes annotation, selecting only "NM_" designated genes. Bowtie v 0.12.9 is used, allowing two mismatches in a 28 bp seed, and excluding reads with more than 200 alignments. RSEM v 1.2.3 is used to estimate isoform or gene relative expression levels in units of "transcripts per million" (tpm). Samples are hierarchically clustered on a set of 2855 genes (selected for a minimum TPM of 2.0 in at least one sample, and a minimum fold change of 2.0 between highest and lowest TPM). The samples are clustered using (1-(Spearman rank correlation coefficient)) as the distance metric between each pair of samples. The average distance between each cluster pair is used as the basis to merge lower-level clusters into higher-level clusters. To determine differentially expressed genes, RNAseq output data are analyzed using EBseq(v. 1.1.6) which is available on the internet at the following address: biostat.wisc.edu/~kendzior/EBSEQ/. Genes with posterior probability equal to 1.000 are considered differentially expressed, and thus potential candidate CML drug resistance gene targets. Only genes with tpm≥10 are selected for further analysis.

In some embodiments, determining a gene expression profile in the above-mentioned method, includes determining the expression level, using any of the foregoing RNA profiling technologies, of a gene selected from the group consisting of HLA-DRB, GPNMB, OLR1, HLA-DRA, ACP5, C3, TLR8, APOE, FPR3, RBP7, CYP27A1, TPSB2, PLEKHG5, ABCG1, MS4A7, SULF2, SLC11A1, CCL13, LGALS3, LRP1, GRN, SLAMF8, HLA-DMB, COLEC12, ALOX5AP, IL4I1, CEACAM8, C19orf59, IFI30, FCGR2c, SLCO2B1, C1QB, CCL20, CXCL16, CHI3L1, FBP1, ALDH2, SLC15A3, LILRB5, TM6SF1, RETN, CLEC4A, BCL2A1, ARHGEF10L, NDFIP2, CAPG, SLC8A1, C1QA, HLA-DPA1, STAG, DPYD, HLA-DMA, LGMN, SEMA6B, TNFSF12, MAL, COL8A2, ITGAX, IL9R, MATN2, SLC7A7, KYNU, APOC1, BTG2, C3AR1, CTSS, ALOX15, HLA-B, GIMAP8, TUBA1A, DNASE2, CD2, SBF2, CD68, BMF, S100A10, TBC1D2, SLC37A2, BHLHE40, RTN1, CEACAM1, FLVCR2, CCDC92, FCGR2B, MILR1, LY86, FOLR2, CLEC12A, PLD2, AHNAK, CEACAM4, CD300LF, CTSH, NCF1, S100A6, ADAMDEC1, PILRA, SMAD7, PMP22, TYROBP, NPC2, NLRC4, LGALS1, RNF19B, OSCAR, ALOX5, CST3, DENND2D, OLFM4, NPL, ASAH1, LAPTM5, MYO7B, TRIM22, PPARG, GIMAP1-GIMAP5, RENBP, PREX1, CD52, C4orf34, SAMHD1, HK3, QPCT, GADD45G, CEACAM21, TBX3, SORL1, INSIG1, SIGLEC6, CD38, TP531NP1, NCOA3, FILIP1L, NAPSA, SKIL, TCN1, FRRS1, EGR1, BMP2, TERT, DUSP2, METRN, MDK, ACTL8, MDFI, CHCHD2, GJA1, CPXM1, ARHGAP22, NYNRIN, PACSIN3, GALNT14, and PODXL2.

Therapeutic Methods

As described herein the expression profile of a number of genes in iLSCs relative to BM-iCD34$^+$ cells and in the presence or absence of the CML drug imatinib suggests a number of potential therapeutic targets for treatment of CML. Accordingly, disclosed herein is a method for treating CML comprising administering to a subject in need thereof a therapeutically effective amount of an inhibitor of a gene, or gene product thereof, selected from the group consisting of OLFM4, HLA-DRB, GPNMB, OLR1, HLA-DRA, ACP5, C3, TLR8, APOE, FPR3, RBP7, CYP27A1, TPSB2, PLEKHG5, ABCG1, MS4A7, SULF2, SLC11A1, CCL13, LGALS3, LRP1, GRN, SLAMF8, HLA-DMB, COLEC12, ALOX5AP, IL4I1, CEACAM8, C19orf59, IFI30, FCGR2c, SLCO2B1, C1 QB, CCL20, CXCL16, CHI3L1, FBP1, ALDH2, SLC15A3, LILRB5, TM6SF1, RETN, CLEC4A, BCL2A1, ARHGEF10L, NDFIP2, CAPG, SLC8A1, C1QA, HLA-DPA1, STAG, DPYD, HLA-DMA, LGMN, SEMA6B, TNFSF12, MAL, COL8A2, ITGAX, IL9R, MATN2, SLC7A7, KYNU, APOC1, BTG2, C3AR1, CTSS, ALOX15, HLA-B, GIMAP8, TUBA1A, DNASE2, CD2, SBF2, CD68, BMF, S100A10, TBC1D2, SLC37A2, BHLHE40, RTN1, CEACAM1, FLVCR2, CCDC92, FCGR2B, MILR1, LY86, FOLR2, CLEC12A, PLD2, AHNAK, CEACAM4, CD300LF, CTSH, NCF1, S100A6, ADAMDEC1, PILRA, SMAD7, PMP22, TYROBP, NPC2, NLRC4, LGALS1, RNF19B, OSCAR, ALOX5, CST3, DENND2D, NPL, ASAH1, LAPTM5, MYO7B, TRIM22, PPARG, GIMAP1-GIMAP5, RENBP, PREX1, CD52, C4orf34, SAMHD1, HK3, QPCT, GADD45G, CEACAM21, TBX3, SORL1, INSIG1, SIGLEC6, CD38, TP531NP1, NCOA3, FILIP1L, NAPSA, SKIL, TCN1.

In some embodiments, inhibitors of the above genes or gene products include siRNAs against mRNAs, RNAi vectors (e.g., plasmid or recombinant viral vectors), and antibodies directed against the proteins encoded by such genes. In other embodiments, the inhibitor is an inhibitor of target protein function, e.g., a small molecule enzymatic inhibitor, channel blocker, receptor antagonist, or a decoy peptide that mimics a binding site on an interacting protein partner for the target protein and thereby interferes with the ability of a target protein to interact with the binding partner.

In some embodiments, the gene target or gene target product thereof is OLFM4. The nucleotide sequence of the human OLFM4 cDNA sequence is provided below (SEQ ID NO:7):

```
(SEQ ID NO:7; GenBank Accession No. NM_006418.4)
5'TTTTCCTACATGCTGGCCATGGGGAAATCACCACTGGGCACTATAA

GAAGCCCCTGGGCTCTCTGCAGAGCCAGCGGCTCCAGCTAAGAGGACA

AGATGAGGCCCGGCCTCTCATTTCTCCTAGCCCTTCTGTTCTTCCTTG

GCCAAGCTGCAGGGGATTTGGGGGATGTGGGACCTCCAATTCCCAGCC

CCGGCTTCAGCTCTTTCCCAGGTGTTGACTCCAGCTCCAGCTTCAGCT

CCAGCTCCAGGTCGGGCTCCAGCTCCAGCCGCAGCTTAGGCAGCGGAG

GTTCTGTGTCCCAGTTGTTTTCCAATTTCACCGGCTCCGTGGATGACC

GTGGGACCTGCCAGTGCTCTGTTTCCCTGCCAGACACCACCTTTCCCG

TGGACAGAGTGGAACGCTTGGAATTCACAGCTCATGTTCTTTCTCAGA

AGTTTGAGAAAGAACTTTCCAAAGTGAGGGAATATGTCCAATTAATTA

GTGTGTATGAAAAGAAACTGTTAAACCTAACTGTCCGAATTGACATCA

TGGAGAAGGATACCATTTCTTACACTGAACTGGACTTCGAGCTGATCA

AGGTAGAAGTGAAGGAGATGGAAAAACTGGTCATACAGCTGAAGGAGA

GTTTTGGTGGAAGCTCAGAAATTGTTGACCAGCTGGAGGTGGAGATAA

GAAATATGACTCTCTTGGTAGAGAAGCTTGAGACACTAGACAAAAACA

ATGTCCTTGCCATTCGCCGAGAAATCGTGGCTCTGAAGACCAAGCTGA

AAGAGTGTGAGGCCTCTAAAGATCAAAACACCCCTGTCGTCCACCCTC

CTCCCACTCCAGGGAGCTGTGGTCATGGTGGTGTGGTGAACATCAGCA

AACCGTCTGTGGTTCAGCTCAACTGGAGAGGGTTTTCTTATCTATATG

GTGCTTGGGGTAGGGATTACTCTCCCCAGCATCCAAACAAAGGACTGT

ATTGGGTGGCGCCATTGAATACAGATGGGAGACTGTTGGAGTATTATA

GACTGTACAACACACTGGATGATTTGCTATTGTATATAAATGCTCGAG

AGTTGCGGATCACCTATGGCCAAGGTAGTGGTACAGCAGTTTACAACA

ACAACATGTACGTCAACATGTACAACACCGGGAATATTGCCAGAGTTA

ACCTGACCACCAACACGATTGCTGTGACTCAAACTCTCCCTAATGCTG

CCTATAATAACCGCTTTTCATATGCTAATGTTGCTTGGCAAGATATTG

ACTTTGCTGTGGATGAGAATGGATTGTGGGTTATTTATTCAACTGAAG

CCAGCACTGGTAACATGGTGATTAGTAAACTCAATGACACCACACTTC

AGGTGCTAAACACTTGGTATACCAAGCAGTATAAACCATCTGCTTCTA

ACGCCTTCATGGTATGTGGGGTTCTGTATGCCACCCGTACTATGAACA

CCAGAACAGAAGAGATTTTTTACTATTATGACACAAACACAGGGAAAG

AGGGCAAACTAGACATTGTAATGCATAAGATGCAGGAAAAAGTGCAGA

GCATTAACTATAACCCTTTTGACCAGAAACTTTATGTCTATAACGATG

GTTACCTTCTGAATTATGATCTTTCTGTCTTGCAGAAGCCCCAGTAAG

CTGTTTAGGAGTTAGGGTGAAAGAGAAAATGTTTGTTGAAAAAATAGT

CTTCTCCACTTACTTAGATATCTGCAGGGGTGTCTAAAAGTGTGTTCA

TTTTGCAGCAATGTTTAGGTGCATAGTTCTACCACACTAGAGATCTAG

GACATTTGTCTTGATTTGGTGAGTTCTCTTGGGAATCATCTGCCTCTT

CAGGCGCATTTTGCAATAAAGTCTGTCTAGGGTGGGATTGTCAGAGGT

CTAGGGGCACTGTGGGCCTAGTGAAGCCTACTGTGAGGAGGCTTCACT

AGAAGCCTTAAATTAGGAATTAAGGAACTTAAAACTCAGTATGGCGTC

TAGGGATTCTTTGTACAGGAAATATTGCCCAATGACTAGTCCTCATCC

ATGTAGCACCACTAATTCTTCCATGCCTGGAAGAAACCTGGGGACTTA

GTTAGGTAGATTAATATCTGGAGCTCCTCGAGGGACCAAATCTCCAAC

TTTTTTTTCCCCTCACTAGCACCTGGAATGATGCTTTGTATGTGGCAG

ATAAGTAAATTTGGCATGCTTATATATTCTACATCTGTAAAGTGCTGA

GTTTTATGGAGAGAGGCCTTTTTATGCATTAAATTGTACATGGCAAAT

AAATCCCAGAAGGATCTGTAGATGAGGCACCTGCTTTTTCTTTTCTCT

CATTGTCCACCTTACTAAAAGTCAGTAGAATCTTCTACCTCATAACTT

CCTTCCAAAGGCAGCTCAGAAGATTAGAACCAGACTTACTAACCAATT

CCACCCCCCACCAACCCCCTTCTACTGCCTACTTTAAAAAAATTAATA

GTTTTCTATGGAACTGATCTAAGATTAGAAAAATTAATTTTCTTTAAT

TTCATTATGAACTTTTATTTACATGACTCTAAGACTATAAGAAAATCT

GATGGCAGTGACAAAGTGCTAGCATTTATTGTTATCTAATAAAGACCT

TGGAGCATATGTGCAACTTATGAGTGTATCAGTTGTTGCATGTAATTT

TTGCCTTTGTTTAAGCCTGGAACTTGTAAGAAAATGAAAATTTAATTT

TTTTTTCTAGGACGAGCTATAGAAAAGCTATTGAGAGTATCTAGTTAA

TCAGTGCAGTAGTTGGAAACCTTGCTGGTGTATGTGATGTGCTTCTGT
```

-continued

```
GCTTTTGAATGACTTTATCATCTAGTCTTTGTCTATTTTTCCTTTGAT

GTTCAAGTCCTAGTCTATAGGATTGGCAGTTTAAATGCTTTACTCCCC

CTTTTAAAATAAATGATTAAAATGTGCTTTGAAAAAAGTCAAAAAAAA

AAAAAAAAA-3'
```

The amino acid sequence of human OLFM4 precursor protein (SEQ ID NO:8; GenBank Accession No. NP_006409.3) is:

```
MRPGLSFLLALLFFLGQAAGDLGDVGPPIPSPGFSSFPGVDSSSSFSS

SSRSGSSSSRSLGSGGSVSQLFSNFTGSVDDRGTCQCSVSLPDTTFPV

DRVERLEFTAHVLSQKFEKELSKVREYVQLISVYEKKLLNLTVRIDIM

EKDTISYTELDFELIKVEVKEMEKLVIQLKESFGGSSEIVDQLEVEIR

NMTLLVEKLETLDKNNVLAIRREIVALKTKLKECEASKDQNTPVVHPP

PTPGSCGHGGVVNISKPSVVQLNWRGFSYLYGAWGRDYSPQHPNKGLY

WVAPLNTDGRLLEYYRLYNTLDDLLLYINARELRITYGQGSGTAVYNN

NMYVNMYNTGNIARVNLTTNTIAVTQTLPNAAYNNRFSYANVAWQDID

FAVDENGLWVIYSTEASTGNMVISKLNDTTLQVLNTWYTKQYKPSASN

AFMVCGVLYATRTMNTRTEEIFYYYDTNTGKEGKLDIVMHKMQEKVQS

INYNPFDQKLYVYNDGYLLNYDLSVLQKPQ
```

The amino acid sequence of the mature (secreted) form of human OLM4 (SEQ ID NO:9) is:

```
DLGDVGPPIPSPGFSSFPGVDSSSFSSSRSGSSSSRSLGSGGSVSQ

LFSNFTGSVDDRGTCQCSVSLPDTTFPVDRVERLEFTAHVLSQKFEKE

LSKVREYVQLISVYEKKLLNLTVRIDIMEKDTISYTELDFELIKVEVK

EMEKLVIQLKESFGGSSEIVDQLEVEIRNMTLLVEKLETLDKNNVLAI

RREIVALKTKLKECEASKDQNTPVVHPPPTPGSCGHGGVVNISKPSVV

QLNWRGFSYLYGAWGRDYSPQHPNKGLYWVAPLNTDGRLLEYYRLYNT

LDDLLLYINARELRITYGQGSGTAVYNNNMYVNMYNTGNIARVNLTTN

TIAVTQTLPNAAYNNRFSYANVAWQDIDFAVDENGLWVIYSTEASTGN

MVISKLNDTTLQVLNTWYTKQYKPSASNAFMVCGVLYATRTMNTRTEE

IFYYYDTNTGKEGKLDIVMHKMQEKVQSINYNPFDQKLYVYNDGYLLN

YDLSVLQKPQ
```

In other embodiments disclosed herein is a method for treating CML comprising administering to a subject in need thereof a therapeutically effective amount of an activator of a gene target thereof, selected from the group consisting of: BMP2, TERT, DUSP2, MDK, ACTL8, MDFI, CHCHD2, GJA1, CPXM1, ARHGAP22, NYNRIN, PACSIN3, GALNT14, and PODXL2.

In some embodiments an activator of the gene target is a therapeutic dose of a purified protein comprising the amino acid sequence of the protein encoded by the gene target, e.g., recombinant BMP2 or MDK.

In some embodiments the above-described treatment methods also include administering a therapeutically effective amount of a tyrosine kinase inhibitor. Suitable tyrosine kinase inhibitors for this treatment method include, but are not limited to an inhibitor selected from the group consisting of imatinib, nilotinib, dasatinib, bosutinib, ponatinib, bafetinib and saracatinib. In some of the embodiments the tyrosine kinase inhibitor is a tyrosine kinase inhibitor that inhibits BCR-ABL tyrosine kinase. In some embodiments the tyrosine kinase inhibitor to be administered is imatinib.

The gene target inhibitors or activators described herein can be used in the preparation of medicaments for treatment of CML, particularly CML that is refractory to treatment with a tyrosine kinase inhibitor. In addition, a method for treating CML diseases or conditions described herein in a subject in need of such treatment, involves administration of a pharmaceutical composition containing at least one inhibitor or activator of a gene target as described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the inhibitors or activators described herein can be administered for prophylactic and/or therapeutic treatments. In therapeutic applications, the compositions are administered to a patient already suffering from CML, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial). For example, where the gene target inhibitor is an antibody, see, e.g., Muller et al (2009), *Curr Opin Biotechnol.*, 20(6):722-729.

In prophylactic applications, compositions containing the gene target inhibitors or activators described herein are administered to a patient susceptible to or otherwise at risk of CML. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, can be reduced, as a function of CML symptoms or response. Patients can, however, require intermittent treatment on a long-term basis upon any recurrence of symptoms.

The amount of a given gene target inhibitor (e.g., an OLFM4 antibody) or activator that will correspond to such an amount will vary depending upon factors such as the particular potency and toxicity of the inhibitor or activator, severity and stage of CML, the characteristics (e.g., weight) of the subject in need of treatment, but can nevertheless be routinely determined in a manner known in the art according to the particular circumstances surrounding the case, including, e.g., the specific inhibitor or activator agent being administered, the route of administration, the CML stage being treated, and the subject being treated. In general, however, doses employed for adult human treatment will typically be in the range of 2 mg per day to 5000 mg per day. The desired dose may conveniently be presented in a single dose or as divided doses administered simultaneously (or over a short period of time) or at appropriate intervals, for example as two, three, four or more sub-doses per day. For example, where a gene target inhibitor is an antibody, an exemplary dosing regimen would be an initial dose of about 300 mg, followed one week later by 2000 mg once weekly for seven infusions, followed 4 to 5 weeks later by 2000 mg once every 4 weeks for 4 infusions, for a total of 12 infusions. In some cases, where CML treatment includes administration of a tyrosine kinase inhibitor (e.g., imatinib), dosing typically ranges from about 300 mg to about 600 mg per day (oral route of administration)

The foregoing ranges are merely suggestive, as the number of variables in regard to an individual treatment regime is large, and considerable excursions from these recommended values are not uncommon. Such dosages may be altered depending on a number of variables, not limited to the activity of the gene target inhibitor or activator used, the stage of CML to be treated, the mode of administration, the requirements of the individual subject, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the model population) and the $ED_{50}$ (the dose therapeutically effective in 50% of the test population. The dose ratio between the toxic and therapeutic effects is the therapeutic index and it can be expressed as the ratio between $LD_{50}$ and $ED_{50}$. The data obtained from cell culture assays and animal studies can be used in formulating a range of dosage for use in human. The dosage of such compounds lies preferably within a range of circulating concentrations that include the ED.sub.50 with minimal toxicity. The dosage may vary within this range depending upon the dosage form employed and the route of administration utilized.

In some embodiments, gene target inhibitors or activators are administered by one or more of a variety of routes, including, but not limited to, local, oral, intravenous, intramuscular, intra-arterial, intramedullary, intrathecal, subcutaneous, intraventricular, transdermal, intradermal, rectal, intravaginal, intraperitoneal, topical (e.g. by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter.

In some embodiments, gene target inhibitors or activators are administered by systemic intravenous injection. In other embodiments, gene target inhibitors or activators may be administered intravenously and/or orally.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S. P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

Dosage forms for local, topical and/or transdermal administration of a composition may include ointments, pastes, creams, lotions, gels, powders, solutions, sprays, inhalants and/or patches. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions.

Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

In general the most appropriate route of administration will depend upon a variety of factors including the nature of the gene target inhibitor or activator to be delivered (e.g., its stability in the environment of the gastrointestinal tract, bloodstream, etc.), the condition of the patient (e.g., whether the patient is able to tolerate particular routes of administration), etc.

In some embodiments described herein, a gene target inhibitor (e.g., an OLFM4 antibody) is used in combination with a tyrosine kinase inhibitor (e.g., a BCR-ABL tyrosine kinase inhibitor). It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

The gene target inhibitor (e.g., OLFM4 inhibitor) or activator and tyrosine kinase inhibitor compound provided herein may be administered to a CML patient either simultaneously or sequentially. If administered sequentially, the attending physician will decide on the appropriate sequence of administering gene target inhibitor or activator in combination with the tyrosine kinase inhibitor.

In any case, the multiple therapeutic agents (one of which is an inhibitor or activator of a gene target described herein, and the other a tyrosine kinase inhibitor) may be administered in any order or even simultaneously. If simultaneously, the multiple therapeutic agents may be provided in a single, unified form, or in multiple forms (by way of example only, as a pill for the tyrosine kinase inhibitor and an IV injection for gene target inhibitor antibody). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

II. Compositions

Also described herein are compositions directed to the treatment of CML, and in particular to the treatment of CML therapeutic resistance.

Kits

Disclosed herein is a kit for the treatment of CML containing therapeutically effective doses of a tyrosine kinase inhibitor and an inhibitor of a gene target selected from the group consisting of OLFM4, HLA-DRB, GPNMB, OLR1, HLA-DRA, ACP5, C3, TLR8, APOE, FPR3, RBP7, CYP27A1, TPSB2, PLEKHG5, ABCG1, MS4A7, SULF2, SLC11A1, CCL13, LGALS3, LRP1, GRN, SLAMF8, HLA-DMB, COLEC12, ALOX5AP, IL4I1, CEACAM8, C19orf59, IFI30, FCGR2c, SLCO2B1, C1 QB, CCL20, CXCL16, CHI3L1, FBP1, ALDH2, SLC15A3, LILRB5, TM6SF1, RETN, CLEC4A, BCL2A1, ARHGEF10L, NDFIP2, CAPG, SLC8A1, C1QA, HLA-DPA1, STAG, DPYD, HLA-DMA, LGMN, SEMA6B, TNFSF12, MAL, COL8A2, ITGAX, IL9R, MATN2, SLC7A7, KYNU, APOC1, BTG2, C3AR1, CTSS, ALOX15, HLA-B, GIMAP8, TUBA1A, DNASE2, CD2, SBF2, CD68, BMF, S100A10, TBC1D2, SLC37A2, BHLHE40, RTN1, CEACAM1, FLVCR2, CCDC92, FCGR2B, MILR1, LY86, FOLR2, CLEC12A, PLD2, AHNAK, CEACAM4, CD300LF, CTSH, NCF1, S100A6, ADAMDEC1, PILRA, SMAD7, PMP22, TYROBP, NPC2, NLRC4, LGALS1, RNF19B, OSCAR, ALOX5, CST3, DENND2D, NPL, ASAH1, LAPTM5, MYO7B, TRIM22, PPARG, GIMAP1-GIMAP5, RENBP, PREX1, CD52, C4orf34, SAMHD1, HK3, QPCT, GADD45G, CEACAM21, TBX3, SORL1, INSIG1, SIGLEC6, CD38, TP53I1NP1, NCOA3, FILIP1L, NAPSA, SKIL, and TCN1.

Optionally, the kit may also contain instructions for combination treatment of CML methods, as described herein, with the provided tyrosine kinase inhibitor and inhibitor of the gene target.

Suitable tyrosine kinase inhibitors include, but are not limited to, imatinib, nilotinib, dasatinib, bosutinib, ponatinib, bafetinib and saracatinib. In some embodiments the tyrosine kinase inhibitor is a tyrosine kinase inhibitor that inhibits BCR-ABL kinase. In some embodiments the tyrosine kinase inhibitor is imatinib.

Gene target inhibitors, as referred to herein, encompass inhibitors of gene target mRNA or proteins encoded by a gene target. Such gene target inhibitors include, but are not limited to, an siRNA against the gene target mRNA, a knock-down vector against the gene target mRNA, or an antibody against a protein encoded by the gene target, or a small molecule (less than or equal to 900 daltons) that inhibits the function of a protein encoded by a gene target.

In some embodiments the gene target inhibitor included in the kit is an inhibitor of OLFM4. In some embodiments the tyrosine kinase inhibitor inhibits a BCR-ABL kinase. In some embodiments the tyrosine kinase inhibitor is selected from the group consisting of: imatinib, nilotinib, dasatinib, bosutinib, ponatinib, bafetinib and saracatinib. In some embodiments the tyrosine kinase inhibitor to be included is imatinib.

Methods for the generation of various classes of gene target inhibitors, as mentioned above are known. For methods for designing siRNAs and their therapeutic delivery, see, e.g., Gavrilov et al (2012), *Yale J Biol Med.*, 85(2):187-200; Zhang et al (2013), *Blood,* 121(8):1304-1315. Commercially designed collections and custom design of siRNAs are available from a number of vendors, e.g., Accell siRNA (ThermoFisher), Silencer® Select siRNAs (Life Technologies), and Mission® siRNA (Sigma).

In vivo delivery of nucleic acids may be affected by many parameters, including, but not limited to, the formulation composition, nature of particle PEGylation, degree of loading, oligonucleotide to lipid ratio, and biophysical parameters such as particle size (Akinc et al (2009), *Mol. Ther.,* 17:872-879). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N 12-5, see Murugaiah et al (2010), *Analytical Biochemistry,* 401(1):61-67, C 12-200 (including derivatives and variants), MD1, DLin-DMA, DLin-K-DMA, DLin-KC2-DMA and DLin-MC3-DMA, can be tested for in vivo activity. Typically, siRNA and lipidoids are utilized in lipidoid:siRNA (wt/wt) ratio of: 2.5:1, 5:1, 10:1, and 15:1.

Viral vectors (e.g., recombinant lentiviruses) comprising shRNA expression cassettes and competent to transduce hematopoietic stem cells have been described in the art, e.g., in Shimizu et al (2010), *Blood,* 115(8):1534-1544, and Geilling et al (2013), *PLoS One,* 8(10):e76279.

In some embodiments, an inhibitor of a gene target or gene target product is an antibody directed against a protein encoded by one of the foregoing genes. In some embodiments antibody is a monoclonal antibody directed against human OLFM4. For example, the CDR regions of the monoclonal antibody against human OLFM4 can be derived from a mouse monoclonal antibody, e.g., mouse Monoclonal IgG1 against human OLFM4 from Life Technologies (11639-MM12-AB); from Creative Biomart (Cat. No. DMABT-H40255); USCN Life Science Inc (Cat No. MAA162Hu22). Mouse hybridoma lines secreting antibodies against human OLFM4 are also available commercially, e.g. AbNova (Cat. No. H00010562-M)

Antibodies suitable for the above-mentioned treatment method can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The starting antibodies for development of a therapeutic-grade antibody suitable for human administration may be murine, rat, rabbit, sheep, goat, chicken, or human. In some embodiments, the inhibitor antibody is a monoclonal antibody. In some embodiments, the inhibitor antibody is a humanized antibody. In some embodiments, the antibody is a human antibody.

In some embodiments, the antibody comprises a modified constant region, such as a constant region that is immunologically inert described herein. In some embodiments, the constant region is modified as described in U.S. Pat. No. 7,597,889.

The binding affinity $K_D$ of an inhibitor antibody to its target protein (e.g., OLFM4 as described herein) can be about 0.02 nM to about 200 nM. In some embodiments, the binding affinity is from about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

The inhibitor antibodies can be generated by any of a number of methods known in the art. Immunization of a host animal with a target protein immunogen is generally in keeping with established and conventional techniques for antibody stimulation and production, as further described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for a target protein selected from the above-mentioned list of, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a protein encoded by one of the gene targets disclosed herein, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaradehyde, succinic anhydride, SOCl2, or R1N.dbd.C.dbd.NR, where R and R1 are different alkyl groups, can yield a population of antibodies (e.g., monoclonal antibodies).

If desired, the inhibitor antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the gene target protein (e.g., an OLFM4 protein) and greater efficacy in inhibiting the gene target protein. It will be apparent to one of skill in the art that one or more polynucleotide changes can be made to the inhibitor antibody and still maintain its affinity.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. Nature 349:293-299 (1991), Lobuglio et al. Proc. Nat. Acad. Sci. USA 86:4220-4224 (1989), Shaw et al. J. Immunol. 138:4534-4538 (1987), and Brown et al. Cancer Res. 47:3577-3583 (1987). Other references describe rodent CDRs grafted into a human supporting framework region (FR) prior to fusion with an appropriate human antibody constant domain. See, for example, Riechmann et al. Nature 332:323-327 (1988), Verhoeyen et al. Science 239:1534-1536 (1988), and Jones et al. Nature 321:522-525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476 (1991) and in U.S. Pat. Nos. 6,180,377; 6,054,297; 5,997,867; 5,866,692; 6,210,671; and 6,350,861; and in PCT Publication No. WO 01/27160.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies.

In an alternative, antibodies may be made recombinantly and expressed using any method known in the art. In another alternative, antibodies may be made recombinantly by phage display technology. See, for example, U.S. Pat. Nos. 5,565, 332; 5,580,717; 5,733,743; and 6,265,150; and Winter et al., *Annu. Rev. Immunol.* 12:433-455 (1994). Alternatively, the phage display technology (McCafferty et al., *Nature* 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., Current Opinion in Structural Biology 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., EMBO J. 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., Bio/Technol. 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

Antibodies may be made by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. *Vaccine* 19:2756 (2001); Lonberg, N. and D. Huszar *Int. Rev. Immunol* 13:65 (1995); and Pollock, et al., *J Immunol Methods* 231:147 (1999). Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for a gene target protein (e.g., human OLF4M protein).

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., *Proc. Nat. Acad. Sci.* 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of a monoclonal antibody directed against a gene target protein disclosed herein.

Pharmaceutical Compositions

In some embodiments provided herein is a pharmaceutical composition comprising a pharmaceutically acceptable excipient; and a therapeutically effective amount of at least one inhibitor of a gene target selected from the group consisting of: elected from the group consisting of OLFM4, HLA-DRB, GPNMB, OLR1, HLA-DRA, ACP5, C3, TLR8, APOE, FPR3, RBP7, CYP27A1, TPSB2, PLEKHG5, ABCG1, MS4A7, SULF2, SLC11A1, CCL13, LGALS3, LRP1, GRN, SLAMF8, HLA-DMB, COLEC12, ALOX5AP, IL4I1, CEACAM8, C19orf59, IFI30, FCGR2c, SLCO2B1, C1QB, CCL20, CXCL16, CHI3L1, FBP1, ALDH2, SLC15A3, LILRB5, TM6SF1, RETN, CLEC4A, BCL2A1, ARHGEF10L, NDFIP2, CAPG, SLC8A1, C1QA, HLA-DPA1, STAG, DPYD, HLA-DMA, LGMN, SEMA6B, TNFSF12, MAL, COL8A2, ITGAX, IL9R, MATN2, SLC7A7, KYNU, APOC1, BTG2, C3AR1, CTSS, ALOX15, HLA-B, GIMAP8, TUBA1A, DNASE2, CD2, SBF2, CD68, BMF, S100A10, TBC1D2, SLC37A2, BHLHE40, RTN1, CEACAM1, FLVCR2, CCDC92, FCGR2B, MILR1, LY86, FOLR2, CLEC12A, PLD2, AHNAK, CEACAM4, CD300LF, CTSH, NCF1, S100A6, ADAMDEC1, PILRA, SMAD7, PMP22, TYROBP, NPC2, NLRC4, LGALS1, RNF19B, OSCAR, ALOX5, CST3, DENND2D, NPL, ASAH1, LAPTM5, MYO7B, TRIM22, PPARG, GIMAP1-GIMAP5, RENBP, PREX1, CD52, C4orf34, SAMHD1, HK3, QPCT, GADD45G, CEACAM21, TBX3, SORL1, INSIG1, SIGLEC6, CD38, TP531NP1, NCOA3, FILIP1L, NAPSA, SKIL, and TCN1 (e.g., an inhibitor of OLFM4 mRNA or an inhibitor of OLFM4 protein). In some embodiments the gene target inhibitor comprises at least one siRNA against human OLFM4 mRNA. In other embodiments the gene target inhibitor comprises at least one antibody against human OLFM4 protein.

In other embodiments the pharmaceutical composition comprises a pharmaceutically acceptable excipient; and a therapeutically effective amount of at least one gene target selected from the group consisting of BMP2, TERT, DUSP2, MDK, ACTL8, MDFI, CHCHD2, GJA1, CPXM1, ARHGAP22, NYNRIN, PACSIN3, GALNT14, and PODXL2.

In some embodiments, where a gene target activator protein is known to have extracellular biological function, the gene target protein activator is provided as a recombinant form of the encoded gene target protein. Methods for the recombinant production of proteins is well established in the art. In other embodiments, where the gene target protein is known to have an intracellular function, a gene target activator is a modified mRNA (mmRNA) encoding the gene target protein. The synthesis and delivery of mmRNAs is described in detail in, e.g., U.S. patent application publication Nos. 20120251618, 20130115272, 20130123481, 20130156849, and 20130236974.

In some embodiments a pharmaceutical composition comprises, in addition to a pharmaceutically acceptable excipient and a gene target inhibitor or activator, at least one tyrosine kinase inhibitor. In some embodiments the tyrosine kinase inhibitor is a tyrosine kinase inhibitor that inhibits BCR-ABL tyrosine kinase (e.g., imatinib). In other embodiments the tyrosine kinase inhibitor included in the pharmaceutical composition is a tyrosine kinase inhibitor selected from the group consisting of imatinib, nilotinib, dasatinib, bosutinib, ponatinib, bafetinib and saracatinib.

In some embodiments the gene target inhibitor included in a pharmaceutical composition is an antibody to a protein encoded by the gene target (e.g., an OLF4M protein). Various formulations of a gene target antibody are contemplated herein. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, *The Science and Practice of Pharmacy* 20th Ed. Mack Publishing (2000).

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

A gene target protein antibody can be administered using any suitable method, including by injection (e.g., intraperitoneally, intravenously, subcutaneously, intramuscularly, etc.).

Therapeutic formulations of the gene target antibody used in accordance with the present invention are prepared for storage by mixing an antibody having the desired degree of purity with optional pharmaceutically acceptable carriers, excipients or stabilizers (Remington, *The Science and Practice of Pharmacy* 20th Ed. Mack Publishing (2000)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosacchandes, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some embodiments active ingredients (e.g., an antibody and a tyrosine kinase inhibitor) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Typically, the pharmaceutical compositions described herein comprise pharmaceutically acceptable carriers, excipients, or stabilizers (Remington: The Science and practice of Pharmacy 20th Ed. (2000) Lippincott Williams and Wilkins, Ed. K. E. Hoover.), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counterions such as sodium; metal complexes (e.g. Zn-protein complexes); and/or non-ionic surfactants such as TWEEN™, PLURONICS™ or polyethylene glycol (PEG).

The invention will be more fully understood upon consideration of the following non-limiting Examples.

EXAMPLES

Example 1

Generation of Leukemia Stem Cell (LSC)-Like Cells from CM-hiPSCs

Figures 2A, 2B:
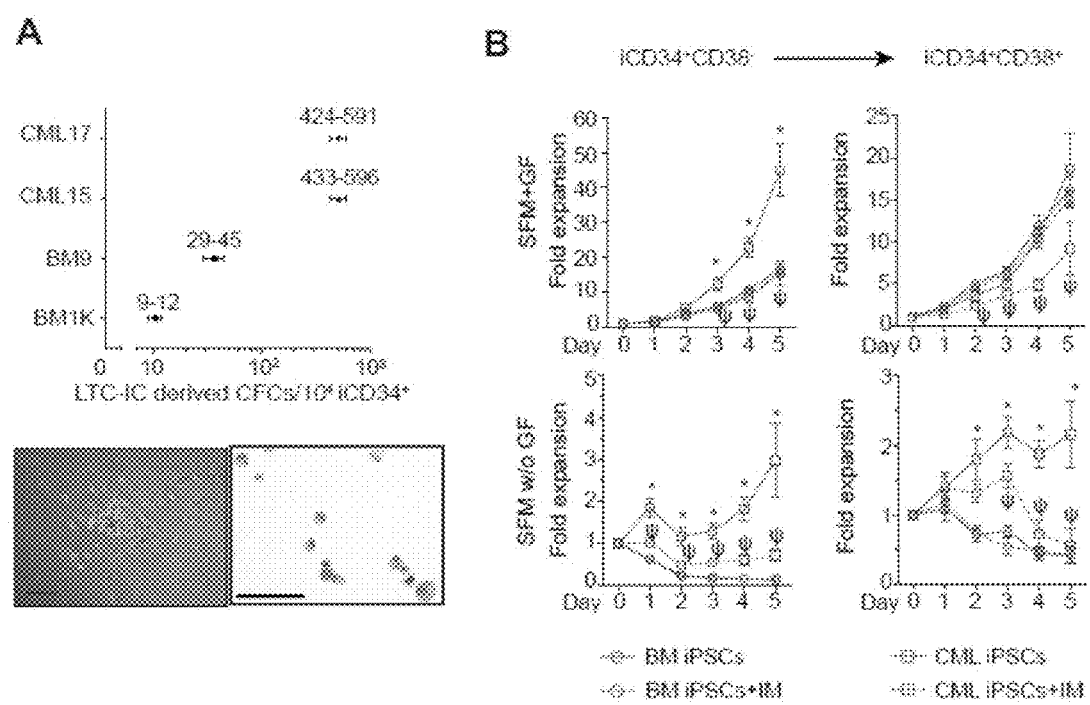
FIG. 2 Stem/progenitor cell properties of CML and control BM $iCD34^+$ cells. (A) LTC-IC assay of CML and BM $iCD34^+$ cells. Numbers next to the plot show the total number of CFCs detected in LTC-IC cultures of $iCD34^+$ cells. Results are mean±SEM of two biological replicates performed in triplicates. Representative colony and Wright stained cytospin from the colony formed by iCML $CD34^+$ cells after 5 weeks of LTC-IC culture are shown. Scale bar=100 µm. (B) Expansion of CML and BM $iCD34^+$ cells in serum-free medium (SFM) with and without growth factors (GF) in presence or absence of imatinib. Where indicated, 5 µM imatinib (IM) was added. Results are mean±SEM from six independent experiments (three from each BM1K and BM9 $iCD34^+$, and three from each CML15 and CML17 $iCD34^+$). * indicates significant differences between cell counts in BM control and CML $iCD34^+$ cultures ($p<0.05$). ψ indicates significant differences between imatinib treated and untreated CML $iCD34^+$ cells ($p<0.05$). (C) Colony formation from BM and CML $iCD34^+$ cells. Results are mean±SEM from 3 independent experiments. * $p<0.01$. (D) Adhesion of BM and CML $iCD34^+$ cells to fibronectin or control bovine serum albumin (BSA)-adsorbed plates and the effect of imatinib on adhesion of $iCD34^+$ cells to fibronectin. * $p≤0.02$. Results are mean±SEM from three independent experiments.
Figures 2C, 2D:
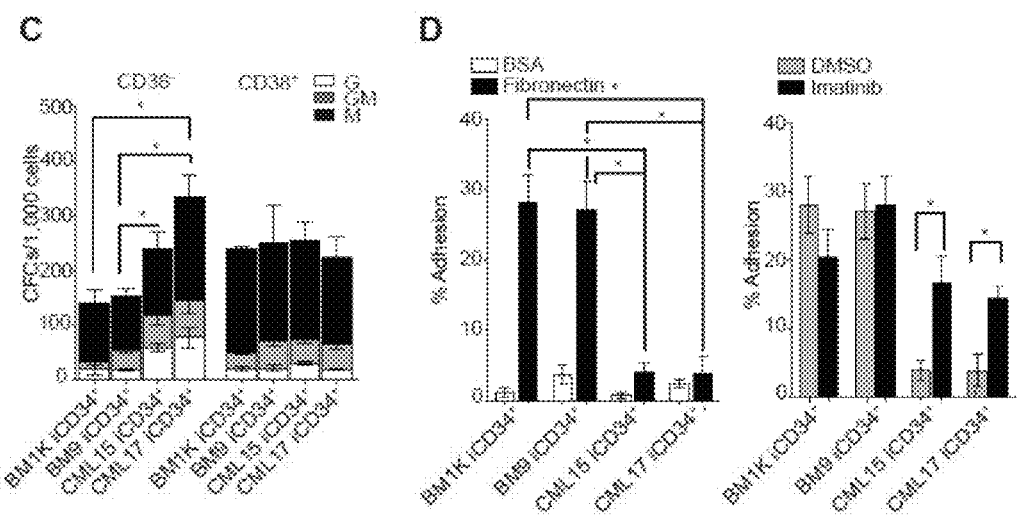
Figures 7A, 7B, 7C:
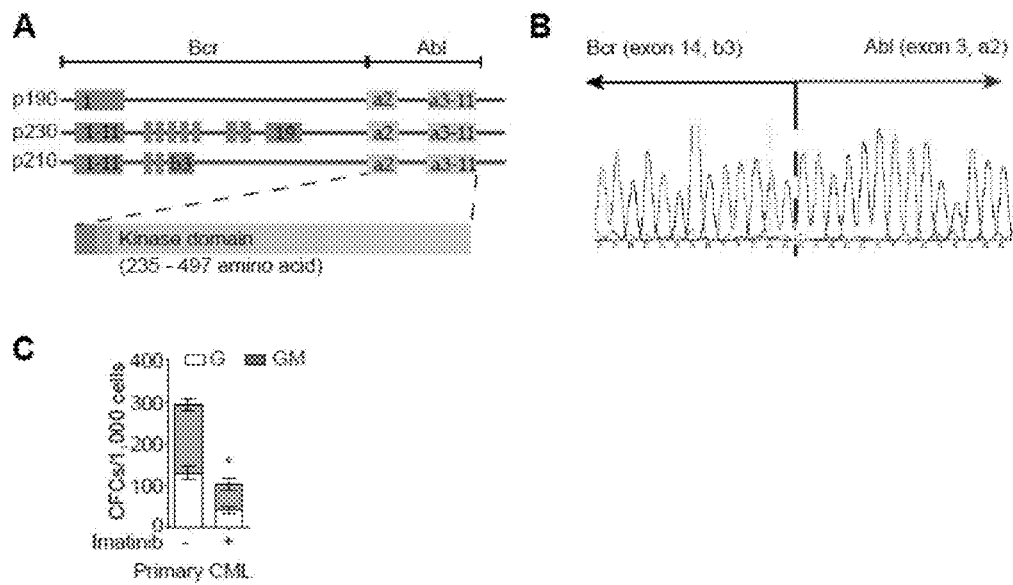
FIG. 7 (A) Schematic diagram shows three different isoforms of the BCR-ABL protein. (B) CML iPSCs expressed typical p210 isoform without mutation in the kinase domain (235-497 amino acid). Flow chromatogram depicts the site of translocation junction. (C) The effect of imatinib pretreatment on myeloid CFC potential of parental lin− CD34+ BM cells from CML patient used to generate iPSCs. Somatic lin−CD34+ were incubated 24 hours in serum-free medium with low concentrations of growth factors with or without 5 µM imatinib and transferred to CFC medium. Results are mean±SEM of three experiments. * p<0.05.

Recently we generated transgene-free iPSCs from the bone marrow mononuclear cells of patient in the chronic phase of CML (CML15 iPSCs and CML17 iPSCs) and showed that these iPSCs capture the entire genome of neoplastic cells, including the unique 4-way translocation between chromosomes 1, 9, 22, and 11 that was present in the patient bone marrow (BM) (Hu et al., 2011). Sequencing analysis revealed that BCR-ABL translocation in these CML-iPSCs is associated with p210 isoform with typical b3a2 rearrangement without any mutation in the kinase domain consistent with observed sensitivity of parental bone marrow cells to imatinib (FIG. 7A-C). CML LSCs have been identified within the most primitive hematopoietic compartment as cells with long-term culture initiating cell (LTC-IC) or in vivo repopulating activities (Corbin et al., 2011; Li et al., 2012; Petzer et al., 1996; Sloma et al., 2010; Udomsakdi et al., 1992b). Similar to normal HSCs, CML LSCs express markers of primitive hematopoietic cells including CD34 and CD90, and are negative for hematopoietic lineage markers (lin$^-$) and CD45RA (Udomsakdi et al., 1992b). They display aldehyde dehydrogenase (ALDH) activity and the ability to efflux Rhodamine-123 (Udomsakdi et al., 1992a). To find out whether cells with similar characteristics can be generated from CML iPSCs we induced their hematopoietic differentiation in coculture with OP9. In this system, CML iPSCs similar to control bone marrow iPSCs (BM1K and BM9) formed CD34$^+$CD43$^+$ hematopoietic progenitors, including CD235a$^-$CD41a$^-$CD45$^+$ cells highly enriched in myeloid progenitors (Hu et al., 2011; Vodyanik et al., 2006) (FIGS. 1A and 1B). As shown in FIG. 1B, CD235a$^-$CD41a$^-$CD45$^+$ cells obtained at day 9 of differentiation displayed the phenotypic features of CML LSCs including expression of CD34, CD90 and CD117 primitive hematopoietic cell markers and a lack of other lineage and CD38 and CD45RA markers, i.e. had a typical lin$^-$CD34$^+$CD38$^-$CD45RA$^-$CD90$^+$CD117$^+$ HSC phenotype. Similar to somatic CML LSCs, these cells displayed ALDH activity and the ability to efflux Rhodamine-123 (FIG. 1C). After expansion, CD45$^+$ cells retained expression of stem cell markers and remained lin$^-$ and CD45RA$^-$, however some of them (approximately 25%) acquired expression of CD38 (FIG. 1B, day 11). Following further culture with hematopoietic cytokines, lin$^-$CD34$^+$CD45$^+$38$^{+/-}$ (hereafter referred to as induced CD34$^+$; iCD34$^+$) cells acquired expression of lineage-specific markers and lost CD34 expression (i.e. became lin$^+$CD34; iCD34$^-$ cells). CML iCD34$^+$ were highly enriched in myeloid CFCs with the number of myeloid CFCs within the CD38$^-$ compartment significantly higher in CML iCD34$^+$ cells as compared to control BM iCD34$^+$ cells (FIG. 2C).

Although CML LSCs share many properties with HSCs, they have abnormally increased long-term survival and proliferation (Corbin et al., 2011; Holyoake et al., 1999), the ability to grow in vitro without added cytokines (Jiang et al., 1999), and an adhesion defect (Bhatia et al., 2001; Verfaillie et al., 1992). Using the LTC-IC assay, we found that iCML CD34$^+$ cells produced a much higher number of LTC-IC-derived CFCs as compared to BM iCD34$^+$ cells, indicating increased long-term survival (FIG. 2A). In addition, CML iCD34$^+$ cells demonstrated significantly higher proliferative potential in serum-free medium with growth factors, as compare to control BM iCD34$^+$ cells, and an ability to withstand growth factor deprivation in serum-free conditions without cytokines (FIG. 2B). CML iCD34$^+$ cells displayed the adhesion defect typically present in somatic LSCs, as revealed by their reduced adhesion to fibronectin, which was partially restored with imatinib treatment (FIG. 2D). Overall, these findings provided strong evidence that lin$^-$CD34$^+$CD45$^+$ cells derived from CML IPSCs behave similarly to their somatic counterpart.

Materials and Methods iPSCs Maintenance and Differentiation

We used previously described transgene-free BM9, CML15 and CML17 iPSCs produced by reprogramming bone marrow mononuclear cells from normal and CML patients in the chronic phase (Hu et al., 2011). BM1K iPSC was generated from the normal control using the same approach (Hu et al., 2011). Undifferentiated iPSCs were maintained in cocultures with mouse embryonic fibroblasts (MEFs). Hematopoietic differentiation was induced by transferring the iPSCs to overgrown OP9 feeders as we have previously described in detail (Choi et al., 2009a; Vodyanik et al., 2005). CD43$^+$ cells were collected on day 9 of differentiation using MACS and cultured in α-MEM supplemented with 10% FBS, 50 μg/ml ascorbic acid, 100 μM monothioglycerol (complete serum supplemented medium (CSSM)) and 200 ng/ml GM-CSF to expand selectively myeloid progenitors. (Choi et al., 2009a) After two days of expansion with GM-CSF CD43$^+$ cells enriched in myeloid progenitors were cultured for an additional four days in the same media supplemented with 10 ng/ml IL-3, 100 ng/ml IL-6, 100 ng/ml Flt3L, 100 ng/ml SCF, and 200 ng/ml GM-CSF (all from Peprotech). Purification of Lin$^-$CD34$^+$CD45$^+$ from iPSCs-Derived CD43$^+$ CD43$^+$ hematopoietic cells were collected from differentiated iPSC cultures using MACS and labeled with CD235a/CD41a FITC, CD45 APC and CD38 PE (BD Pharmingen). Lin$^-$CD45$^+$CD38$^+$ and lin$^-$CD45$^+$CD38$^-$ subpopulations were obtained by fluorescence-activated cell sorter (FACSAria) (Vodyanik et al., 2006). Bone marrow mononuclear cells from CML patients in the chronic phase were purchased commercially (AllCells or Applied StemCells), or obtained from the patients at the University of Wisconsin Hospital and Clinics (Madison, Wis.) with approval from the University of Wisconsin Institutional Review Board. Donors had previously signed an Institutional Review Board-approved consent. Bone marrow cells from healthy donors were obtained from Cincinnati Children's Hospital Medical Center (CCHMC). Mononuclear cells were labeled with the lineage-specific markers CD2, CD3, CD14, CD15, CD16, CD19, CD20, CD24, CD41a, CD56, CD66b, and Glycophorin A (FITC-conjugated antibodies), CD34 APC (BD Pharmingen) and DAPI to exclude dead cells. Live lin$^-$CD34$^+$ cells were isolated using FACSAria (BD).

Hematopoietic Colony-Forming Assay

Hematopoietic clonogenic assays were performed using serum-containing StemMACS semisolid clonogenic medium (Miltenyi Biotec, CA). Colonies were scored after fourteen to 21 days of incubation. When indicated, $CD34^+$ cells were plated in clonogenic medium with DMSO or 10 μM imatinib or were pretreated with DMSO or 5 μM imatinib for 24 hours in serum free medium (SFM) composed of IMDM, 10% BIT (Stem Cell Technologies), 2-mercaptoethanol, and EXCYTE (Millipore) and supplemented with low concentration of growth factors (1 ng/ml of each SCF, IL3, IL6, Flt3L and GM-CSF).

Long-Term Culture Initiating Cell Assay (LTC-IC)

Sorted iPSC-derived $lin^-CD34^+CD45^+$ cells were plated in a six-well plate at $10^4$ cells/well containing 5-7 day-old cultures of murine $1 \times 10^5$ M2-10B4 and OP9 stromal cells (1:1 ratio mix) in LTC-IC medium consisting of SFM supplemented with 10 μM hydrocortisone, 50 ng/ml SCF, 5 ng/ml IL3, and 50 ng/ml IL6. Cultures were maintained at 37° C. in a humidified atmosphere with 5% $CO_2$, and fed at weekly intervals. After five weeks, cells were harvested and analyzed for CFC potential as described above. LTC-IC assay for somatic $lin^-CD34^+CD45^+$ cells was performed using M2-10B4 cells exactly as described in the Stem Cell Technologies protocol to be found online at stemcell.com/en/Technical-Resources/db5a9/28412_ltc_ic-H.aspx. When indicated, cells were pretreated for one week with 5 μM imatinib or DMSO (control), in SFM supplemented with low concentration of growth factors (1 ng/ml of each SCF, IL3, IL6, Flt3L and GM-CSF), and transferred to LTC-IC cultures for an additional five weeks of culture. In some experiments cells were transfected with either OLFM4 or negative control siRNA and pretreated with imatinib or DMSO as described above.

Rhodamine 123 Exclusion Assay

FACS isolated $lin^-CD34^+CD38^-$ and $CD38^+$ cells were incubated with 0.5 μg/ml rhodamine (Rho) (Molecular Probes, Eugene, Oreg.) in 1 ml of alpha MEM medium containing 2% FBS (assay medium) for 30 minutes at 37° C. After washing, cells were resuspended in assay medium and incubated for 40 minutes at 37° C. with and without 50 μM verapamil (Sigma) to reveal Rho exclusion activity. Cells were labeled with CD45-APC and 7-AAD (Sigma) and analyzed using FACSCalibur flow cytometer (BD). $Rho^{low}$ cells were defined as those showing less fluorescence in the FL-1 channel than exhibited in verapamil-treated samples.

Aldehyde Dehydrogenase Activity

Aldehyde dehydrogenase (ALDH) staining of $lin^-CD45^+CD38^-$ and $Lin^-CD45^+CD38^+$ cells was performed with Aldefluor kit (Stem Cell Technologies) according to manufacturer instructions. Control samples were established using diethylaminobenzaldehyde (DEAB), an ALDH inhibitor. Cells were also labeled with CD45-APC, and dead cells were excluded using 7-AAD staining. Samples were analyzed by flow cytometry.

Cell Proliferation Assay

Total $lin^-CD34^+$, $lin^-CD34^+CD38^-$ or $lin^-CD34^+CD38^+$ were plated in triplicate in 96-well plate at $10^3$ cells/well. Cells were cultured in SFM with or without 5 μM imatinib. When specified, the 300 ng/ml OLFM4 (Acro Biosystem) or the following growth factors were added: 10 ng/ml IL3, 100 ng/ml SCF, 100 ng/ml Flt3L, 100 ng/ml IL6 and 200 ng/ml GM-CSF. Viable cell yields were determined by counting trypan blue excluding viable cells using a hemocytometer.

$IC_{50}$ Assay

The $lin^-CD34^+$ and $lin^+CD34^-$ cells were plated at $10^3$ cells/well in 96-well plate in CSSM containing 10 ng/ml IL3, 100 ng/ml IL6, 200 ng/ml GM-CSF, 100 ng/ml SCF, and 100 ng/ml Flt3L with 0-100 μM imatinib. After 24 hours of culture, viable cell count was performed using trypan blue. The $IC_{50}$ was determined as the concentration of drug where cell death was 50% of that in relevant control wells (Sebaugh, 2011). Data from three assays performed in triplicate were used for statistical analysis and graphs plotted for $IC_{50}$ determinations. Relative $IC_{50}$ were determined by fitting an exponential dose-response curve to the cell proliferation data by using GraphPad Prism software (GraphPad, San Diego, Calif.).

CFSE Tracking of Cell Division

Differentiated cells were labeled with 1 μM carboxy-fluorescein diacetate succinimidyl diester (CFSE; Molecular Probes, Eugene, Oreg.) as previously described (Copland et al., 2006; Holtz et al., 2002). These cells were then incubated overnight in CSSM medium supplemented with growth factors to allow excess unbound dye to leak out of the cells. Cells cultured in the presence of 10 μg/ml mitomycin C (Sigma Aldrich) were used to establish the $CFSE_{max}$ (undivided cell population). The next day, $CFSE^{bright}$ cells were sorted by FACArias to exclude non-labeled and $CFSE^{dim}$ populations. These cells were then cultured for four days in CSSM supplemented with growth factors with or without 5 μM imatinib. At the end of the culture period, cells were stained with CD34-APC and 7AAD for flow cytometry analysis. The percentage of cells in each generation was determined using FlowJo software (Tree Star, Ashland, Oreg.), with the position of the parent generation set on the basis of the fluorescence profile of undivided cells.

Adhesion Assay

Figures 9A, 9B, 9C, 9D:
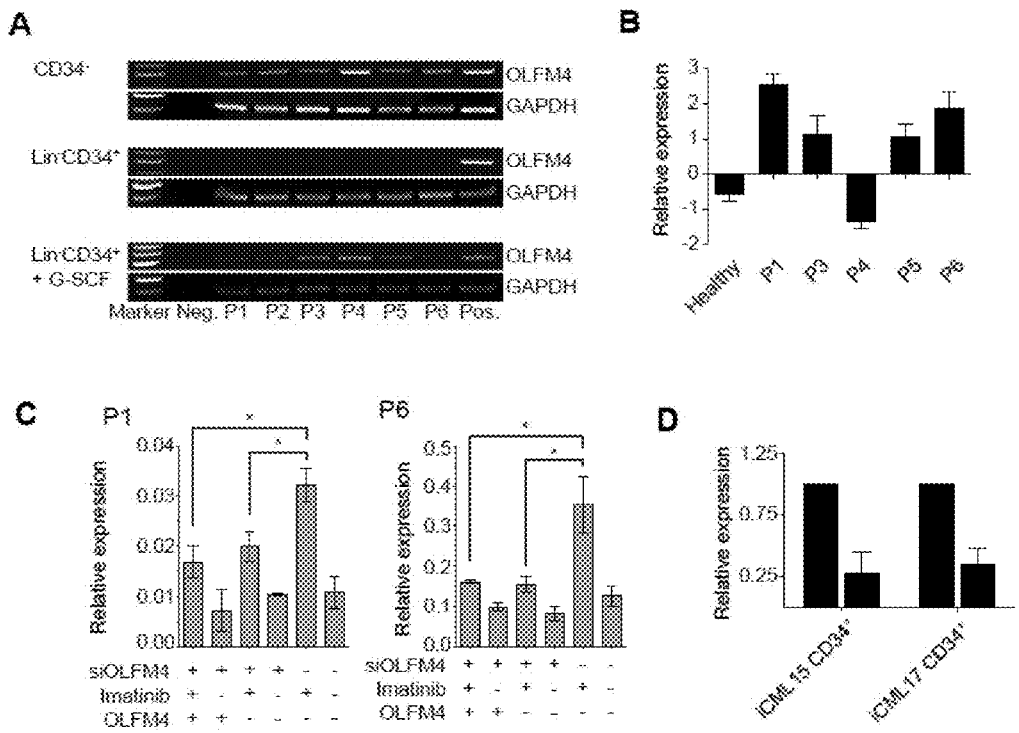
FIG. 9 (A) RT-PCR analysis of OLFM4 expression in sCD34− and sCD34+ cells before and after 24 hours culture with 10 ng/ml G-CSF. Bone marrow mononuclear cells were thawed and cultured 24 hour in serum-free medium. Next day, sCD34+ cells were isolated and cultured for additional 24 hours with or without G-CSF. (B) QPCR analysis demonstrates the augmentation of OLFM4 expression in sCD34+ cells cultured for 24 hours with G-CSF and 5 µM imatinib or DMSO. The expression levels were calculated relative to no imatinib control. (C) The effect of OLFM4 knockdown in sCD34+ cells from patients P1 and P6 on OLFM4 expression in hematopoietic colonies collected from clonogenic culture with or without 5 µM imatinib seven days after transfection. Average expression was normalized to GAPDH. *p<0.05. (D) Efficiency of OLFM4 knockdown with OLFM4 siRNA in iCD34+ cell derived from CML15 iPSCs. QPCR results show the relative level of OLFM4 expression in cells transfected siOLFM4 versus control siRNA.

The $lin^-CD34^+CD45^+$ cells were incubated in SFM supplemented with 1 ng/ml of each SCF, IL-3, IL-6, Flt3L and GM-CSF, with and without 5 μM imatinib for 24 hours. Cells were then washed and resuspended in SFM and plated into either fibronectin- or BSA-coated wells of 96-well plate at $10^3$ cells/well. After two hours, nonadherent and adherent fractions were separated as described (Bhatia et al., 2001; Holtz et al., 2002). Both fractions were plated in serum-containing StemMACS HSC-CFU medium (Miltenyi Biotec, CA), and the percentage of CFCs in adherent fraction was calculated.

siRNA Transfection iPSCs-derived $lin^-CD34^+CD45^+$ cells and somatic CML bone marrow $lin^-CD34^+$ were transfected with 100 nM of either siOLFM4 or scrambled (AllStars Neg. siRNA AF 488) using HiPerfect transfection reagent according to the manufacturer's protocol (all from Qiagen). The transfection efficiency was 50-60% as evaluated by using control ALLStars Neg. siRNA AF488. As determined by QPCR performed 24 hours after transfection, the silencing efficiency was 70-75% (FIG. 9D).

Apoptosis

CML $iCD34^+$ cells were cultured in CSSM containing 10 ng/ml IL3, 100 ng/ml IL6, 200 ng/ml GM-CSF, 100 ng/ml SCF, and 100 ng/ml Flt3L with or without 5 μM imatinib for 24 hours before analysis for apoptosis. When indicated, cells were transfected with OLFM4 or control (scrambled) siRNA. Cells were stained with Annexin-V-PE and 7-aminoactinomycin D (7-AAD) using the Annexin V: PE Apoptosis Detection Kit (BD Bioscience) according to the manufacturer's protocol and analyzed by flow cytometry.

Western Blotting

Cells were cultured in serum-free medium without growth factor in the presence or absence of 5 μM imatinib for four hours prior to harvesting. Lysates were prepared in buffer containing 0.5% Nonidet P-40 (Sigma Diagnostics) and 0.5% sodium deoxycholate supplemented with phenylmethylsulfonyl fluoride (1 mM), protease inhibitors mixture, and phosphatase inhibitors (50 mM NaF, 0.5 mM $Na_3VO_4$). Proteins were resolved on 10% sodium dodecyl sulfate-polyacrylamide gel electrophoresis (SDS-PAGE) gels and transferred to nitrocellulose membrane. Cells were immunoblotted for phospho-CRKL using rabbit polyclonal antibody (Cell Signaling Technology) and horseradish peroxidase- or alkaline phosphatase-conjugated secondary antibodies (Jackson Immuno Research Laboratories). The protein expression level was determined by densitometry with the use of ImageQuant software (Amersham Pharmacia Biotech, Piscataway, N.J.). Each experiment included the CML cell line K562 as a positive control.

Gene Expression Analysis by Real-Time PCR (QPCR)

RNA was isolated from the cell subpopulations using PureLink RNA mini kit (Life Technologies). cDNA synthesis was carried out using Advantage RT-for-PCR kit (Clontech). Quantitative real-time PCR analysis was performed using Gand PlatinumSYBR Green qPCR SuperMix-UDG kit (Life Technologies) and self-designed specific primers for BCR-ABL (forward ACGTTCCTGATCTCCTCTGACTATG (SEQ ID NO:1); reverse TCAGACCCTGAGGCTCAAA (SEQ ID NO:2)), OLFM4 (forward CCAGCTGGAGGTG-GAGATAAG (SEQ ID NO:3); reverse TCAGAGCCAC-GATTTCTCGG (SEQ ID NO:4)) and GAPDH (forward GTGGACCTGACCTGCCGTCT (SEQ ID NO:5); reverse GGAGGAGTGGGTGTCGCTGT (SEQ ID NO:6)).

The reactions were run on a Mastercyclerep Realplex™ thermal cycler (Eppendorf) and expression levels were calculated by minimal cycle threshold values (Ct) normalized to the reference expression of GAPDH in each sample (Pfaffl, 2001). When specified, K562 was used as a reference. All QPCR products were analyzed on 1.2% agarose gels to confirm the specificity of detection.

RNA-Seq Analysis

Total RNA from the subpopulations cells was isolated with PureLink RNA mini kit (Life Technologies) and was subjected to subsequent DNaseI treatment using TURBO DNase™ kit (Ambion). Total RNA was quantitated using the Life Technologies Qubit™ fluorometer (Q32857) and the Agilent Bioanalyzer 2100. Samples were then prepared for sequencing using the Illumina TruSeq RNA Sample Preparation Kit v2™ (RS-122-2001), according to the manufacturer's protocol. Final sample libraries were quantititated with the Life Technologies Qubit™ fluorometer and sequenced on the Illumina HiSeq 2500 (SY-401-1003-PRE). Base-calling and demultiplexing were done with the Illumina Genome Analyzer Casava Software™, version 1.8.2. After quality assessment and filtering for adapter molecules and other sequencing artifacts, the remaining sequencing reads were aligned to 19084 RefSeq genes extracted from the Illumina iGenomes annotation, selecting only "NM_" designated genes. Bowtie v 0.12.9 was used, allowing two mismatches in a 28 bp seed, and excluding reads with more than 200 alignments (Langmead et al., 2009). RSEM v 1.2.3 was used to estimate isoform or gene relative expression levels in units of "transcripts per million" (tpm) (Li and Dewey, 2011; Li et al., 2010). Samples were hierarchically clustered on a set of 2855 genes (selected for a minimum TPM of 2.0 in at least one sample, and a minimum fold change of 2.0 between highest and lowest TPM). The samples were clustered using (1-(Spearman rank correlation coefficient)) as the distance metric between each pair of samples. The average distance between each cluster pair was used as the basis to merge lower-level clusters into higher-level clusters. To determine differentially expressed genes, RNAseq output data were analyzed using EBseq(v. 1.1.6) (Leng et al., 2013) which is available on the internet at the following address: biostat.wisc.edu/~kendzior/EBSEQ/. Genes with posterior probability equal to 1.000 were considered differentially expressed. Only genes with tpm≥10 were selected for further analysis. Genes that demonstrated significant differences in expression between studied groups were assigned to biological process categories using DAVID bioinformatics program. (Huang da et al., 2008) To visualize the gene-expression levels, a heatmap was composed using MultiExperiment Viewer v4.2 available on the internet at the following address: www.tm4.org.

Statistical Analysis

Data obtained from multiple experiments were reported as the mean±SEM. Significance levels were determined by one-tailed Student-t test analysis.

Example 2

Induced LSC-Like Cells are Resistant to BCR-Abl Inhibition by Imatinib

Figures 3A, 3B, 3C, 3D:
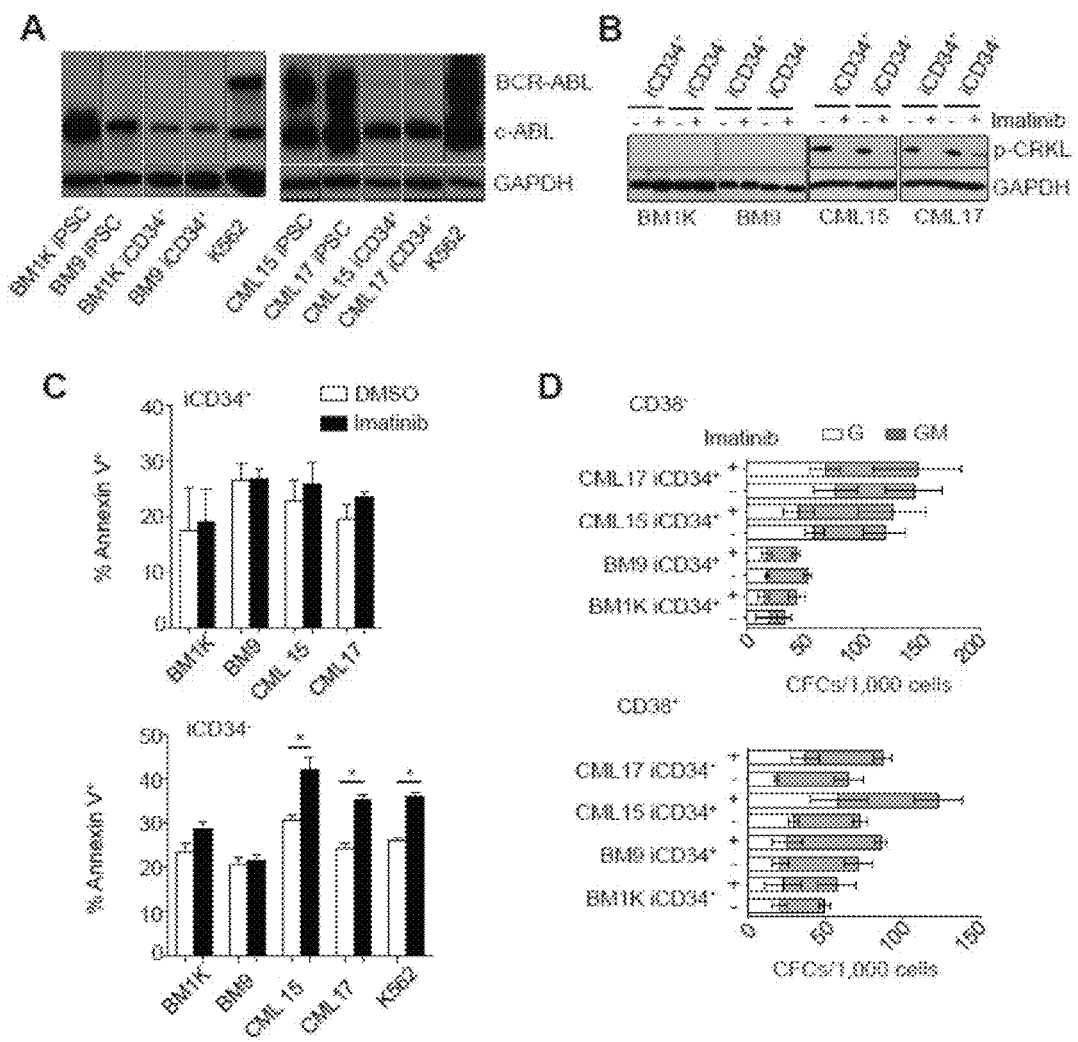
FIG. 3 The effect of imatinib effect on CML $iCD34^+$ cells. (A) Western blot showed expression of BCR-ABL protein in normal BM iPSCs and CML iPSCs and their hematopoietic derivatives. GAPDH and K562 were used as a loading control and a positive control respectively. (B) Western blotting shows phospho-CRKL (p-CRKL) level in $iCD34^+$ and $iCD34^-$ cells in the presence or absence of imatinib. GAPDH was used as a loading control. (C) Apoptosis in BM and CML $iCD34^+$ and $iCD34^-$ cells treated and non-treated with 5 µM imatinib for 24 hours. Apoptosis was evaluated by annexin V staining. Results are the mean±SEM from three independent experiments. K562 was used as an IM-sensitive control. * $p<0.05$. (D) Myeloid colony formation from CML and BM $iCD34^+CD38^-$ and $iCD34^+CD38^+$ cells cultured in clonogenic medium with or without 10 µM imatinib. Results are the mean±SEM of three independent experiments. (E) 50% Inhibition concentration ($IC_{50}$) assay from BM and CML $iCD34^+$, and $iCD34^-$ cells is shown as relative response versus log concentration of imatinib. * indicates significant 1050 shift ($p<0.05$). Results are the mean±SEM from three experiments performed in triplicate.
Figure 3E:
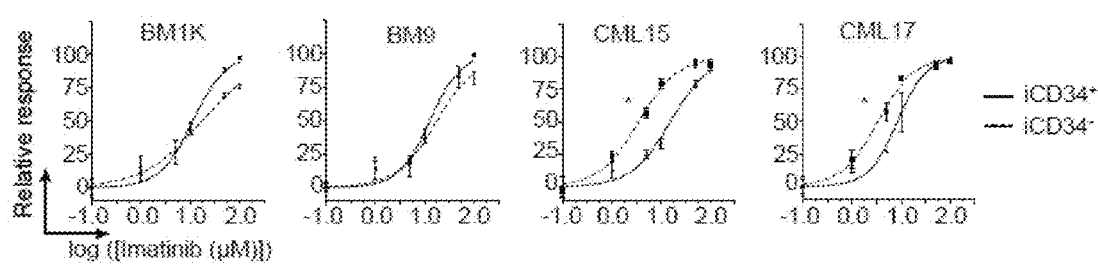
Figures 8A, 8B, 8C:
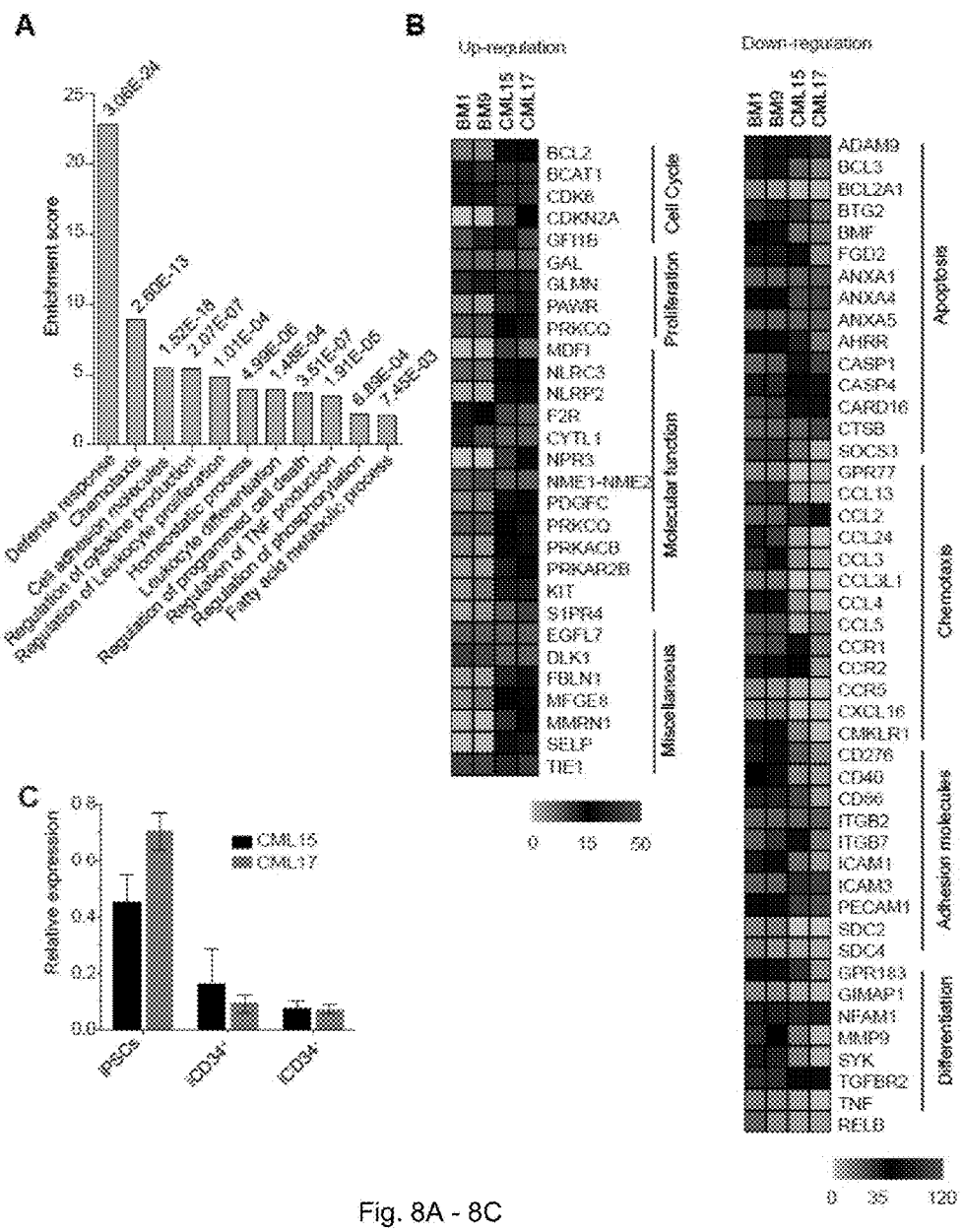
FIG. 8 (A) The 922 differentially expressed genes between CML versus BM iCD34+ cells showing ≥2 fold change were classified into biological process defined by Gene Ontology (GO) Term using DAVID program. Representative clusters are shown in a histogram along with p-Value. (B) Heat maps show selected up-regulated and down-regulated genes in CML iCD34+ within identified GO categories. The gene expression levels are estimated in tpm. (C) QPCR quantification of BCR-ABL mRNA expression in CML iPSCs and their derivatives. The expression levels were calculated relative to K562 as calibrator. Results are mean±SEM from three experiments in duplicate.

The dependence of CML cells on BCR-ABL signaling enable the suppression of the disease by TKIs and the long-term survival of the patients. However, resistances of CML LSCs to imatinib preclude a complete cure of CML (Bhatia et al., 2000; Corbin et al., 2011; Jiang et al., 1999; Verfaillie et al., 1992). Analysis of BCR-ABL expression by PCR and western blot demonstrated that BCR-ABL mRNA and protein were present in undifferentiated iPSCs and their iCD34$^+$ and iCD34$^-$ progeny (FIG. 3A and FIG. 8C). Evaluation of the phosphorylation status of the BCR-ABL-specific substrate CRK-like protein (CRKL) revealed the expression of a phosphorylated form of CRKL (p-CRKL) in CML but not in the control BM iCD34$^+$ and iCD34$^-$ cells (FIG. 3B), providing evidence that BCR-ABL is active in CML iPSC-derived hematopoietic progeny. After treatment with imatinib, p-CRKL dramatically decreased in both primitive iCD34$^+$ and in more mature iCD34$^-$ blood cells indicating that imatinib efficiently inhibits kinase activity in de novo generated CML cells independently of the stage of maturation. Studies in CML patients have shown that imatinib inhibits BCR-ABL kinase in primitive hematopoietic cells and their proliferation without affecting survival of LSCs (Copland et al., 2006; Corbin et al., 2011; Graham et al., 2002; Holtz et al., 2002; Schemionek et al., 2010). To find out whether de novo generated CML iCD34$^+$ cells respond to imatinib in a similar fashion, we evaluated the effect of imatinib on these cells in vitro. Although treatment of cells with imatinib reversed enhanced proliferation of CML iCD34$^+$ (FIG. 2B), as observed with somatic LSCs (Corbin et al., 2011), imatinib failed to induce apoptosis in these cells or inhibit CFCs from CML iCD34$^+$ cells (FIGS. 3C and 3D). In contrast, mature iCD34$^-$ cells showed significant increased sensitivity to imatinib as determined using Annexin V staining (FIG. 3C) and maximal inhibitory concentration 50% ($IC_{50}$) assay (FIG. 3E). To confirm the maturation stage-dependent sensitivity we analyzed the distribution of apoptotic cells within different compartments and generations following expansion of CFSE-labeled iCML CD34$^+$ cells (FIG. 4). Imatinib treatment of iCML CD34$^+$ cultures was associated with retention of CD34$^+$ cells in generations 2-6. On the other hand, non-treated cells showed gradual and substantial loss of CD34 expression and predominance of CD34$^-$ cells within the rapidly dividing compartment. Staining of CFSE cultures with annexin V revealed that the most primitive iCD34$^{bright}$ cells were resistant to imatinib-induced apoptosis regardless of proliferative potential, while substantial increase in apoptosis was observed in more mature iCD34$^{dim}$ and iCD34$^-$ cells treated with imatinib. This implies that differentiated CML iCD34$^-$ cells became sensitive to imatinib and do not survive in the cultures, while CML primitive iCD34$^+$ cells did not undergo apoptosis upon imatinib treatment and are selected to dominate in culture.

Taken together, these results indicated that CML iCD34$^+$ cells reproduce many aspects of drug resistance observed in somatic primitive hematopoietic cells from CML patients in the chronic phase.

Example 3

Identification of Olfactomedin 4 as a Novel Drug Target in LSC-Like Cells

To find out whether iPSC-derived primitive CML hematopoietic cells can be used to discover novel drug targets, we performed molecular profiling of CML and control BM iCD34+ cells treated or non-treated with imatinib. Similar to findings in somatic CML CD34+ cells (Bruns et al., 2009; Diaz-Blanco et al., 2007), untreated CML iCD34+ showed significant differences in expression of genes regulating cell adhesion and chemotaxis, proliferation, programmed cell death and fatty acid metabolism as compared to controls (FIG. 8A), including upregulation of genes associated with cancer development such as BCL2, CDK6, PRKCQ, MYCN, TP53RK, and RASGRP3 and downregulation of adhesion molecules ICAM1, ICAM3, ITGB2 and ITGB7 (FIG. 8B and Appendix). After treatment with 5 µM imatinib, the molecular profile of CML iCD34$^+$ cells became more similar to control BM iCD34+ cells, consistent with the critical role of BCR-ABL signaling in establishing a unique transcriptional signature of neoplastic cells in CML (FIG. 5E).

Figures 5A, 5B:
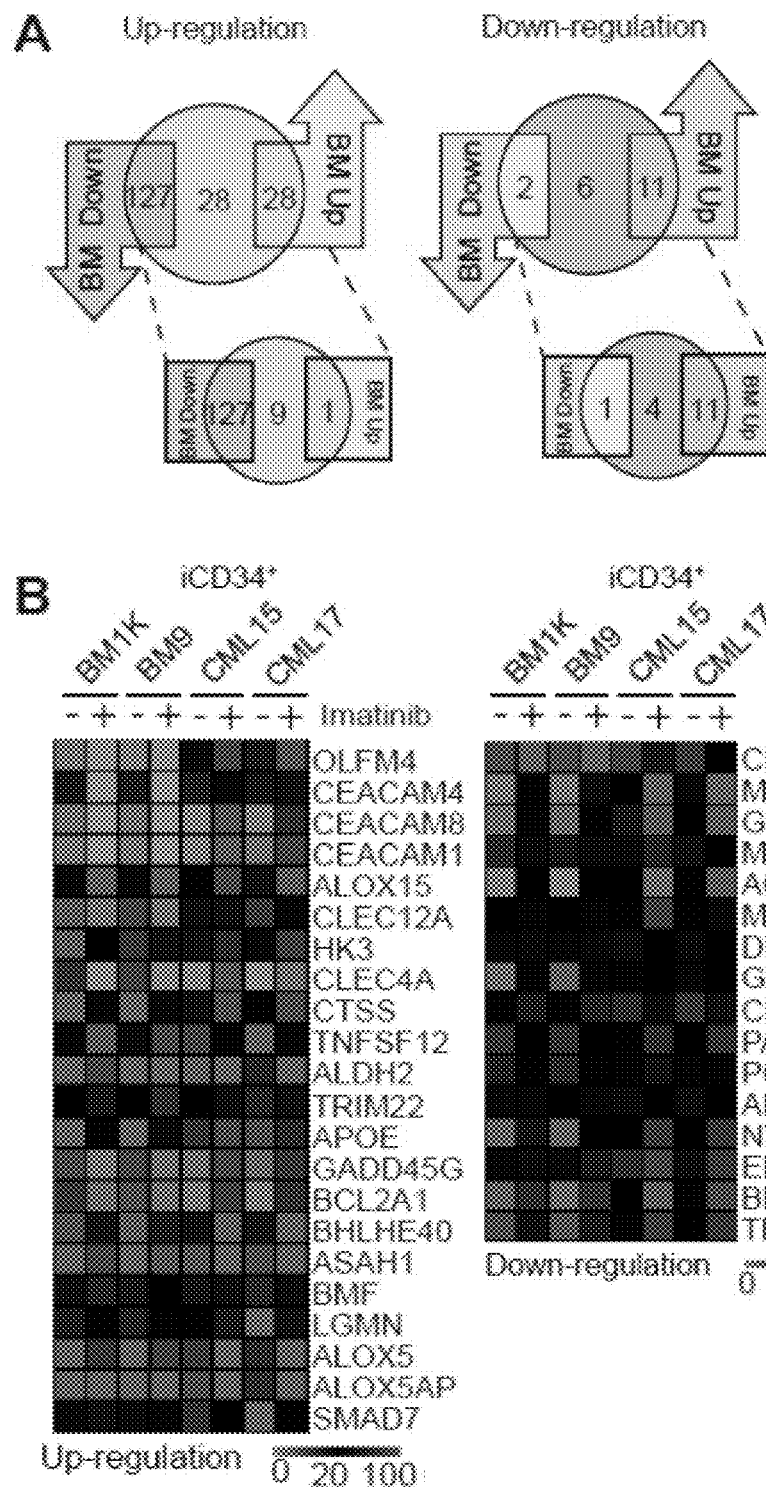
FIG. 5 Gene expression analysis reveals set of imatinib-induced genes in CML $iCD34^+$ cells. (A) The algorithm used to find candidate genes associated with imatinib resistance. Upper left Venn diagram on the left shows genes induced by imatinib in CML $iCD34^+$ (≥2 fold induction), but not in control BM iCD34+ cells. Lower left Venn diagram excludes from this group genes that expressed in imatinib-treated CML iCD34+ cells at a lower level as compared to imatinib-treated BM iCD34+ cells. Upper right Venn diagram shows genes that were suppressed ≥2 fold by imatinib in CML iCD34+, but not in control BM iCD34+ cells. Lower right Venn diagram excludes from this group genes that expressed at higher levels in imatinib-treated CML iCD34+ compared to imatinib-treated BM iCD34+ cells. (B) Heat maps show expression of genes selectively induced or suppressed by imatinib in CML iCD34+. The top genes arranged based on ratio of expression in imatinib-treated CML/imatinib-treated BM iCD34+ cells are shown. (C) Expression of OLFM4 in CML and BM iCD34+ as determined by QPCR. The expression level was calculated relative to the sample GAPDH. The results are mean±SEM of three experiments in duplicate. (D) QPCR analysis of the effect of imatinib treatment on expression of OLFM4 in CML and BM iCD34+ cells. The results are mean±SEM of three experiments in duplicate. The expression levels were calculated relative to untreated control. (E) Spearman rank correlation of global gene expression in iCD34+ cells treated and non-treated with imatinib. (F) Colony formation (G+GM) by iCD34+ cells transfected with either siOLFM4 siRNA or negative control siRNA (scrambled) and DMSO and cultured in clonogenic medium with 10 µM imatinib or DMSO (control). Results are the means±SEM of three independent experiments. (G) Effect of OLFM4 knockdown on iCD34+ cell proliferation in CSSM medium supplemented with growth factors. Percentages of cells in OLFM4 siRNA-treated cultures relative to corresponding control scrambled siRNA-treated BM or CML iCD34+ cultures are shown. Results are mean±SEM of three independent experiments. * p<0.05 as compare to control. (H) OLFM4 knockdown with siRNA induces apoptosis in imatinib treated CML iCD34+ cells. Results are mean±SEM of three independent experiments. * p<0.05. See also FIG. 8.
Figures 5C, 5D, 5E, 5F:
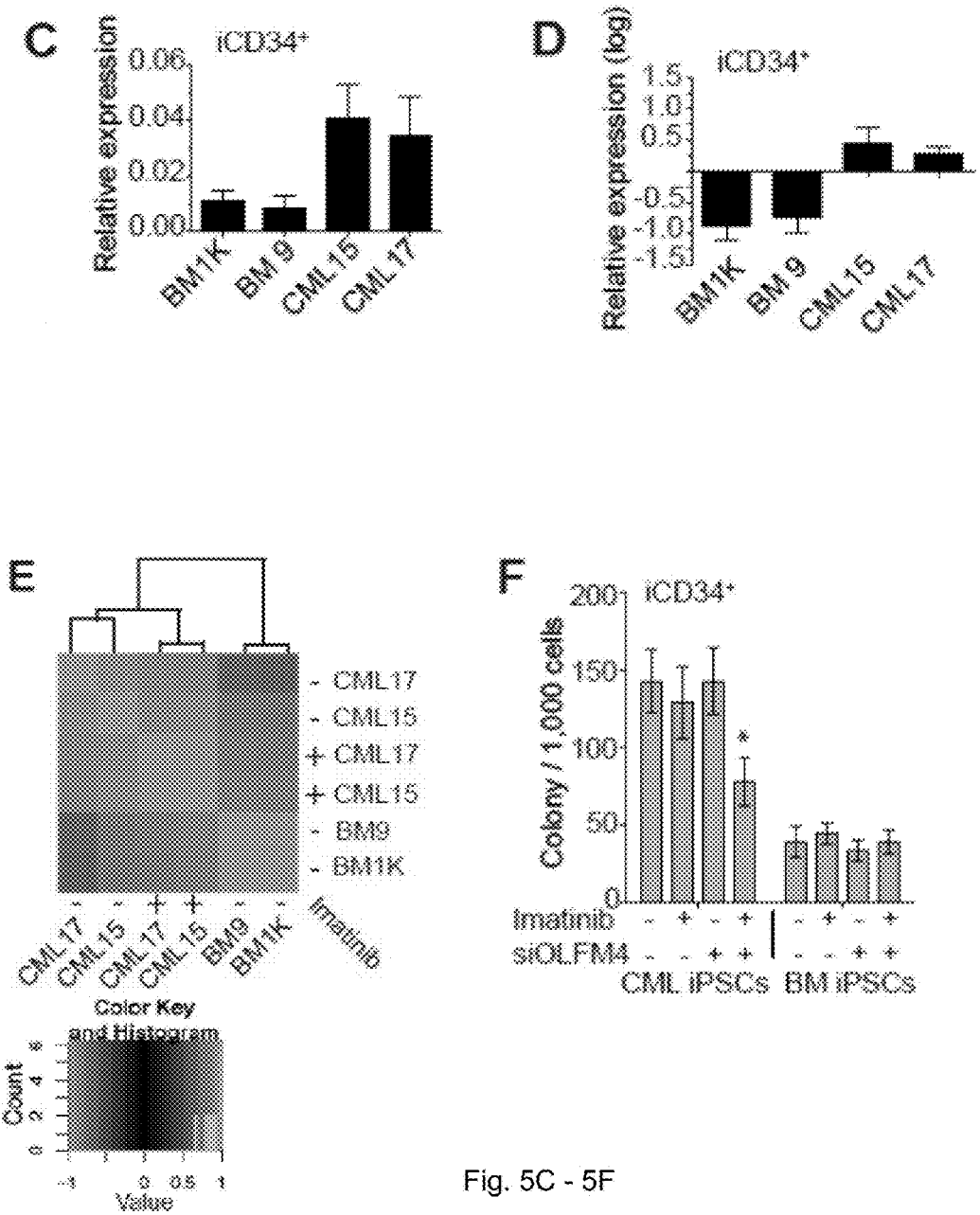
Figure 5G:
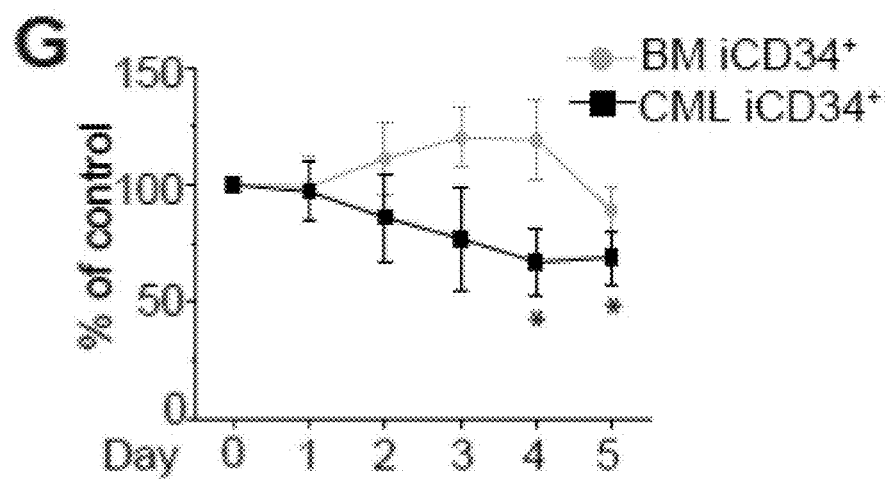
Figure 5H:
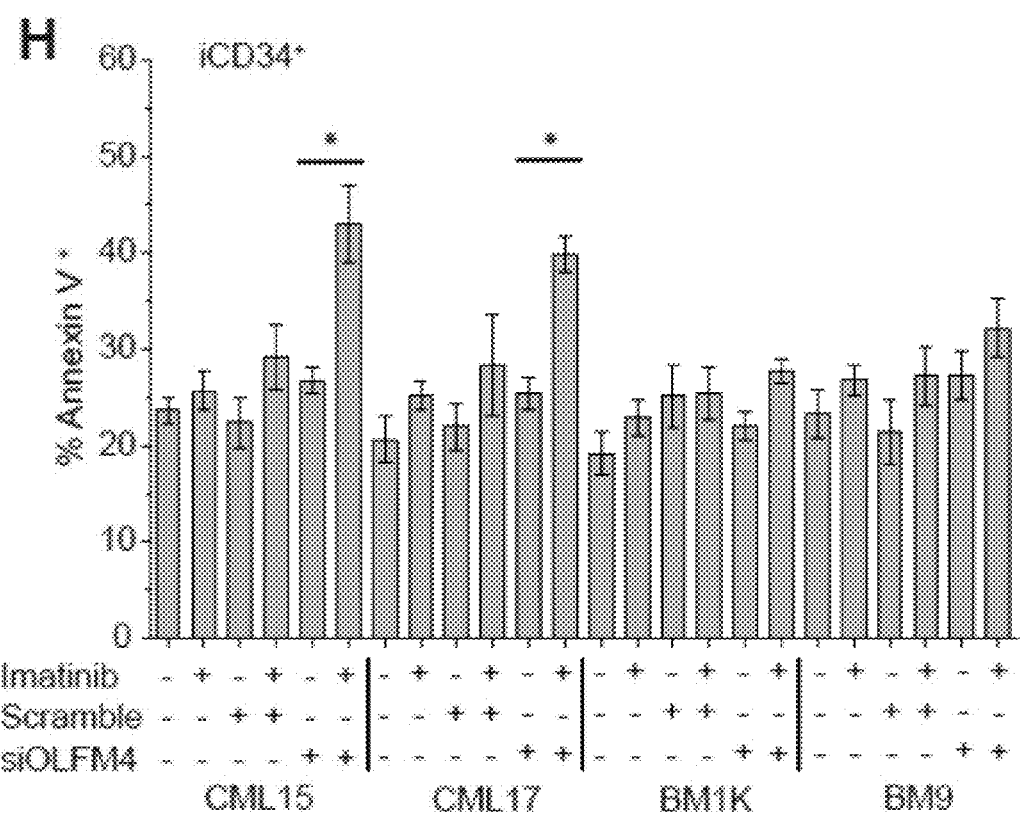

To find candidate genes associated with imatinib resistance, we designed an algorithm to select genes that are specifically induced or suppressed by imatinib in CML iCD34+ cells (FIG. 5A). First we chose genes induced by imatinib in CML iCD34$^+$ (2 fold induction), but not in control BM iCD34$^+$ cells. Then we excluded from this group genes that expressed in imatinib-treated CML iCD34$^+$ cells at a lower level as compared to imatinib-treated BM iCD34$^+$ cells. A similar algorithm was applied for down-regulated genes. First we chose genes that were suppressed ≥2 fold by imatinib in CML iCD34$^+$, but not in control BM iCD34+ cells. Then we excluded from this group genes that expressed at higher levels in imatinib-treated CML iCD34$^+$ compared to imatinib-treated BM iCD34+ cells. Based on this algorithm we identified 127 genes selectively upregulated and eleven genes selectively downregulated following imatinib treatment (FIGS. 5A and 5B and Appendix). Interestingly, one of the top-ranking up-regulated genes on this list was OLFM4 (olfactomedin 4), which has been reported to have anti-apoptotic activity in malignancy (Liu et al., 2012; Oh et al., 2011; Zhang et al., 2004). After QPCR analysis confirmed the high level of OLFM4 expression in CML iCD34+ and augmentation of OLFM4 expression by imatinib (FIGS. 5C and 5D), we tested the effect of OLFM4 knocking-down using OLFM4-targeted small interference RNA on iCD34+ cell apoptosis. As shown in FIG. 5H, treatment of cells with siOLFM4 selectively induced apoptosis in imatinib-treated CML but not in BM iCD34$^+$ cells, indicating that this gene could be important for survival of primitive CML cells. In addition, OLFM4 siRNA significantly inhibited CML iCD34$^+$ CFCs and proliferation (FIGS. 5F and 5G).

Figures 6A, 6B:
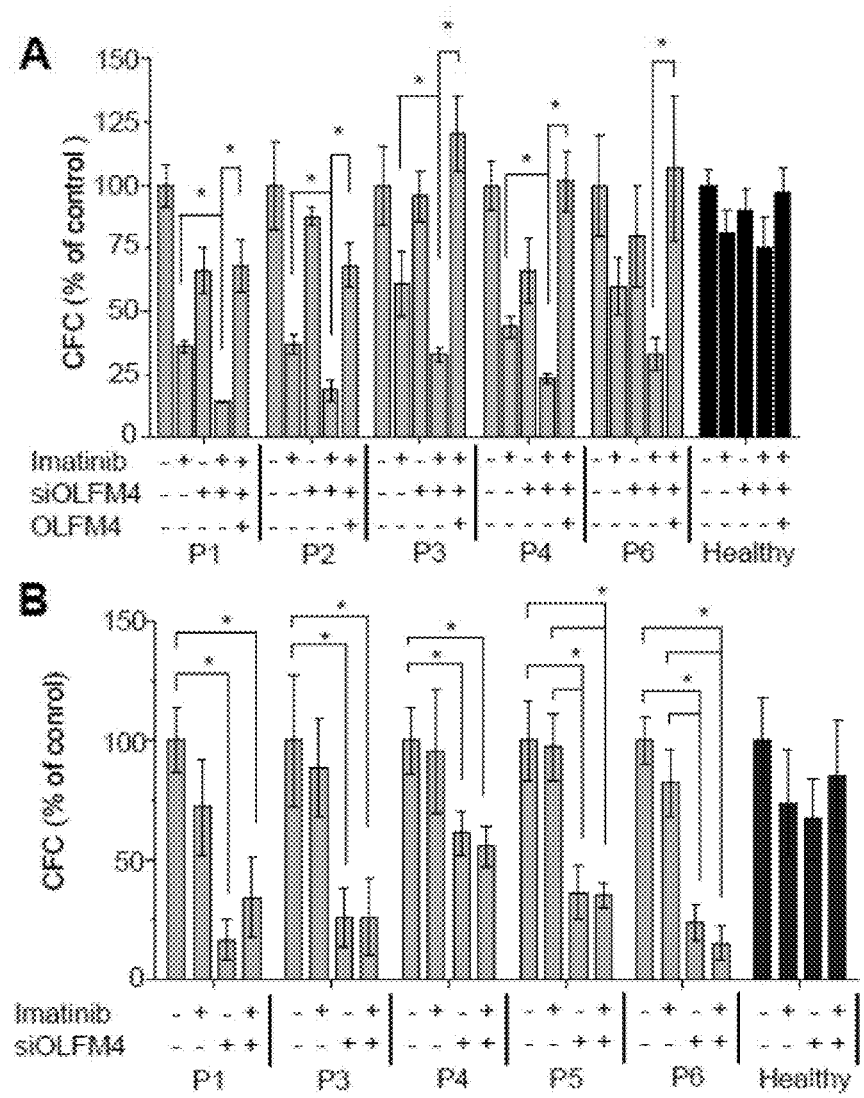
FIG. 6 Effect of OLFM4 on somatic CML LSCs. (A) Knockdown of OLFM4 potentiates inhibitory effect of imatinib on CML sCD34+ CFCs (G+GM). After transfection with siOLFM4 or negative control siRNA, CML or healthy control sCD34+ were cultured with or without 5 µM imatinib in presence or absence of OLFM4 protein (300 ng/ml) for 24 hours in serum-free medium with low growth factors and transferred to clonogenic medium. Results are the mean±SEM of three to five independent experiments. (B) Knock-down of OLFM4 with siRNA dramatically reduced CFC output in LTC-IC cultures of CML patients but not in healthy controls. Results are mean±SEM of three experiments. * p<0.05. (C) OLFM4 (300 ng/ml) potentiates expansion of sCD34+ cells in serum-free medium without growth factors. Results are mean±SEM of three experiments. P1-P6 indicates individual patients with CML in chronic phase. (D) The hypothetical model of OLFM4 action on CML LSCs. OLFM4 produced by differentiated CD34− cells supports LSC survival and expansion. Increased production of G-SCF within BM microenvironment and exposure of cells to imatinib induces OLFM4 expression in LSCs. OLFM4 acts in autocrine fashion as a survival mechanism in CML LSCs allowing them to escape from imatinib-induced death. See also FIG. 9.
Figures 6C, 6D:
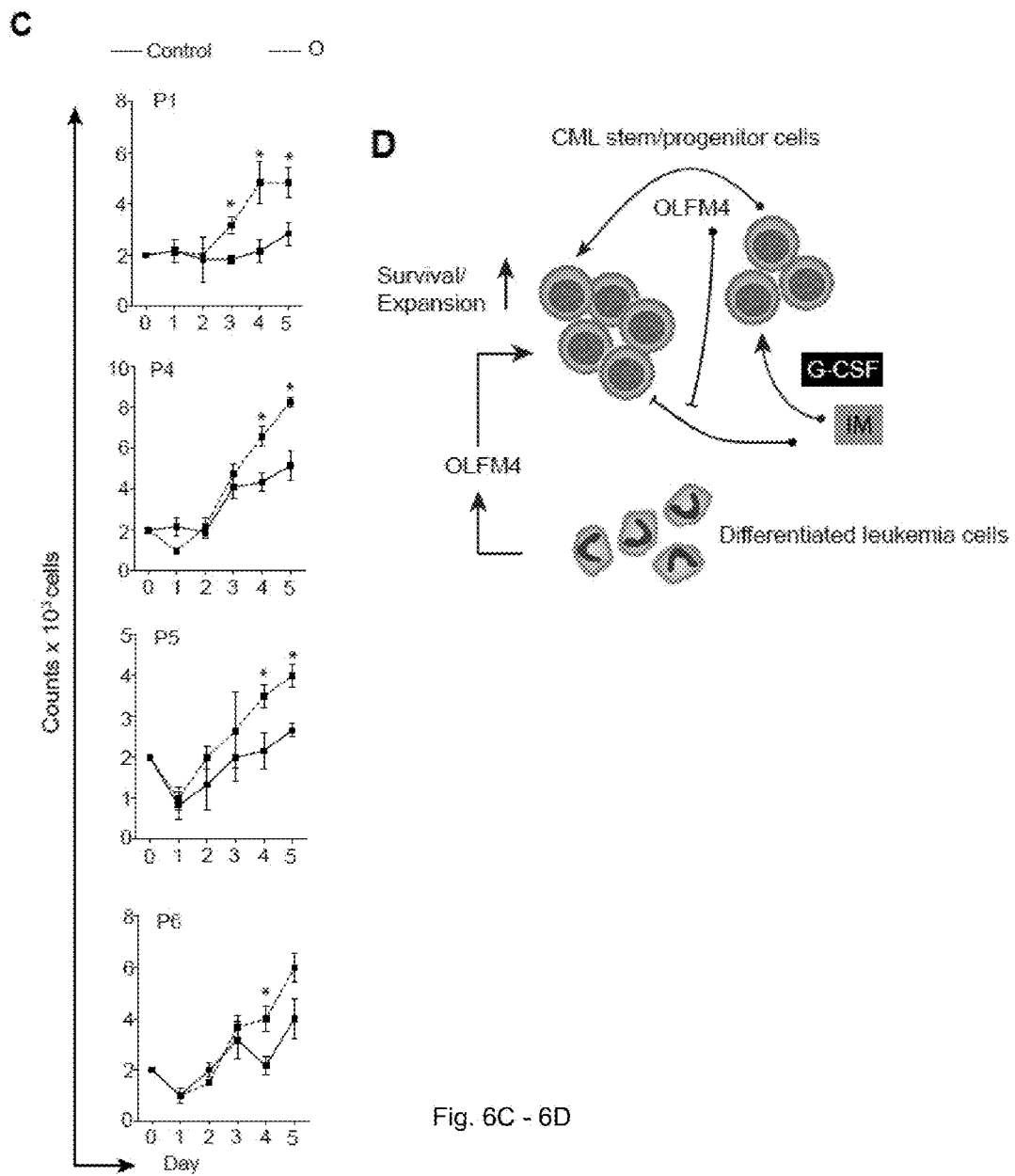

To find out whether these findings can be translated to somatic cells, we evaluated the expression and functional role of OLFM4 in somatic CD34$^+$ cells obtained from parental bone marrow and bone marrow from the other six CML patients in the chronic phase. We found a high level of OLFM4 expression in somatic CD34$^-$ (sCD34$^-$) bone marrow cells. Somatic lin-CD34$^+$ CML (sCD34$^+$) expressed a low level of OLFM4. OLFM4 expression was down-regulated when sCD34$^+$ cultured overnight in serum-free medium. However, OLFM4 expression was rapidly induced in sCD34$^+$ cells after treatment with G-CSF (FIG. 9A). While imatinib alone was not able to induce OLFM4, it substantially enhanced G-CSF-induced OLFM4 expression in all but one patient (FIG. 9B). Upregulation of OLFM4 by imatinib was also observed in clonogenic medium. Knockdown of OLFM4 in sCD34$^+$ cells using siRNA significantly suppressed OLFM4 expression in hematopoietic colonies (FIG. 9C) and potentiated inhibitory effect of imatinib on CFCs, which can be reversed by pretreatment of cells with OLFM4 (FIG. 6A). We also found that adding OLFM4 protein to the medium enhanced proliferation of sCD34$^+$ cells in serum-free cultures without cytokines, indicating that OLFM4 supports growth factor-independent proliferation of primitive leukemia cells (FIG. 6C). To determine the effect of OLFM4 knockdown on cells more primitive than CFCs, we performed LTC-IC assay using siOLFM4 treated CML sCD34$^+$ cells. Consistent with previous studies with somatic CML LSCs (Corbin et al., 2011), imatinib had little effect on LTC-ICs. However, treatment of sCD34$^+$ cells with OLFM4 siRNA significantly reduced the number of LTC-ICs in all studied patients (FIG. 6B), indicating that OLFM4 is important for survival of CML LSCs.

Multiple studies have already demonstrated the validity of the iPSC model for studying pathogenesis of monogenic human diseases and drug screening (reviewed in (Rais et al., 2013)). Although the potential use of iPSCs technology in studying neoplasia has been suggested (Ramos-Mejia et al., 2012; Slukvin, 2009; Ye et al., 2009), only a few groups have reported the generation of iPSCs from malignant cells. The first successful reprogramming of cancer cells has been achieved by (Hochedlinger et al., 2004), who generated mouse pluripotent stem cells by transplanting nuclei from melanoma into oocytes. After discovery of pluripotency factors capable of reprogramming blood cells, iPSC lines have been generated from a patient with myeloproliferative disorder bearing JAK2-V617F mutation (Ye et al., 2009), CML cell lines (Carette et al., 2010), primary bone marrow cells obtained from CML patients in the chronic phase (Hu et al., 2011; Kumano et al., 2012), juvenile myelomonocytic leukemia (Gandre-Babbe et al., 2013) and mouse MLL-AF9 leukemia cells (Liu et al., 2013). These studies demonstrated that iPS cells generated from neoplastic cells carry a disease-specific genetic mutation and can generate blood cells affected by that particular mutation. Here, we advanced the iPSC model to study primitive leukemia cells and prove the utility of this model for discovering drug targets by identifying the novel CML LSC survival factor OLFM4. Human OLFM4 (also called GW112 and hGC-1) gene encodes a secreted glycoprotein with a multimer structure (Liu et al., 2006) that plays an important role in a variety of cellular functions including cell adhesion, cell cycle and apoptosis (Tomarev and Nakaya, 2009). In the human intestine, OLFM4 was identified as a robust marker of LGR5$^+$ stem cells and a subset of cancer cells (van der Flier et al., 2009). OLFM4 is involved in cell growth and apoptosis in human malignancies (Liu et al., 2010; Oh et al., 2011; Park et al., 2012; Zhang et al., 2004) and is considered to be an inducible resistance factor to apoptotic stimuli (Koshida et al., 2007). OLFM4 interacts with GRIM-19 (Zhang et al., 2004), which is a component of respiratory complex I of mitochondria with anti-apoptotic role in prostate cancer cells (Huang et al., 2004). However, OLFM4 effects on apoptosis appear to be a cell-type dependent. Although OLFM4 was initially identified in myeloblasts and later in neutrophils (Clemmensen et al., 2012; Zhang et al., 2002), OLFM4's biological function in normal and neoplastic hematopoiesis remains largely unknown. It has been shown that OLFM4 expression is upregulated in a subset of patients with acute myeloid leukemia and that overexpression of OLFM4 in HL-60 leukemia cell line induces their differentiation and apoptosis (Liu et al., 2010). Here, we demonstrated that OLFM4 is expressed in CD34$^-$ CML bone marrow cells and is induced in CML LSCs by G-CSF. OLFM4-mediated autocrine and paracrine signaling supports LSC survival (see model in FIG. 6D). Because imatinib treatment enhances OLFM4 expression in cytokine-primed primitive CML cells, it may provide a favorable microenvironment for CML LSC survival in TKI-treated patients.

In conclusion, we demonstrate the validity of the iPSC model for studying CML LSCs. Further exploration of this model will be valuable in studying acquired drug resistance, diversity of genetic alterations within tumors, and the epigenetic mechanisms of leukemogenesis.

Example 4

Inhibition of LSC Proliferation in Xenografts by OLFM4 Knockdown

Sorted lin$^-$CD34$^+$ cells from CML bone marrow were transduced with either AllStars Negative control or OLFM4 siRNA for 24 hours. Cells were then washed and transplanted into Nod scid gamma (NSG) mice at 5-10×10$^3$ cells. Four mice were injected with cells treated with control siRNA and four mice were injected with OLFM4 siRNA. The mice were then analyzed at 16 weeks using flow cytometry for live human CD45$^+$ cells in bone marrow, liver, spleen, and peripheral blood.

Samples from mice that showed detectable human CD45 cells were pooled and cultured in serum-free media supplemented with cytokines (IL3, 6 and SCF at 10, 100, 100 ng/ml) for 1 week. The cultured cells were labeled with human CD45, mouse CD45 and DAPI and sorted for live human CD45$^+$ mouse CD45$^-$ cells. The sorted cells were then plated in methyl cellulose media for hematopoietic progenitor assay and RNA extracted for PCR.

Figures 10A, 10B, 10C:
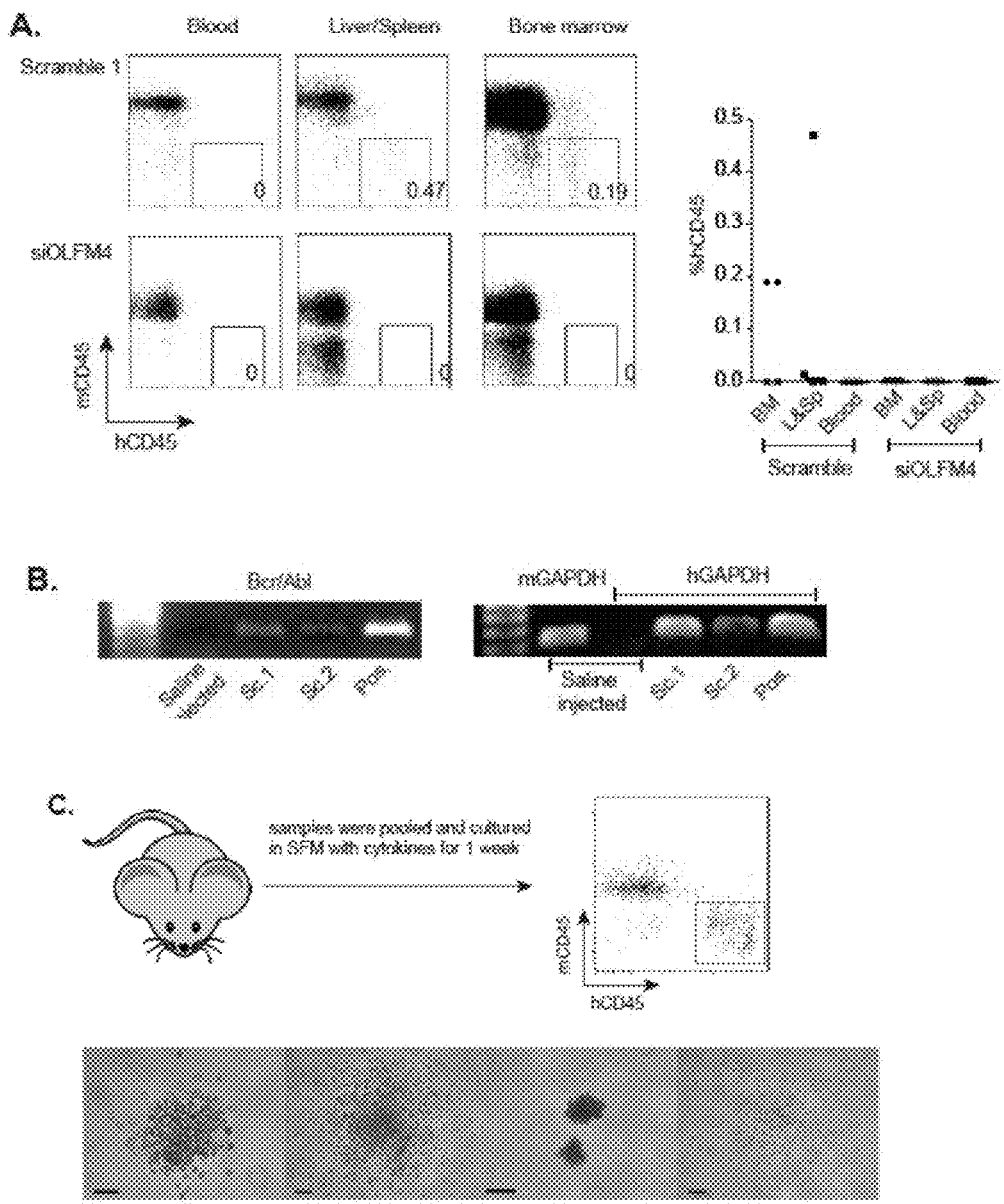
FIG. 10 (A) Dot plot shows representative animal transplanted with scramble or siOLFM4 transduced CML cell at 16th week. Scatter plot shows percentage of live human CD45+ mouse CD45− cells in individual animals. 2 out 4 control animals show engraftment, while none of the animals treated with OLFM4 showed engraftment. L&Sp=liver and spleen. (B) PCR from cDNA of live human CD45+ mouse CD45− cells sorted from positive animals showing Bcr/Abl rearrangement. (C) Schematic overview of the procedure of live human cell isolation from animals and colony-forming activity of live human CD45+ and mouse CD45− cells.

As shown in FIG. 10 two out of four control animals show engraftment, while none animal treated with OLFM4 siRNA showed engraftment

REFERENCES CITED IN EXAMPLES SECTION

Bhatia, R., Munthe, H. A., and Forman, S. J. (2001). Abnormal growth factor modulation of beta1-integrin-mediated adhesion in chronic myelogenous leukaemia haematopoietic progenitors. Br J Haematol 115, 845-853.

Bhatia, R., Munthe, H A, Williams, A. D., Zhang, F., Forman, S. J., and Slovak, M. L. (2000). Chronic myelogenous leukemia primitive hematopoietic progenitors demonstrate increased sensitivity to growth factor-induced proliferation and maturation. Exp Hematol 28, 1401-1412.

Bruns, I., Czibere, A., Fischer, J. C., Roels, F., Cadeddu, R. P., Buest, S., Bruennert, D., Huenerlituerkoglu, A. N., Stoecklein, N. H., Singh, R., et al. (2009). The hematopoietic stem cell in chronic phase CML is characterized by a transcriptional profile resembling normal myeloid progenitor cells and reflecting loss of quiescence. Leukemia 23, 892-899.

Carette, J. E., Pruszak, J., Varadarajan, M., Blomen, V. A., Gokhale, S., Camargo, F. D., Wernig, M., Jaenisch, R., and Brummelkamp, T. R. (2010). Generation of iPSCs from cultured human malignant cells. Blood 115, 4039-4042.

Choi, K. D., Vodyanik, M. A., and Slukvin, I I (2009a). Generation of mature human myelomonocytic cells through expansion and differentiation of pluripotent stem cell-derived lin-CD34+CD43+CD45+ progenitors. J Clin Invest 119, 2818-2829.

Choi, K. D., Yu, J., Smuga-Otto, K., Salvagiotto, G., Rehrauer, W., Vodyanik, M., Thomson, J., and Slukvin, I. (2009b). Hematopoietic and endothelial differentiation of human induced pluripotent stem cells. Stem Cells 27, 559-567.

Clemmensen, S. N., Bohr, C. T., Rorvig, S., Glenthoj, A., Mora-Jensen, H., Cramer, E. P., Jacobsen, L. C., Larsen, M. T., Cowland, J. B., Tanassi, J. T., et al. (2012). Olfactomedin 4 defines a subset of human neutrophils. J Leukoc Biol 91, 495-500.

Copland, M., Hamilton, A., Elrick, L. J., Baird, J. W., Allan, E. K., Jordanides, N., Barow, M., Mountford, J. C., and Holyoake, T. L. (2006). Dasatinib (BMS-354825) targets an earlier progenitor population than imatinib in primary CML but does not eliminate the quiescent fraction. Blood 107, 4532-4539.

Corbin, A. S., Agarwal, A., Loriaux, M., Cortes, J., Deininger, M. W., and Druker, B. J. (2011). Human chronic myeloid leukemia stem cells are insensitive to imatinib despite inhibition of BCR-ABL activity. J Clin Invest 121, 396-409.

Diaz-Blanco, E., Bruns, I., Neumann, F., Fischer, J. C., Graef, T., Rosskopf, M., Brors, B., Pechtel, S., Bork, S., Koch, A., et al. (2007). Molecular signature of CD34(+) hematopoietic stem and progenitor cells of patients with CML in chronic phase. Leukemia 21, 494-504.

Druker, B. J., Guilhot, F., O'Brien, S. G., Gathmann, I., Kantarjian, H., Gattermann, N., Deininger, M. W., Silver, R. T., Goldman, J. M., Stone, R. M., et al. (2006). Five-year follow-up of patients receiving imatinib for chronic myeloid leukemia. N Engl J Med 355, 2408-2417.

Druker, B. J., Talpaz, M., Resta, D. J., Peng, B., Buchdunger, E., Ford, J. M., Lydon, N. B., Kantarjian, H., Capdeville, R., Ohno-Jones, S., et al. (2001). Efficacy and safety of a specific inhibitor of the BCR-ABL tyrosine kinase in chronic myeloid leukemia. N Engl J Med 344, 1031-1037.

Gandre-Babbe, S., Paluru, P., Aribeana, C., Chou, S. T., Bresolin, S., Lu, L., Sullivan, S. K., Tasian, S. K., Weng, J., Favre, H., et al. (2013). Patient-derived induced pluripotent stem cells recapitulate hematopoietic abnormalities of juvenile myelomonocytic leukemia. Blood 121, 4925-4929.

Graham, S. M., Jorgensen, H. G., Allan, E., Pearson, C., Alcorn, M. J., Richmond, L., and Holyoake, T. L. (2002). Primitive, quiescent, Philadelphia-positive stem cells from patients with chronic myeloid leukemia are insensitive to STI571 in vitro. Blood 99, 319-325.

Grskovic, M., Javaherian, A., Strulovici, B., and Daley, G. Q. (2011). Induced pluripotent stem cells—opportunities for disease modelling and drug discovery. Nat Rev Drug Discov 10, 915-929.

Holtz, M. S., Slovak, M. L., Zhang, F., Sawyers, C. L., Forman, S. J., and Bhatia, R. (2002). Imatinib mesylate (STI571) inhibits growth of primitive malignant progenitors in chronic myelogenous leukemia through reversal of abnormally increased proliferation. Blood 99, 3792-3800.

Holyoake, T., Jiang, X., Eaves, C., and Eaves, A. (1999). Isolation of a highly quiescent subpopulation of primitive leukemic cells in chronic myeloid leukemia. Blood 94, 2056-2064.

Holyoake, T. L., Jiang, X., Jorgensen, H. G., Graham, S., Alcorn, M. J., Laird, C., Eaves, A. C., and Eaves, C. J. (2001). Primitive quiescent leukemic cells from patients with chronic myeloid leukemia spontaneously initiate factor-independent growth in vitro in association with upregulation of expression of interleukin-3. Blood 97, 720-728.

Hu, K., Yu, J., Suknuntha, K., Tian, S., Montgomery, K., Choi, K. D., Stewart, R., Thomson, J. A., and Slukvin, I I (2011). Efficient generation of transgene-free induced pluripotent stem cells from normal and neoplastic bone marrow and cord blood mononuclear cells. Blood 117, e109-119.

Huang da, W., Sherman, B. T., Stephens, R., Baseler, M. W., Lane, H. C., and Lempicki, R. A. (2008). DAVID gene ID conversion tool. Bioinformation 2, 428-430.

Huang, G., Lu, H., Hao, A., Ng, D. C., Ponniah, S., Guo, K., Lufei, C., Zeng, Q., and Cao, X. (2004). GRIM-19, a cell death regulatory protein, is essential for assembly and function of mitochondrial complex I. Mol Cell Biol 24, 8447-8456.

Jiang, X., Lopez, A., Holyoake, T., Eaves, A., and Eaves, C. (1999). Autocrine production and action of IL-3 and granulocyte colony-stimulating factor in chronic myeloid leukemia. Proc Natl Acad Sci USA 96, 12804-12809.

Koshida, S., Kobayashi, D., Moriai, R., Tsuji, N., and Watanabe, N. (2007). Specific overexpression of OLFM4 (GW112/HGC-1) mRNA in colon, breast and lung cancer tissues detected using quantitative analysis. Cancer science 98, 315-320.

Kumano, K., Arai, S., Hosoi, M., Taoka, K., Takayama, N., Otsu, M., Nagae, G., Ueda, K., Nakazaki, K., Kamikubo, Y., et al. (2012). Generation of induced pluripotent stem cells from primary chronic myelogenous leukemia patient samples. Blood 119, 6234-6242.

Langmead, B., Trapnell, C., Pop, M., and Salzberg, S. L. (2009). Ultrafast and memory-efficient alignment of short DNA sequences to the human genome. Genome Biol 10, R25.

Leng, N., Dawson, J. A., Thomson, J. A., Ruotti, V., Rissman, A. I., Smits, B. M., Haag, J. D., Gould, M. N., Stewart, R. M., and Kendziorski, C. (2013). EBSeq: an empirical Bayes hierarchical model for inference in RNA-seq experiments. Bioinformatics 29, 1035-1043.

Li, B., and Dewey, C. N. (2011). RSEM: accurate transcript quantification from RNA-Seq data with or without a reference genome. BMC Bioinformatics 12, 323.

Li, G., Chan, T. M., Leung, K. S., and Lee, K. H. (2010). A cluster refinement algorithm for motif discovery. IEEE/ACM Trans Comput Biol Bioinform 7, 654-668.

Li, L., Wang, L., Wang, Z., Ho, Y., McDonald, T., Holyoake, T. L., Chen, W., and Bhatia, R. (2012). Activation of p53 by SIRT1 inhibition enhances elimination of CML leukemia stem cells in combination with imatinib. Cancer Cell 21, 266-281.

Liu, R. H., Yang, M. H., Xiang, H., Bao, L. M., Yang, H. A., Yue, L. W., Jiang, X., Ang, N., Wu, L. Y., and Huang, Y. (2012). Depletion of OLFM4 gene inhibits cell growth and increases sensitization to hydrogen peroxide and tumor necrosis factor-alpha induced-apoptosis in gastric cancer cells. J Biomed Sci 19, 38.

Liu, W., Chen, L., Zhu, J., and Rodgers, G. P. (2006). The glycoprotein hGC-1 binds to cadherin and lectins. Exp Cell Res 312, 1785-1797.

Liu, W., Lee, H. W., Liu, Y., Wang, R., and Rodgers, G. P. (2010). Olfactomedin 4 is a novel target gene of retinoic acids and 5-aza-2'-deoxycytidine involved in human myeloid leukemia cell growth, differentiation, and apoptosis. Blood 116, 4938-4947.

Liu, Y., Cheng, H., Gao, S., Zou, Z., He, F., Hu, L., Hou, D., Lu, X., Li, Y., Zhang, H., et al. (2013). Reprogramming of MLL-AF9 leukemia cells into pluripotent stem cells. Leukemia.

Oh, H. K., Tan, A. L., Das, K., Ooi, C. H., Deng, N. T., Tan, I. B., Beillard, E., Lee, J., Ramnarayanan, K., Rha, S. Y., et al. (2011). Genomic loss of miR-486 regulates tumor progression and the OLFM4 antiapoptotic factor in gastric cancer. Clin Cancer Res 17, 2657-2667.

Park, I. H., Zhao, R., West, J. A., Yabuuchi, A., Huo, H., Ince, T. A., Lerou, P. H., Lensch, M. W., and Daley, G. Q. (2008). Reprogramming of human somatic cells to pluripotency with defined factors. Nature 451, 141-146. Epub 2007 December 2023.

Park, K. S., Kim, K. K., Piao, Z. H., Kim, M. K., Lee, H. J., Kim, Y. C., Lee, K. S., Lee, J. H., and Kim, K. E. (2012). Olfactomedin 4 suppresses tumor growth and metastasis of mouse melanoma cells through downregulation of integrin and MMP genes. Mol Cells 34, 555-561.

Petzer, A. L., Eaves, C. J., Lansdorp, P. M., Ponchio, L., Barnett, M. J., and Eaves, A. C. (1996). Characterization of primitive subpopulations of normal and leukemic cells present in the blood of patients with newly diagnosed as well as established chronic myeloid leukemia. Blood 88, 2162-2171.

Pfaffl, M. W. (2001). A new mathematical model for relative quantification in real-time RT-PCR. Nucleic Acids Res 29, e45.

Rais, Y., Zviran, A., Geula, S., Gafni, O., Chomsky, E., Viukov, S., Mansour, A. A., Caspi, I., Krupalnik, V., Zerbib, M., et al. (2013). Deterministic direct reprogramming of somatic cells to pluripotency. Nature 502, 65-70.

Ramaraj, P., Singh, H., Niu, N., Chu, S., Holtz, M., Yee, J. K., and Bhatia, R. (2004). Effect of mutational inactivation of tyrosine kinase activity on BCR/ABL-induced abnormalities in cell growth and adhesion in human hematopoietic progenitors. Cancer Res 64, 5322-5331.

Ramos-Mejia, V., Montes, R., Bueno, C., Ayllon, V., Real, P. J., Rodriguez, R., and Menendez, P. (2012). Residual expression of the reprogramming factors prevents differentiation of iPSC generated from human fibroblasts and cord blood CD34+ progenitors. PLoS One 7, e35824.

Schemionek, M., Elling, C., Steidl, U., Baumer, N., Hamilton, A., Spieker, T., Gothert, J. R., Stehling, M., Wagers, A., Huettner, C. S., et al. (2010). BCR-ABL enhances differentiation of long-term repopulating hematopoietic stem cells. Blood 115, 3185-3195.

Sebaugh, J. L. (2011). Guidelines for accurate EC50/IC50 estimation. Pharm Stat 10, 128-134.

Sloma, I., Jiang, X., Eaves, A. C., and Eaves, C. J. (2010). Insights into the stem cells of chronic myeloid leukemia. Leukemia 24, 1823-1833.

Slukvin, I I (2009). Neoplastic blood cells become pluripotent. Blood 114, 5409-5410.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Tomarev, S. I., and Nakaya, N. (2009). Olfactomedin domain-containing proteins: possible mechanisms of action and functions in normal development and pathology. Mol Neurobiol 40, 122-138.

Udomsakdi, C., Eaves, C. J., Lansdorp, P. M., and Eaves, A. C. (1992a). Phenotypic heterogeneity of primitive leukemic hematopoietic cells in patients with chronic myeloid leukemia. Blood 80, 2522-2530.

Udomsakdi, C., Lansdorp, P. M., Hogge, D. E., Reid, D. S., Eaves, A. C., and Eaves, C. J. (1992b). Characterization of primitive hematopoietic cells in normal human peripheral blood. Blood 80, 2513-2521.

van der Flier, L. G., Haegebarth, A., Stange, D. E., van de Wetering, M., and Clevers, H. (2009). OLFM4 is a robust marker for stem cells in human intestine and marks a subset of colorectal cancer cells. Gastroenterology 137, 15-17.

Vargaftig, J., Taussig, D. C., Griessinger, E., Anjos-Afonso, F., Lister, T. A., Cavenagh, J., Oakervee, H., Gribben, J., and Bonnet, D. (2012). Frequency of leukemic initiating cells does not depend on the xenotransplantation model used. Leukemia 26, 858-860.

Verfaillie, C. M., McCarthy, J. B., and McGlave, P. B. (1992). Mechanisms underlying abnormal trafficking of malignant progenitors in chronic myelogenous leukemia. Decreased adhesion to stroma and fibronectin but increased adhesion to the basement membrane components laminin and collagen type IV. The Journal of clinical investigation 90, 1232-1241.

Vodyanik, M. A., Bork, J. A., Thomson, J. A., and Slukvin, I I (2005). Human embryonic stem cell-derived CD34+ cells: efficient production in the coculture with OP9 stromal cells and analysis of lymphohematopoietic potential. Blood 105, 617-626.

Vodyanik, M. A., Thomson, J. A., and Slukvin, I I (2006). Leukosialin (CD43) defines hematopoietic progenitors in human embryonic stem cell differentiation cultures. Blood 108, 2095-2105.

Ye, Z., Zhan, H., Mali, P., Dowey, S., Williams, D. M., Jang, Y. Y., Dang, C. V., Spivak, J. L., Moliterno, A. R., and Cheng, L. (2009). Human-induced pluripotent stem cells from blood cells of healthy donors and patients with acquired blood disorders. Blood 114, 5473-5480.

Yu, J., Hu, K., Smuga-Otto, K., Tian, S., Stewart, R., Slukvin, I I, and Thomson, J. A. (2009). Human induced pluripotent stem cells free of vector and transgene sequences. Science 324, 797-801.

Zhang, J., Liu, W. L., Tang, D. C., Chen, L., Wang, M., Pack, S. D., Zhuang, Z., and Rodgers, G. P. (2002). Identification and characterization of a novel member of olfactomedin-related protein family, hGC-1, expressed during myeloid lineage development. Gene 283, 83-93.

Zhang, X., Huang, Q., Yang, Z., Li, Y., and Li, C. Y. (2004). GW112, a novel antiapoptotic protein that promotes tumor growth. Cancer Res 64, 2474-2481.

APPENDIX

Gene Expression Analysis of iLSCs versus BMCs in the presence or absence of Imatinib

| Gene symbol | A | B | C | D | E | F | G | H |
|---|---|---|---|---|---|---|---|---|
| Imatinib induced expression in CML but suppressed in BM | | | | | | | | |
| HLA-DRB5 | 1 | 0 | 0 | 1 | 1 | 0 | 0 | 1 |
| GPNMB | 1 | 0 | 0 | 1 | 1 | 0 | 0 | 1 |
| OLR1 | 1 | 0 | 0 | 1 | 1 | 0 | 0 | 1 |
| HLA-DRA | 1 | 0 | 0 | 1 | 1 | 0 | 0 | 1 |
| ACP5 | 1 | 0 | 0 | 1 | 1 | 0 | 0 | 1 |
| C3 | 1 | 0 | 0 | 1 | 1 | 0 | 0 | 1 |
| TLR8 | 1 | 0 | 0 | 1 | 1 | 0 | 0 | 1 |
| APOE | 1 | 0 | 0 | 1 | 1 | 0 | 0 | 1 |
| FPR3 | 1 | 0 | 0 | 1 | 1 | 0 | 0 | 1 |

APPENDIX-continued

Gene Expression Analysis of iLSCs versus BMCs in the presence or absence of Imatinib

| Gene symbol | A | B | C | D | E | F | G | H |
|---|---|---|---|---|---|---|---|---|
| RBP7 | 1 | 0 | 0 | 1 | 0 | 0 | 0 | 1 |
| CYP27A1 | 1 | 0 | 0 | 1 | 1 | 0 | 0 | 1 |
| TPSB2 | 1 | 0 | 0 | 1 | 1 | 0 | 0 | 1 |
| PLEKHG5 | 1 | 0 | 0 | 1 | 1 | 0 | 0 | 1 |
| ABCG1 | 1 | 0 | 0 | 1 | 1 | 0 | 0 | 1 |
| MS4A7 | 1 | 0 | 0 | 1 | 1 | 0 | 0 | 1 |
| SULF2 | 1 | 0 | 0 | 1 | 1 | 0 | 0 | 1 |
| SLC11A1 | 1 | 0 | 0 | 1 | 1 | 0 | 0 | 1 |
| CCL13 | 1 | 0 | 0 | 1 | 1 | 0 | 0 | 1 |
| LGALS3 | 1 | 0 | 0 | 1 | 1 | 0 | 0 | 1 |
| LRP1 | 1 | 0 | 0 | 1 | 1 | 0 | 0 | 1 |
| GRN | 1 | 0 | 0 | 1 | 1 | 0 | 0 | 1 |
| SLAMF8 | 1 | 0 | 0 | 1 | 1 | 0 | 0 | 1 |
| HLA-DMB | 1 | 0 | 0 | 1 | 1 | 0 | 0 | 1 |
| COLEC12 | 1 | 0 | 0 | 1 | 1 | 0 | 0 | 1 |
| ALOX5AP | 1 | 0 | 0 | 1 | 1 | 0 | 0 | 1 |
| IL4I1 | 1 | 0 | 0 | 1 | 1 | 0 | 0 | 1 |
| CEACAM8 | 1 | 0 | 0 | 1 | 1 | 0 | 0 | 1 |
| C19orf59 | 1 | 0 | 0 | 1 | 1 | 0 | 0 | 1 |
| IFI30 | 1 | 0 | 0 | 1 | 1 | 0 | 0 | 1 |
| FCGR2C | 1 | 0 | 0 | 1 | 1 | 0 | 0 | 1 |
| SLCO2B1 | 1 | 0 | 0 | 1 | 1 | 0 | 0 | 1 |
| C1QB | 1 | 0 | 0 | 1 | 1 | 0 | 0 | 1 |
| CCL20 | 1 | 0 | 0 | 1 | 0 | 0 | 0 | 1 |
| CXCL16 | 1 | 0 | 0 | 1 | 1 | 0 | 0 | 1 |
| CHI3L1 | 1 | 0 | 0 | 1 | 1 | 0 | 0 | 1 |
| FBP1 | 1 | 0 | 0 | 1 | 0 | 0 | 0 | 1 |
| ALDH2 | 1 | 0 | 0 | 1 | 1 | 0 | 0 | 1 |
| SLC15A3 | 1 | 0 | 0 | 1 | 1 | 0 | 0 | 1 |
| LILRB5 | 1 | 0 | 0 | 1 | 1 | 0 | 0 | 1 |
| TM6SF1 | 1 | 0 | 0 | 1 | 1 | 0 | 0 | 1 |
| RETN | 1 | 0 | 0 | 1 | 1 | 0 | 0 | 1 |
| CLEC4A | 1 | 0 | 0 | 1 | 1 | 0 | 0 | 1 |
| BCL2A1 | 1 | 0 | 0 | 1 | 1 | 0 | 0 | 1 |
| ARHGEF10L | 1 | 0 | 0 | 1 | 1 | 0 | 0 | 1 |
| NDFIP2 | 1 | 0 | 0 | 1 | 0 | 0 | 0 | 1 |
| CAPG | 1 | 0 | 0 | 1 | 1 | 0 | 0 | 1 |
| SLC8A1 | 1 | 0 | 0 | 1 | 1 | 0 | 0 | 1 |
| C1QA | 1 | 0 | 0 | 1 | 1 | 0 | 0 | 1 |
| HLA-DPA1 | 1 | 0 | 0 | 1 | 1 | 0 | 0 | 1 |
| STAC | 1 | 0 | 0 | 1 | 1 | 0 | 0 | 1 |
| DPYD | 1 | 0 | 0 | 1 | 1 | 0 | 0 | 1 |
| HLA-DMA | 1 | 0 | 0 | 1 | 1 | 0 | 0 | 1 |
| LGMN | 1 | 0 | 0 | 1 | 1 | 0 | 0 | 1 |
| SEMA6B | 1 | 0 | 0 | 1 | 1 | 0 | 0 | 1 |
| TNFSF12 | 1 | 0 | 0 | 1 | 1 | 0 | 0 | 1 |
| MAL | 1 | 0 | 0 | 1 | 1 | 0 | 0 | 1 |
| COL8A2 | 1 | 0 | 0 | 1 | 0 | 0 | 0 | 1 |
| ITGAX | 1 | 0 | 0 | 1 | 1 | 0 | 0 | 1 |
| IL9R | 1 | 0 | 0 | 1 | 0 | 0 | 0 | 1 |
| MATN2 | 1 | 0 | 0 | 1 | 1 | 0 | 0 | 1 |
| SLC7A7 | 1 | 0 | 0 | 1 | 1 | 0 | 0 | 1 |
| KYNU | 1 | 0 | 0 | 1 | 1 | 0 | 0 | 1 |
| APOC1 | 1 | 0 | 0 | 1 | 1 | 0 | 0 | 1 |
| BTG2 | 1 | 0 | 0 | 1 | 1 | 0 | 0 | 1 |
| C3AR1 | 1 | 0 | 0 | 1 | 1 | 0 | 0 | 1 |
| CTSS | 1 | 0 | 0 | 1 | 1 | 0 | 0 | 1 |
| ALOX15 | 1 | 0 | 0 | 1 | 0 | 0 | 0 | 1 |
| HLA-B | 1 | 0 | 0 | 1 | 1 | 0 | 0 | 1 |
| GIMAP8 | 1 | 0 | 0 | 1 | 1 | 0 | 0 | 1 |
| TUBA1A | 1 | 0 | 0 | 1 | 1 | 0 | 0 | 1 |
| DNASE2 | 1 | 0 | 0 | 1 | 1 | 0 | 0 | 1 |
| CD2 | 1 | 0 | 0 | 1 | 0 | 0 | 0 | 1 |
| SBF2 | 1 | 0 | 0 | 1 | 1 | 0 | 0 | 1 |
| CD68 | 1 | 0 | 0 | 1 | 1 | 0 | 0 | 1 |
| BMF | 1 | 0 | 0 | 1 | 1 | 0 | 0 | 1 |
| S100A10 | 1 | 0 | 0 | 1 | 1 | 0 | 0 | 1 |
| TBC1D2 | 1 | 0 | 0 | 1 | 1 | 0 | 0 | 1 |
| SLC37A2 | 1 | 0 | 0 | 1 | 1 | 0 | 0 | 1 |
| BHLHE40 | 1 | 0 | 0 | 1 | 1 | 0 | 0 | 1 |
| RTN1 | 1 | 0 | 0 | 1 | 1 | 0 | 0 | 1 |
| CEACAM1 | 1 | 0 | 0 | 1 | 0 | 0 | 0 | 1 |
| FLVCR2 | 1 | 0 | 0 | 1 | 1 | 0 | 0 | 1 |
| CCDC92 | 1 | 0 | 0 | 1 | 1 | 0 | 0 | 1 |
| FCGR2B | 1 | 0 | 0 | 1 | 1 | 0 | 0 | 1 |

APPENDIX-continued

Gene Expression Analysis of iLSCs versus BMCs in the presence or absence of Imatinib

| Gene symbol | A | B | C | D | E | F | G | H |
|---|---|---|---|---|---|---|---|---|
| MILR1 | 1 | 0 | 0 | 1 | 1 | 0 | 0 | 1 |
| LY86 | 1 | 0 | 0 | 1 | 1 | 0 | 0 | 1 |
| FOLR2 | 1 | 0 | 0 | 1 | 1 | 0 | 0 | 1 |
| CLEC12A | 1 | 0 | 0 | 1 | 0 | 0 | 0 | 1 |
| PLD2 | 1 | 0 | 0 | 1 | 1 | 0 | 0 | 1 |
| AHNAK | 1 | 0 | 0 | 1 | 1 | 0 | 0 | 1 |
| CEACAM4 | 1 | 0 | 0 | 1 | 1 | 0 | 0 | 1 |
| CD300LF | 1 | 0 | 0 | 1 | 1 | 0 | 0 | 1 |
| CTSH | 1 | 0 | 0 | 1 | 1 | 0 | 0 | 1 |
| NCF1 | 1 | 0 | 0 | 1 | 1 | 0 | 0 | 1 |
| S100A6 | 1 | 0 | 0 | 1 | 1 | 0 | 0 | 1 |
| ADAMDEC1 | 1 | 0 | 0 | 1 | 1 | 0 | 0 | 1 |
| PILRA | 1 | 0 | 0 | 1 | 1 | 0 | 0 | 1 |
| SMAD7 | 1 | 0 | 0 | 1 | 1 | 0 | 0 | 1 |
| PMP22 | 1 | 0 | 0 | 1 | 1 | 0 | 0 | 1 |
| TYROBP | 1 | 0 | 0 | 1 | 1 | 0 | 0 | 1 |
| NPC2 | 1 | 0 | 0 | 1 | 1 | 0 | 0 | 1 |
| NLRC4 | 1 | 0 | 0 | 1 | 1 | 0 | 0 | 1 |
| LGALS1 | 1 | 0 | 0 | 1 | 1 | 0 | 0 | 1 |
| RNF19B | 1 | 0 | 0 | 1 | 1 | 0 | 0 | 1 |
| OSCAR | 1 | 0 | 0 | 1 | 1 | 0 | 0 | 1 |
| ALOX5 | 1 | 0 | 0 | 1 | 1 | 0 | 0 | 1 |
| CST3 | 1 | 0 | 0 | 1 | 1 | 0 | 0 | 1 |
| DENND2D | 1 | 0 | 0 | 1 | 1 | 0 | 0 | 1 |
| OLFM4 | 1 | 0 | 0 | 1 | 0 | 1 | 0 | 1 |
| NPL | 1 | 0 | 0 | 1 | 1 | 0 | 0 | 1 |
| ASAH1 | 1 | 0 | 0 | 1 | 1 | 0 | 0 | 1 |
| LAPTM5 | 1 | 0 | 0 | 1 | 1 | 0 | 0 | 1 |
| MYO7B | 1 | 0 | 0 | 1 | 1 | 0 | 0 | 1 |
| TRIM22 | 1 | 0 | 0 | 1 | 0 | 0 | 0 | 1 |
| PPARG | 1 | 0 | 0 | 1 | 1 | 0 | 0 | 1 |
| GIMAP1-GIMAP5 | 1 | 0 | 0 | 1 | 1 | 0 | 0 | 1 |
| RENBP | 1 | 0 | 0 | 1 | 1 | 0 | 0 | 1 |
| PREX1 | 1 | 0 | 0 | 1 | 1 | 0 | 0 | 1 |
| CD52 | 1 | 0 | 0 | 1 | 1 | 0 | 0 | 1 |
| C4orf34 | 1 | 0 | 0 | 1 | 1 | 0 | 0 | 1 |
| SAMHD1 | 1 | 0 | 0 | 1 | 1 | 0 | 0 | 1 |
| HK3 | 1 | 0 | 0 | 1 | 1 | 0 | 0 | 1 |
| QPCT | 1 | 0 | 0 | 1 | 0 | 0 | 0 | 1 |
| GADD45G | 1 | 0 | 0 | 1 | 0 | 0 | 0 | 1 |
| CEACAM21 | 1 | 0 | 0 | 1 | 1 | 0 | 0 | 1 |
| TBX3 | 1 | 0 | 0 | 1 | 1 | 0 | 0 | 1 |
| SORL1 | 1 | 0 | 0 | 1 | 1 | 0 | 0 | 1 |
| *Imatinib induced expression in CML but did not affect in BM* | | | | | | | | |
| INSIG1 | 0 | 0 | 0 | 1 | 0 | 0 | 0 | 1 |
| SIGLEC6 | 0 | 0 | 0 | 1 | 0 | 0 | 0 | 1 |
| CD38 | 0 | 0 | 0 | 1 | 0 | 0 | 0 | 1 |
| TP53INP1 | 0 | 0 | 0 | 1 | 0 | 0 | 0 | 1 |
| NCOA3 | 0 | 0 | 0 | 1 | 1 | 0 | 0 | 1 |
| FILIP1L | 0 | 0 | 0 | 1 | 1 | 0 | 0 | 1 |
| NAPSA | 0 | 0 | 0 | 1 | 0 | 0 | 0 | 1 |
| SKIL | 0 | 0 | 0 | 1 | 1 | 0 | 0 | 1 |
| TCN1 | 0 | 0 | 0 | 1 | 1 | 0 | 0 | 1 |
| *Imatinib induced expression in both CML and BM* | | | | | | | | |
| FRRS1 | 0 | 1 | 0 | 1 | 0 | 0 | 0 | 1 |
| *Imatinib suppressed expression in both CML and BM* | | | | | | | | |
| EGR1 | 1 | 0 | 1 | 0 | 0 | 0 | 1 | 0 |
| *Imatinib suppressed expression in CML but did not affect BM* | | | | | | | | |
| BMP2 | 0 | 0 | 1 | 0 | 0 | 1 | 1 | 0 |
| TERT | 0 | 0 | 1 | 0 | 0 | 1 | 1 | 0 |
| DUSP2 | 0 | 0 | 1 | 0 | 0 | 0 | 1 | 0 |
| METRN | 0 | 0 | 1 | 0 | 0 | 0 | 1 | 0 |

KEY
A = BM: imatinib down-regulated (PP)
B = BM: imatinib up-regulate (PP)
C = CML: imatinib down-regulate (PP)
D = CML: imatinib up-regulate (PP)
E = Control: CML down-regulation compared to BM (PP)
F = Control: CML up-regulation compared to BM (PP)
G = Imatinib: CML down-regulation compared to BM (PP)
H = Imatinib: CML up-regulation compared to BM (PP)
"PP" = Prior Probability Score
Gene Expression Change Categories: 1 = imatinib down-regulated in BM; 2 = imatinib up-regulated in MB; etc . . .

We claim:

1. A method for treating CML comprising administering to a subject in need thereof a therapeutically effective amount of an inhibitor of OLFM4.

2. The method of claim 1, wherein the OLFM4 inhibitor comprises an siRNA against OLFM4 mRNA, an RNAi expression vector against OLFM4 mRNA, or an antibody against OLFM4 protein.

3. The method of claim 1, further comprising administering a therapeutically effective amount of a tyrosine kinase inhibitor.

4. The method of claim 3, wherein the tyrosine kinase inhibitor inhibits BCR-ABL tyrosine kinase.

5. The method of claim 4, wherein the tyrosine kinase inhibitor is imatinib.

6. The method of claim 1, wherein administration of the OLFM4 inhibitor and the tyrosine kinase inhibitor is concurrent.

* * * * *